US011905519B2

United States Patent
Baum et al.

(10) Patent No.: US 11,905,519 B2
(45) Date of Patent: *Feb. 20, 2024

(54) LEPIDOPTERAN-ACTIVE CRY1DA1 AMINO ACID SEQUENCE VARIANT PROTEINS

(71) Applicant: Monsanto Technology LLC, St. Louis, MO (US)

(72) Inventors: James A. Baum, Webster Groves, MO (US); Thomas Cerruti, Newton, MA (US); Stanislaw Flasinski, Chesterfield, MO (US); Xiaoran Fu, Belmont, MA (US); Arlene R. Howe, Chesterfield, MO (US); Sara Ann Salvador, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/815,122

(22) Filed: Jul. 26, 2022

(65) Prior Publication Data

US 2023/0018327 A1 Jan. 19, 2023

Related U.S. Application Data

(63) Continuation of application No. 17/028,518, filed on Sep. 22, 2020, now Pat. No. 11,396,661, which is a continuation of application No. 16/573,538, filed on Sep. 17, 2019, now Pat. No. 10,801,037, which is a continuation of application No. 16/047,187, filed on Jul. 27, 2018, now Pat. No. 10,457,958, which is a continuation of application No. 14/884,432, filed on Oct. 15, 2015, now Pat. No. 10,059,959.

(60) Provisional application No. 62/065,017, filed on Oct. 17, 2014, provisional application No. 62/064,994, filed on Oct. 16, 2014.

(51) Int. Cl.
*C12N 15/82* (2006.01)
*C07K 14/325* (2006.01)
*A01N 63/50* (2020.01)
*A01N 47/08* (2006.01)

(52) U.S. Cl.
CPC ......... *C12N 15/8286* (2013.01); *A01N 47/08* (2013.01); *A01N 63/50* (2020.01); *C07K 14/325* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 5,500,365 A | 3/1996 | Fischhoff et al. | |
| 5,880,275 A | 3/1999 | Fischhoff et al. | |
| 6,033,874 A | 3/2000 | Baum et al. | |
| 6,172,281 B1 * | 1/2001 | Van Mellaert | C12N 1/205 800/302 |
| 6,501,009 B1 | 12/2002 | Romano | |
| 6,573,240 B1 | 6/2003 | Payne et al. | |
| 6,713,063 B1 | 3/2004 | Malvar et al. | |
| 6,962,705 B2 | 11/2005 | Malvar et al. | |
| 7,064,249 B2 | 6/2006 | Corbin et al. | |
| 7,070,982 B2 | 7/2006 | Malvar et al. | |
| 7,510,878 B2 | 3/2009 | Abad et al. | |
| 7,511,129 B2 | 3/2009 | Payne | |
| 7,772,465 B2 | 8/2010 | Abad et al. | |
| 7,812,129 B1 | 10/2010 | Abad et al. | |
| 7,927,598 B2 | 4/2011 | Malvar et al. | |
| 8,344,207 B2 | 1/2013 | Bogdanova et al. | |
| 8,609,936 B2 | 12/2013 | Baum et al. | |
| 9,890,390 B2 | 2/2018 | Tan et al. | |
| 2003/0084606 A1 | 5/2003 | Parker | |
| 2004/0058860 A1 | 3/2004 | Payne et al. | |
| 2004/0172671 A1 | 9/2004 | Ali et al. | |
| 2005/0155103 A1 | 7/2005 | Baum et al. | |
| 2006/0021087 A1 | 1/2006 | Baum et al. | |
| 2006/0112447 A1 | 5/2006 | Bogdanova et al. | |
| 2008/0172762 A1 | 7/2008 | Cerf et al. | |
| 2009/0313721 A1 | 12/2009 | Abad et al. | |
| 2010/0004176 A1 | 1/2010 | Sampson et al. | |
| 2010/0017914 A1 | 1/2010 | Hart et al. | |

(Continued)

FOREIGN PATENT DOCUMENTS

| | | |
|---|---|---|
| EP | 0358557 | 3/1990 |
| WO | 93/07278 | 4/1993 |

(Continued)

OTHER PUBLICATIONS

Aronson et al. "Why Bacillus thuringiensis Insecticidal Toxins are so Effective: Unique Features of their Mode of Action," FEMS Microbiol. Lett., 195:1-8) (2001).

(Continued)

*Primary Examiner* — Weihua Fan
(74) *Attorney, Agent, or Firm* — Dentons US LLP; Timothy K. Ball

(57) ABSTRACT

Engineered Cry1Da amino acid sequences are provided that exhibit improved Lepidopteran insecticidal activity and an enhanced Lepidopteran spectrum compared to the naturally occurring Cry1Da protein toxin. Polynucleotide sequences intended for use in expression of the improved proteins in plants are also provided. Particular embodiments provide compositions containing insect inhibitory amounts of the engineered proteins, as well as recombinant plants, plant parts, and seeds containing polynucleotide constructs encoding one or more of the improved engineered proteins.

21 Claims, 1 Drawing Sheet

Specification includes a Sequence Listing.

(56) References Cited

U.S. PATENT DOCUMENTS

| | | |
|---|---|---|
| 2010/0077507 A1 | 3/2010 | Abad et al. |
| 2010/0077508 A1 | 3/2010 | Abad et al. |
| 2010/0137216 A1 | 6/2010 | Carozzi et al. |
| 2010/0160231 A1 | 6/2010 | Sampson et al. |
| 2010/0192256 A1 | 7/2010 | Abad et al. |
| 2010/0197592 A1 | 8/2010 | Heinrichs |
| 2010/0269221 A1 | 10/2010 | Abad et al. |
| 2010/0317569 A1 | 12/2010 | Lira et al. |
| 2010/0319092 A1 | 12/2010 | Lira et al. |
| 2010/0319093 A1 | 12/2010 | Lira et al. |
| 2011/0030096 A1 | 2/2011 | Sampson et al. |
| 2011/0055968 A1 | 3/2011 | Cerf et al. |
| 2011/0112013 A1 | 5/2011 | Abad et al. |
| 2011/0154536 A1 | 6/2011 | Abad et al. |
| 2012/0047606 A1 | 2/2012 | Abad et al. |
| 2012/0117690 A1 | 5/2012 | Cerf et al. |
| 2012/0167259 A1 | 6/2012 | Liu et al. |
| 2012/0192310 A1 | 7/2012 | Abad et al. |
| 2012/0210462 A1 | 8/2012 | Bermudez et al. |
| 2012/0233726 A1 | 9/2012 | Abad et al. |
| 2013/0055469 A1 | 2/2013 | Sampson et al. |
| 2013/0097735 A1 | 4/2013 | Bowen et al. |
| 2013/0104259 A1 | 4/2013 | Sampson et al. |
| 2013/0117884 A1 | 5/2013 | Hargiss et al. |
| 2013/0167264 A1 | 6/2013 | Sampson et al. |
| 2013/0219570 A1 | 8/2013 | Lira et al. |
| 2013/0269060 A1 | 10/2013 | Baum et al. |
| 2013/0303440 A1 | 11/2013 | Sampson et al. |
| 2013/0310543 A1 | 11/2013 | Samson et al. |
| 2014/0007292 A1 | 1/2014 | Cerf et al. |
| 2014/0033361 A1 | 1/2014 | Altier et al. |
| 2014/0033363 A1 | 1/2014 | Sampson |
| 2014/0196175 A1 | 7/2014 | Sampson et al. |
| 2014/0223598 A1 | 8/2014 | Sampson et al. |
| 2014/0223599 A1 | 8/2014 | Sampson et al. |
| 2014/0245491 A1 | 8/2014 | Sampson et al. |
| 2014/0298538 A1 | 10/2014 | Heinrichs et al. |
| 2014/0366227 A1 | 12/2014 | Gatehouse et al. |
| 2014/0373195 A1 | 12/2014 | Sampson et al. |

FOREIGN PATENT DOCUMENTS

| | | |
|---|---|---|
| WO | 98/23641 | 6/1998 |
| WO | 00/26371 | 5/2000 |
| WO | 01/45122 | 6/2001 |
| WO | 02/15701 | 2/2002 |
| WO | 02/40677 | 5/2002 |
| WO | 02/100163 | 12/2002 |
| WO | 2004/020636 | 3/2004 |
| WO | 2011/041256 | 4/2011 |
| WO | 2012/139004 | 10/2012 |
| WO | 2014/008054 | 1/2014 |
| WO | 2014/055881 | 4/2014 |
| WO | 2014/066151 | 5/2014 |

OTHER PUBLICATIONS

Bravo et al. "Evolution of Bacillus thuringiensis Cry Toxins Insecticidal Activity, Microbial Biotechnology," 6:17-26 (2012).

Crickmore et al. "Revision of the Nomenclature for Bacilllus thuringiensis Pesticidal Crystal Proteins," Microbiology and Molecular Biology Reviews, 62(3):807-813 (1998).

De Maagd et al. Identification of Bacillus thuringiensis Delta-Endotoxin Cry1C Domain III Amino Acid Residues Involved in Insect Specificity, Appl Environ. Microbiol 65:4369-4374, 1999) (1999).

Gryson et al. "Detection of DNA during the referring of soybean oil," Journal of Oil & Fat Industries. 79:171-174 (2002).

Höfte et al. "Insecticidal Crystal Proteins of Bacillus thuringiensis," Microbiological Reviews, 53:242-255 (1989).

Höfte et al. "Nucleotide Sequence and Deduced Amino Acid Sequence of a New Lepidoptera-specific Crystal Protein Gene from Bacillus thuringiensis," Nucleic Acids Research, 18(18):5545 (1990).

International Search Report dated Jun. 20, 2016, in International Patent Application No. PCT/US2015/055779.

IUPAC-IUB Joint Commission on Biochemical Nomenclature, "Nomenclature and Symbolism for Amino Acids and Peptides," Eur. J. Biochem. 138:9-37 (1984).

Kim et al. "Mutagenesis of Bacillus Thuringiensis cry1Ac gene and its insecticidal activity against Plutella xylostella and Ostrinia furnacalis," Biological Control, 47(2):222-227 (2008).

Lucena et al. "Molecular Approaches to Imrove the Insecticidal Activity of Bacillus thuringiensis Cry toxins," Toxins, 6(8):2393-2423 (2014).

Pardo-Lopez et al. "Strategies to Improve the Insecticidal Activity of Cry Toxins from Bacillus thuringiensis," Peptides, 30(3):589-595 (2008).

Rajamohan et al. "Protein Engineering of Bacillus thuringiensis Δ-endotoxin: Mutations at Domain II of Cry1Ab Enhance Receptor Affinity and Toxicity toward Gypsy Moth larvae," Proceedings of the National Academy of Sciences U.S.A. 93(25):14338-14343 (1996).

Saraswathy et al. "Protein Engineering of Delta-endotoxins of Bacillus thuringiensis," Electronic Journal of Biotechnology, 7(2):178-188 (2004).

Search Report dated Apr. 17, 2020, in African Regional Intellectual Property Organisation Application No. AP/P/2017/009885.

Silvio Alejandro Lopez-Pazos et al. "Biological Activity of Insecticidal Toxins: Structural Basis, Site-Directed Mutagenesis and Perspectives," Genetic Manipulation of DNA and Protein—Examples from Current Research, David Figurski, IntechOpen, DOI: 10:5772/55895. (2013).

Sonke et al., "Detection of Genomic DNA from Processed Plant Oils and Wheat Flour," Web, May 26, 2020 <https://www.sigmaaldrich.com/technical-documents/articles/biology/detection-of-genomic-dna-from-processed-plant-oils-wheat-flour.html>.

Tabashnik et al. "Cross-Resistance of Pink Bollworm (*Pectinophora gossypiella*) to Bacillus thuringiensis Toxins," Applied and Environmental Microbiology, 66:4582-4584 (2000).

Tabashnik et al. "Cross-Resistance to Bacillus thuringiensis Toxin Cry1Ja in a Strain of Diamondback Moth Adapted to Artificial Diet," Journal of invertebrate Pathology, 76:81-83 (2000).

Thompson et al. "CLUSTAL W: improving the Sensitivity of Progressive Multiple Sequence Alignment Through Sequence Weighting, Position-specific Gap Penalties and Weight Matrix Choice," Nucleic Acids Research, 22:4673-4680 (1994).

Tounsi et al. "Cloning and Study of the Expression of a Novel cry1Ia-type Gene from Bacillus thuringiensis subsp. *Kurstaki*" J. Appl. Microbiol. 95:23-28 (2003).

Vietina et al., "Applicability of SSE markers to the traceability of monovarietal olive oils," J. Sci Food Agric, 91:1381-1391 (2011).

Yu et al. "Effect of Cry1Ca7 Protein Modified by Site-directed Mutagenesis on Inhibiting Spodoptera exigua Hubner," Acta Microbiologica Sinica, 48(6):733-738 (2008).

\* cited by examiner

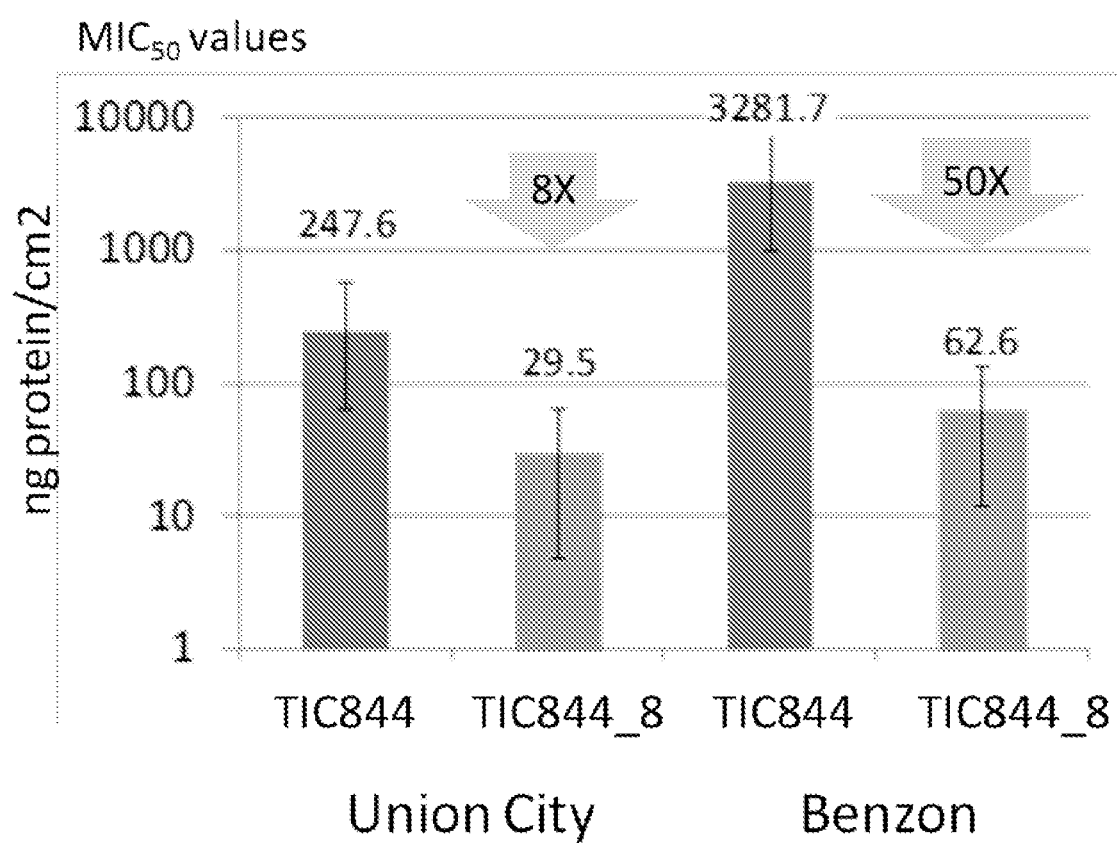

US 11,905,519 B2

LEPIDOPTERAN-ACTIVE CRY1DA1 AMINO ACID SEQUENCE VARIANT PROTEINS

REFERENCE TO RELATED APPLICATIONS

This application is a continuation of U.S. patent application Ser. No. 17/028,518, filed Sep. 22, 2020, which is a continuation of U.S. patent application Ser. No. 16/573,538, filed Sep. 17, 2019, which is a continuation of U.S. patent application Ser. No. 16/047,187, filed Jul. 27, 2018, which is a continuation of U.S. patent application Ser. No. 14/884,432, filed Oct. 15, 2015, which claims the benefit of U.S. Provisional Application No. 62/065,017, filed Oct. 17, 2014, and U.S. Provisional Application No. 62/064,994, filed Oct. 16, 2014, all of which are incorporated by reference in their entireties herein.

INCORPORATION OF SEQUENCE LISTING

A computer readable form of the Sequence Listing is filed herewith by electronic submission. The Sequence Listing is incorporated by reference in its entirety, is contained in the file created on Jul. 26, 2022, having the file name MONS517USC4.xml, and which is 160,886 bytes in size (as measured in the MS-Windows® operating system).

FIELD OF THE INVENTION

The invention generally relates to the field of insect inhibitory proteins. A novel class of engineered proteins exhibiting insect inhibitory activity against agriculturally-relevant pests of crop plants and seeds is disclosed. In particular, the disclosed class of engineered inhibitory proteins has insecticidal activity against the Lepidopteran order of insect pests. Plants, plant parts, and seeds containing a polynucleotide construct encoding one or more of the disclosed engineered inhibitory proteins are provided.

BACKGROUND OF THE INVENTION

*Helicoverpa zea* is a significant Lepidopteran pest of major agricultural crops, including corn, cotton, and soy. Known as the corn earworm (CEW), cotton bollworm (CBW), and soy podworm (SPW), this polyphagous insect species is particularly difficult to control with insecticidal proteins from *Bacillus thuringiensis* (Bt) or other bacterial species. *H. zea* is considered at risk for resistance development to current insect control traits, given its ability to feed on many different crops and the current absence of a high-dose control strategy. Accordingly, new modes of action (MoA) are required to ensure the durability of transgenic plants protected from *H. zea* feeding damage.

The Cry1Da1 protein is a Lepidopteran-active protein that was first described by Hofte, et al. "Nucleotide sequence and deduced amino acid sequence of a new Lepidoptera-specific crystal protein gene from *Bacillus thuringiensis*." *Nucleic Acids Res.* 18(18) (1990): 5545. This protein exhibits excellent insecticidal activity towards *Spodoptera* species including *Spodoptera frugiperda* (fall armyworm, FAW), a pest of several row crops, including corn, cotton and soybean. However, Cry1Da1 exhibits low-to-moderate activity towards a variety of other major Lepidopteran pests, including bollworms (e.g., *Helicoverpa armigera* and *H. zea*), borers (e.g., *Ostrinia nubilalis* and *Diatraea grandiosella*) and soybean looper (*Pseudoplusia includens*). Because of its narrow insecticidal spectrum and its inability to provide commercial-level protection against a range of important Lepidopteran agricultural pests such as CEW, the Cry1Da1 insecticidal protein has limited value as a transgenic plant insect control trait. As a result, no current commercial varieties of insect-protected crops utilize Cry1Da1 as a plant-incorporated protectant.

Despite its narrow insecticidal spectrum, Cry1Da1 is an interesting insecticidal protein because it appears that the Cry1Da1 protein uses an alternative MoA for controlling certain Lepidopteran pests. Evidence for this comes from studies with multiple resistant insect colonies. For example, field-derived colonies of *Plutella xylostella* (diamondback moth) and *Pectinophora gossypiella* (pink bollworm) that are resistant to Cry1Ac intoxication retain full sensitivity to the Cry1Da1 protein (Tabashnik, et al. "Cross-Resistance of Pink Bollworm (*Pectinophora gossypiella*) to *Bacillus thuringiensis* toxins." *Appl. Environ. Microbiol.* 66 (2000): 4582-4584; Tabashnik, et al. "Cross-Resistance to *Bacillus thuringiensis* Toxin Cry1Ja in a Strain of Diamondback Moth Adapted to Artificial Diet." *J. Invert. Pathol.* 76: (2000): 81-83.). These lines of evidence indicate that Cry1Da1 recognizes Lepidopteran midgut receptors distinct from those recognized by Lepidopteran-active proteins currently deployed in transgenic crops, including Cry1Ac, Cry1Ab, Cry1A.105, Cry1Fa, Cry2Ae, and Cry2Ab2. In view of this apparent novel MoA, optimization of Cry1Da1-like proteins for improved activity against a broader spectrum of *Helicoverpa* species while maintaining or increasing their insecticidal activity towards *Spodoptera* would create a high-value plant-incorporated protectant for insect resistance management.

SUMMARY OF THE INVENTION

In the present invention, several amino acid sequence variants of the TIC844 and Cry1Da scaffold proteins have been identified that exhibit markedly improved activity (compared to the Cry1Da1 native toxin) towards *H. zea* while retaining excellent activity towards *S. frugiperda*. The improved variants of TIC844 and Cry1Da have been engineered to be expressed in crop plants (e.g., corn, soybean, cotton, sugarcane), and provide novel options for in-planta resistance management and Lepidopteran insect pest control in view of the apparent unique mode-of-action of Cry1Da coupled with the engineered improvement in activity against *H. zea*.

The engineered Lepidopteran toxic proteins described herein (referred to as "engineered toxin proteins", "engineered toxic proteins", or "engineered insecticidal proteins") are derivatives of the naturally occurring *Bacillus thuringiensis* insecticidal toxin Cry1Da1 (SEQ ID NO:2) or the chimeric homolog of Cry1Da1, TIC844 (SEQ ID NO:14), which comprises the Cry1Da1 core toxin but substitutes the Cry1Ab3 protoxin for the native Cry1Da1 protoxin domain. The engineered insecticidal proteins of the present invention each contain at least one amino acid substitution, one amino acid addition, or one amino acid deletion compared to the scaffold proteins set forth in any of SEQ ID NO:2 or SEQ ID NO:14. The engineered insecticidal proteins of the present invention are particularly toxic to insects of the *Helicoverpa zea* (corn earworm, soy podworm, cotton bollworm) and *Spodoptera frugiperda* (fall armyworm) species. While the scaffold proteins TIC844 (SEQ ID NO:14) and Cry1Da1 (SEQ ID NO:2) display low toxicity to *H. zea*, the engineered insecticidal proteins of the present invention exhibit surprising and unexpectedly improved insecticidal activity and an enhanced insecticidal spectrum against Lepidopteran insect pests including *H. zea*.

In certain embodiments, an engineered insecticidal protein comprising an amino acid sequence as set forth in any of SEQ ID NO:44, SEQ ID NO: 40, SEQ ID NO: 12, SEQ ID NO:26, SEQ ID NO:4, SEQ ID NO:6, SEQ ID NO:8, SEQ ID NO:10, SEQ ID NO:16, SEQ ID NO:18, SEQ ID NO:20, SEQ ID NO:22, SEQ ID NO:24, SEQ ID NO:32, SEQ ID NO:34, SEQ ID NO:36, SEQ ID NO:38 or SEQ ID NO:42, or an insect inhibitory fragment thereof is disclosed. In certain embodiments, the engineered insecticidal protein exhibits inhibitory activity against an insect species of the order Lepidoptera. The target Lepidopteran pest species inhibited by the Lepidopteran toxic proteins of the present invention include at least fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Chrysodeixis includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*), European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*), codling moth (*Cydia pomonella*), grape berry moth (*Endopiza viteana*), oriental fruit moth (*Grapholita molesta*), sunflower bud moth (*Suleima helianthana*), diamondback moth (*Plutella xylostella*), pink bollworm (*Pectinophora gossypiella*), pink stem borer (*Sesamia inferens*), gypsy moth (*Lymantria dispar*), cotton leaf worm (*Alabama argillacea*), fruit tree leaf roller (*Archips argyrospila*), European leafroller (*Archips rosana*), Asiatic rice borer, or rice stem borer (*Chilo suppressalis*), rice leaf roller (*Cnaphalocrocis medinalis*), corn root webworm (*Crambus caliginosellus*), bluegrass webworm (*Crambus teterrellus*), southwestern corn borer (*Diatraea grandiosella*)), surgarcane borer (*Diatraea saccharalis*), spiny bollworm (*Earias insulana*), spotted bollworm (*Earias vittella*), Old World cotton bollworm (*Helicoverpa armigera*), corn earworm, soy podworm or cotton bollworm (*Helicoverpa zea*), sod webworm (*Herpetogramma licarsisalis*), European grape vine moth (*Lobesia botrana*), citrus leafminer (*Phyllocnistis citrella*), large white butterfly (*Pieris brassicae*), imported cabbageworm, or small white butterfly (*Pieris rapae*), tobacco cutworm, or cluster caterpillar (*Spodoptera litura*), and tomato leafminer (*Tuta absoluta*).

Also disclosed herein is a polynucleotide encoding an engineered insecticidal protein or pesticidal fragment thereof, wherein the polynucleotide is operably linked to a heterologous promoter and the engineered insecticidal protein comprises the amino acid sequence as set forth in any of SEQ ID NO:44, SEQ ID NO: 40, SEQ ID NO: 12, SEQ ID NO:26, SEQ ID NO:4, SEQ ID NO:6, SEQ ID NO:8, SEQ ID NO:10, SEQ ID NO:16, SEQ ID NO:18, SEQ ID NO:20, SEQ ID NO:22, SEQ ID NO:24, SEQ ID NO:32, SEQ ID NO:34, SEQ ID NO:36, SEQ ID NO:38 or SEQ ID NO:42.

In another embodiment, disclosed herein is a polynucleotide encoding an engineered insecticidal protein, wherein the polynucleotide comprises a nucleotide sequence that optionally hybridizes under stringent conditions to the reverse complement of the polynucleotide sequence as set forth in any of SEQ ID NO: 43, SEQ ID NO: 39, SEQ ID NO: 11, SEQ ID NO: 11, SEQ ID NO: 25, SEQ ID NO: 3, SEQ ID NO: 5, SEQ ID NO: 7, SEQ ID NO: 9, SEQ ID NO: 15, SEQ ID NO: 17, SEQ ID NO: 19, SEQ ID NO: 21, SEQ ID NO: 23, SEQ ID NO:31, SEQ ID NO: 33, SEQ ID NO: 35, SEQ ID NO: 37 or SEQ ID NO: 41; or encodes the engineered insecticidal protein comprising an amino acid sequence as set forth in any of SEQ ID NO:44, SEQ ID NO: 40, SEQ ID NO: 12, SEQ ID NO:26, SEQ ID NO:4, SEQ ID NO:6, SEQ ID NO:8, SEQ ID NO:10, SEQ ID NO:16, SEQ ID NO:18, SEQ ID NO:20, SEQ ID NO:22, SEQ ID NO:24, SEQ ID NO:32, SEQ ID NO:34, SEQ ID NO:36, SEQ ID NO:38 or SEQ ID NO:42.

Also provided herein is a host cell comprising the polynucleotide set forth in any of SEQ ID NO: 43, SEQ ID NO: 39, SEQ ID NO: 11, SEQ ID NO: 11, SEQ ID NO: 25, SEQ ID NO: 3, SEQ ID NO: 5, SEQ ID NO: 7, SEQ ID NO: 9, SEQ ID NO: 15, SEQ ID NO: 17, SEQ ID NO: 19, SEQ ID NO: 21, SEQ ID NO: 23, SEQ ID NO:31, SEQ ID NO: 33, SEQ ID NO: 35, SEQ ID NO: 37 or SEQ ID NO: 41, wherein the host cell is selected from the group consisting of a bacterial host cell or a plant host cell. Contemplated bacterial host cells include bacterial host cells selected from the group consisting of *Agrobacterium, Rhizobium, Bacillus, Brevibacillus, Escherichia, Pseudomonas, Klebsiella*, and *Erwinia*, wherein the *Bacillus* species is a *Bacillus cereus* or a *Bacillus thuringiensis*, said *Brevibacillus* is a *Brevibacillus laterosperous*, and said *Escherichia* is an *Escherichia coli*. Further, contemplated plant host cells include monocots or dicots.

In yet another embodiment, provided herein is an insect inhibitory composition comprising an engineered insecticidal protein comprising an amino acid sequence as set forth in any of SEQ ID NO:44, SEQ ID NO: 40, SEQ ID NO: 12, SEQ ID NO:26, SEQ ID NO:4, SEQ ID NO:6, SEQ ID NO:8, SEQ ID NO:10, SEQ ID NO:16, SEQ ID NO:18, SEQ ID NO:20, SEQ ID NO:22, SEQ ID NO:24, SEQ ID NO:32, SEQ ID NO:34, SEQ ID NO:36, SEQ ID NO:38 or SEQ ID NO:42 or an insect inhibitory fragment thereof. It is contemplated that this insect inhibitory composition can further comprise at least one insect inhibitory agent different from the engineered insecticidal protein. Contemplated insect inhibitory agents include an insect inhibitory protein, an insect inhibitory dsRNA molecule, and an insect inhibitory chemistry. It is contemplated that the at least one other pesticidal agent can exhibit activity against one or more pest species of the orders Lepidoptera, Coleoptera, Hemiptera, Homoptera, or Thysanoptera.

Also disclosed herein are is a seed comprising an insect inhibitory effective amount of an engineered insecticidal protein comprising the amino acid sequence as set forth in any of SEQ ID NO:44, SEQ ID NO: 40, SEQ ID NO: 12, SEQ ID NO:26, SEQ ID NO:4, SEQ ID NO:6, SEQ ID NO:8, SEQ ID NO:10, SEQ ID NO:16, SEQ ID NO:18, SEQ ID NO:20, SEQ ID NO:22, SEQ ID NO:24, SEQ ID NO:32, SEQ ID NO:34, SEQ ID NO:36, SEQ ID NO:38 or SEQ ID NO:42; or a polynucleotide set forth in any of SEQ ID NO: 43, SEQ ID NO: 39, SEQ ID NO: 11, SEQ ID NO: 11, SEQ ID NO: 25, SEQ ID NO: 3, SEQ ID NO: 5, SEQ ID NO: 7, SEQ ID NO: 9, SEQ ID NO: 15, SEQ ID NO: 17, SEQ ID NO: 19, SEQ ID NO: 21, SEQ ID NO: 23, SEQ ID NO:31, SEQ ID NO: 33, SEQ ID NO: 35, SEQ ID NO: 37 or SEQ ID NO: 41.

A method for controlling a Lepidopteran pest, the method comprising contacting the Lepidopteran pest with an inhibitory amount of an engineered insecticidal protein is also disclosed herein in another embodiment.

In yet another embodiment, disclosed herein is a transgenic plant cell, plant or plant part comprising an engineered insecticidal protein Methods are provided for controlling a Lepidopteran pest, comprising exposing the pest to the transgenic plant cell, plant or plant part comprising an engineered insecticidal protein. Commodity products derived from the plant cell, plant or plant part comprising an engineered insecticidal protein wherein the product comprises a detectable amount of the engineered insecticidal protein are also contemplated. Contemplated commodity products include plant biomass, oil, meal, animal feed, flour, flakes, bran, lint, hulls, and processed seed Another method disclosed herein is a method of producing a seed comprising the engineered insecticidal protein, the method comprising: planting at least one seed comprising the engineered insecticidal protein; growing plants from said seed; and harvesting seed from the plants, wherein said harvested seed comprises the engineered insecticidal protein.

Yet another method disclosed in this application is a method of inhibiting Lepidopteran pests from feeding on a crop plant comprising modifying one or more amino acid residue(s) of SEQ ID NO: 2 or SEQ ID NO:14 through substitution of the one or more amino acid residue(s) to produce a modified SEQ ID NO:2 or SEQ ID NO:14; and making available a Lepidopteran-inhibiting amount of the modified SEQ ID NO: 2 or SEQ ID NO:14 within, on the surface, or in the vicinity of tissues of said crop plant; wherein the SEQ ID NO:2 or SEQ ID NO:14 modified amino acid residue is selected from the group consisting of serine at position 282 replaced by lysine or valine, tyrosine at position 316 replaced by serine, isoleucine at position 368 replaced by proline or arginine, serine at 374 replaced by arginine, asparagine at position 375 replaced by histidine, and isoleucine at position 432 replaced by leucine.

Recombinant polynucleotide molecules that encode the engineered insecticidal proteins of the present invention are also provided. Contemplated recombinant polynucleotide molecules comprise a polynucleotide sequence selected from the group consisting of SEQ ID NO: 43, SEQ ID NO: 39, SEQ ID NO: 11, SEQ ID NO: 11, SEQ ID NO: 25, SEQ ID NO: 3, SEQ ID NO: 5, SEQ ID NO: 7, SEQ ID NO: 9, SEQ ID NO: 15, SEQ ID NO: 17, SEQ ID NO: 19, SEQ ID NO: 21, SEQ ID NO: 23, SEQ ID NO:31, SEQ ID NO: 33, SEQ ID NO: 35, SEQ ID NO: 37 or SEQ ID NO: 41; and optionally a polynucleotide sequence encoding an insect inhibitory agent different from the engineered insecticidal protein.

Another method disclosed in this application is method for increasing the Lepidopteran activity and enhancing the Lepidopteran inhibitory spectrum of a scaffold protein, the method comprising modifying one or more amino acid residue(s) of SEQ ID NO: 2 or SEQ ID NO: 14 through substitution of the amino acid residue(s) to produce an engineered insecticidal protein, wherein the SEQ ID NO:2 or SEQ ID NO:14 modified amino acid residue is selected from the group consisting of serine at position 282 replaced by lysine or valine, tyrosine at position 316 replaced by serine, isoleucine at position 368 replaced by proline or arginine, serine at 374 replaced by arginine, asparagine at position 375 replaced by histidine, and isoleucine at position 432 replaced by leucine. In certain embodiments of this method, the engineered insecticidal protein has at least an eight-fold increase in *Helicoverpa zea* lethality relative to the scaffold protein Other embodiments, features, and advantages of the invention will be apparent from the following detailed description, the examples, and the claims.

BRIEF DESCRIPTION OF THE DRAWINGS

FIG. 1 illustrates the MIC$_{50}$ values of the scaffold protein TIC844 (SEQ ID NO: 14) compared to the engineered insecticidal protein TIC844_8 (SEQ ID NO: 26) for two different *Helicoverpa zea* (CEW) colonies, Union City and Benzon.

BRIEF DESCRIPTION OF THE SEQUENCES

SEQ ID NO:1 is a nucleotide sequence encoding a Cry1Da1 protein.
SEQ ID NO:2 is an amino acid sequence of a Cry1Da1protein toxin.
SEQ ID NO:3 is a nucleotide sequence encoding a Cry1Da1_3 protein.
SEQ ID NO:4 is an amino acid sequence of a Cry1Da1_3 protein toxin.
SEQ ID NO:5 is a nucleotide sequence encoding a Cry1Da1_4 protein.
SEQ ID NO:6 is an amino acid sequence of a Cry1Da1_4 protein toxin.
SEQ ID NO:7 is a nucleotide sequence encoding a Cry1Da1_5 protein.
SEQ ID NO:8 is an amino acid sequence of a Cry1Da1_5 protein toxin.
SEQ ID NO:9 is a nucleotide sequence encoding a Cry1Da1_6 protein.
SEQ ID NO:10 is an amino acid sequence of a Cry1Da1_6 protein toxin.
SEQ ID NO:11 is a nucleotide sequence encoding a Cry1Da1_7 protein.
SEQ ID NO:12 is an amino acid sequence of a Cry1Da1_7 protein toxin.
SEQ ID NO:13 is a nucleotide sequence encoding a TIC844 protein.
SEQ ID NO:14 is an amino acid sequence of a TIC844 protein toxin.
SEQ ID NO:15 is a nucleotide sequence encoding a TIC844_2 protein.
SEQ ID NO:16 is an amino acid sequence of a TIC844_2 protein toxin.
SEQ ID NO:17 is a nucleotide sequence encoding a TIC844_4 protein.
SEQ ID NO:18 is an amino acid sequence of a TIC844_4 protein toxin.
SEQ ID NO:19 is a nucleotide sequence encoding a TIC844_5 protein.
SEQ ID NO:20 is an amino acid sequence of a TIC844_5 protein toxin.
SEQ ID NO:21 is a nucleotide sequence encoding a TIC844_6 protein.
SEQ ID NO:22 is an amino acid sequence of a TIC844_6 protein toxin.
SEQ ID NO:23 is a nucleotide sequence encoding a TIC844_7 protein.
SEQ ID NO:24 is an amino acid sequence of a TIC844_7 protein toxin.
SEQ ID NO:25 is a nucleotide sequence encoding a TIC844_8 protein.
SEQ ID NO:26 is an amino acid sequence of a TIC844_8 protein toxin.
SEQ ID NO:27 is a polynucleotide sequence designed for use in expressing a Cry1Da1 protein in plants.
SEQ ID NO:28 is an amino acid sequence of a Cry1Da1 protein toxin.
SEQ ID NO:29 is a polynucleotide sequence designed for use in expressing a Cry1Da1_2.nno protein in plants.
SEQ ID NO:30 is an amino acid sequence of a Cry1Da1_2.nno protein toxin.

SEQ ID NO:31 is a polynucleotide sequence designed for use in expressing a Cry1Da1_3.nno protein in plants.

SEQ ID NO:32 is an amino acid sequence of a Cry1Da1_3.nno protein toxin.

SEQ ID NO:33 is a polynucleotide sequence designed for use in expressing a Cry1Da1_4.nno protein in plants.

SEQ ID NO:34 is an amino acid sequence of a Cry1Da1_4.nno protein toxin.

SEQ ID NO:35 is a polynucleotide sequence designed for use in expressing a Cry1Da1_5.nno protein in plants.

SEQ ID NO:36 is an amino acid sequence of a Cry1Da1_5.nno protein toxin.

SEQ ID NO:37 is a polynucleotide sequence designed for use in expressing a Cry1Da1_6.nno protein in plants.

SEQ ID NO:38 is an amino acid sequence of a Cry1Da1_6.nno protein toxin.

SEQ ID NO:39 is a polynucleotide sequence designed for use in expressing a Cry1Da1_7.nno protein in plants.

SEQ ID NO:40 is an amino acid sequence of a Cry1Da1_7.nno protein toxin.

SEQ ID NO:41 is a polynucleotide sequence designed for use in expressing a TIC844_9.nno protein in plants.

SEQ ID NO:42 is an amino acid sequence of a TIC844_9.nno protein toxin.

SEQ ID NO:43 is a polynucleotide sequence designed for use in expressing a TIC844_11.nno protein in plants.

SEQ ID NO:44 is an amino acid sequence of a TIC844_11.nno protein toxin.

DETAILED DESCRIPTION OF THE INVENTION

Engineered insecticidal proteins that exhibit surprisingly higher levels of toxic activity against Lepidopteran species and a broader insecticidal spectrum compared to other previously known Lepidopteran insecticidal proteins are provided herein. These engineered insecticidal proteins are derived from insecticidal scaffold proteins, which serve as templates for various amino acid modifications. Examples of such insecticidal scaffold proteins include but are not limited to Cry1Da1 and TIC844 (a homolog of Cry1Da1). TIC844 comprises the Cry1Da1 core toxin (i.e., domains I, II and III) but utilizes the Cry1Ab3 protoxin domain to ensure good expression in *Bacillus thuringiensis* (Bt). Expression of Cry1Da1 in Bt is poor when using the native Cry1Da1 protoxin domain. However, as demonstrated in this application, the expression of Cry1Da1 core toxin is remarkably improved in acrystalliferous strains of Bt when the native protoxin domain is removed and the Cry1Da1 core toxin coding segment is fused in frame with a segment encoding the Cry1Ab3 protoxin domain. Notably, the scaffold proteins TIC844 (SEQ ID NO:14) and Cry1Da1 (SEQ ID NO:2) do not exhibit the commercially useful Lepidopteran inhibitory spectrum and improved Lepidopteran inhibitory activity observed in the engineered insecticidal proteins.

The engineered insecticidal proteins disclosed herein are related by amino acid modifications such that the modified proteins exhibit enhanced Lepidopteran inhibitory spectrum and/or improved Lepidopteran inhibitory activity compared to the parent scaffold protein, TIC844 or Cry1Da1. The phrases "more active", "improved activity", "enhanced specificity", "increased toxic potency", "increased toxicity", "improved Lepidopteran inhibitory activity", "greater Lepidopteran inhibitory activity", and "enhanced Lepidopteran inhibitory spectrum" refer to a comparison of the activity of an engineered insecticidal protein to the activity of a scaffold protein (TIC844 or Cry1Da1) against a Lepidopteran insect, wherein the activity attributed to the engineered insecticidal protein is greater than the activity attributed to the scaffold protein. In certain embodiments, the engineered insecticidal proteins provided herein exhibit an enhanced Lepidopteran inhibitory spectrum and/or improved or greater Lepidopteran inhibitory activity when compared to the activities of the scaffold TIC844 or Cry1Da1 protein where the Lepidopteran pest species include, but are not limited to, *Helicoverpa zea* and *Spodoptera frugiperda*.

As used herein, the terms and phrases "active" or "activity"; "pesticidal activity" or "pesticidal"; or "insecticidal activity", "insect inhibitory", "insecticidal", or "an insect inhibitory amount", refer to efficacy of a toxic agent, such as an insecticidal protein, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of a disclosed engineered insecticidal protein) or killing (causing the morbidity, mortality, or reduced fecundity of) a pest. Similarly, a "Lepidopteran inhibitory amount" refers to an amount of a toxic agent, such as an insecticidal protein, that results in any measurable inhibition of Lepidopteran viability, Lepidopteran growth, Lepidopteran development, Lepidopteran reproduction, Lepidopteran feeding behavior, Lepidopteran mating behavior and/or any measurable decrease in the adverse effects caused to a plant by Lepidopteran feeding. These terms are intended to include the result of providing a pesticidally effective amount of a toxic agent to a pest where the exposure of the pest to the toxic agent results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic agent in or on the plant. In general, pesticidal activity refers to the ability of a toxic agent to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera. The toxic agent can be produced by the plant or can be applied to the plant or to the environment within the location where the plant is located.

A pesticidally effective amount of a toxic agent, when provided in the diet of a target pest, exhibits pesticidal activity when the toxic is ingested by the pest. A toxic agent can be a pesticidal protein or one or more chemical agents known in the art. Pesticidal or insecticidal chemical agents and pesticidal or insecticidal protein agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Pesticidal or insecticidal protein agents include the engineered insecticidal proteins set forth in this application, as well as other proteinaceous toxic agents including those that target Lepidopteran pest species, as well as protein toxins that are used to control other plant pests such as Cry proteins available in the art for use in controlling Coleopteran, Hemipteran and Homopteran species.

The term "segment" or "fragment" is used herein to describe consecutive amino acid or nucleic acid sequences that are shorter than the complete amino acid or nucleic acid sequence describing the engineered insecticidal proteins.

It is intended that reference to a pest, particularly a pest of a crop plant, means insect pests of crop plants, particularly those Lepidopteran insect pests that are controlled by the disclosed engineered insecticidal proteins. However, reference to a pest can also include Coleopteran, Hemipteran and Homopteran insect pests of plants, as well as nematodes and fungi, when toxic agents targeting these pests are co-localized or present together with the disclosed engineered insecticidal proteins.

The disclosed engineered insecticidal proteins exhibit insecticidal activity towards insect pests from the Lepidopteran insect species, including adults, pupae, larvae, and neonates. The insects of the order Lepidoptera include, but are not limited to, armyworms, cutworms, loopers, and heliothines in the Family Noctuidae, e.g., fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*) and gypsy moth (*Lymantria dispar*). Other insect pests of order Lepidoptera include, e.g., *Alabama argillacea* (cotton leafworm), *Archips argyrospila* (fruit tree leaf roller), *Archips rosana* (European leafroller) and other *Archips* species, *Chilo suppressalis* (Asiatic rice borer, or rice stem borer), *Cnaphalocrocis medinalis* (rice leaf roller), *Crambus caliginosellus* (corn root webworm), *Crambus teterrellus* (bluegrass webworm), *Diatraea grandiosella* (southwestern corn borer), *Diatraea saccharalis* (surgarcane borer), *Earias insulana* (spiny bollworm), *Earias vittella* (spotted bollworm), *Helicoverpa armigera* (American bollworm), *Helicoverpa zea* (corn earworm or cotton bollworm), *Heliothis virescens* (tobacco budworm), *Herpetogramma licarsisalis* (sod webworm), *Lobesia botrana* (European grape vine moth), *Phyllocnistis citrella* (citrus leafminer), *Pieris brassicae* (large white butterfly), *Pieris rapae* (imported cabbageworm, or small white butterfly), *Plutella xylostella* (diamondback moth), *Spodoptera exigua* (beet armyworm), *Spodoptera litura* (tobacco cutworm, cluster caterpillar), and *Tuta absoluta* (tomato leafminer).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of a naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further in the Examples, repetitive rounds of engineering, testing and selecting of over two thousand (2000) amino acid sequence variants of TIC844 and Cry1Da1 resulted in the identification of certain amino acid residues that may be substituted, inserted or deleted from the given scaffold protein to produce engineered insecticidal proteins that exhibit an expanded Lepidopteran inhibitory spectrum and/or improved Lepidopteran inhibitory activity (i.e., more toxic; less insecticidal protein required to obtain same level of mortality) when compared to the spectrum and activity of the baseline scaffold proteins, TIC844 or Cry1Da1. These repetitive rounds of engineering, testing and selecting also resulted in the identification of neutral amino acid residue substitutions, insertions or deletions in the TIC844 and Cry1Da1 scaffold proteins that do not change the proteins' insect inhibitory spectrum or activity. The specific amino acid residues in the TIC844 and Cry1Da1 scaffold that can be modified to yield an enhanced Lepidopteran inhibitory spectrum and/or improved Lepidopteran inhibitory activity relative to TIC844 or Cry1Da1 are identified herein. In certain embodiments, the engineered insecticidal protein provided herein can exhibit about an eight fold or greater Lepidopteran inhibitory activity against a Lepidopteran pest species than a scaffold protein of SEQ ID NO:14 (TIC844) or SEQ ID NO:2 (Cry1Da1).

The "engineering" in these repetitive rounds included identifying relevant residues in the scaffold protein to modify to create a modified test protein, and cloning and expressing the resultant modified test proteins. The atomic structure of the scaffold proteins was used to guide and complement semi-random approaches of selecting amino acid residues to modify for engineering. The "testing" in these repetitive rounds included comparing the Lepidopteran species activities of a modified test protein to its parent scaffold protein. The "selecting" in these repetitive rounds included identifying modified test proteins with improved activity (improved variants) and the relevant residues which were engineered to create these improved variants (these improved variants are referred to herein as "engineered insecticidal proteins").

Examples of methods for testing and selecting engineered insecticidal proteins include administering identical amounts of a modified test protein and of a scaffold protein (TIC844 or Cry1Da1) to an insect pest under controlled assay conditions and measuring and comparing the potency of the modified test and scaffold proteins. Another method for testing and selecting engineered insecticidal proteins includes determining the protein doses (e.g., protein concentration in diet) of a modified test protein and of a scaffold protein (TIC844 or Cry1Da1) which elicit equivalent insect population responses under controlled assay conditions (i.e., obtaining a dose response curve). A statistically robust dose response value used for comparison would be the median lethal concentration ($LC_{50}$) required to kill 50% of a test population or the molting inhibition concentration ("$MIC_{50}$", the median concentration required to inhibit molting by 50%).

In certain embodiments, the engineered insecticidal proteins described herein include at least one amino acid modification of the following relative positions of TIC844 (SEQ ID NO:14) or Cry1Da1 (SEQ ID NO:2): serine at position 282 replaced by lysine or valine, tyrosine at position 316 replaced by serine, isoleucine at position 368 replaced by proline or arginine, serine at 374 replaced by arginine, asparagine at position 375 replaced by histidine, and isoleucine at position 432 replaced by leucine. The engineered insecticidal proteins can also include at least two, three, four, or more of these amino acid substitutions or deletions within the same engineered insecticidal protein sequence.

The engineered insecticidal proteins that include these amino acid modifications include the proteins set forth as SEQ ID NO:4, SEQ ID NO:6, SEQ ID NO:8, SEQ ID NO:10, SEQ ID NO:12, SEQ ID NO:16, SEQ ID NO:18, SEQ ID NO:20, SEQ ID NO:22, SEQ ID NO:24, SEQ ID NO:26, SEQ ID NO:32, SEQ ID NO:34, SEQ ID NO:36, SEQ ID NO:38, SEQ ID NO:40, and SEQ ID NO:44, and insect inhibitory fragments thereof. Each of these engineered insecticidal proteins has a measured mass of about 132k-Daltons. Individual characteristics of the insecticidal scaffold proteins TIC844 and Cry1Da1 and the engineered insecticidal proteins derived therefrom are reported in Table 1.

TABLE 1

Characteristics of TIC844, Cry1Da1 and the Engineered Insecticidal Proteins.

| Protein (Name/SEQ ID NO.) | Molecular Weight (in Daltons) | Amino Acid Length | Isoelectric Point | Charge at PH 7.0 | No. of Strongly Basic (—) Amino Acids | No. of Strongly Acidic Amino Acids | No. of Hydrophobic Amino Acids | No. of Polar Amino Acids |
|---|---|---|---|---|---|---|---|---|
| Cry1Da1/ NO: 2 | 132481.87 | 1165 | 5.087 | −39.319 | 113 | 156 | 388 | 347 |
| Cry1Da1_3/ NO: 4 | 132405.77 | 1165 | 5.087 | −39.318 | 113 | 156 | 388 | 347 |
| Cry1Da1_4/ NO: 6 | 132550.98 | 1165 | 5.112 | −38.319 | 114 | 156 | 388 | 346 |
| Cry1Da1_5/ NO: 8 | 132448.80 | 1165 | 5.112 | −38.318 | 114 | 156 | 387 | 347 |
| Cry1Da1_6/ NO: 10 | 132430.82 | 1165 | 5.112 | −38.319 | 114 | 156 | 387 | 346 |
| Cry1Da1_7/ NO: 12 | 132401.78 | 1165 | 5.087 | −39.318 | 113 | 156 | 388 | 346 |
| TIC844/ NO: 14 | 129182.91 | 1139 | 5.026 | −39.540 | 110 | 153 | 382 | 340 |
| TIC844_2/ NO: 16 | 129129.85 | 1139 | 5.048 | −39.373 | 110 | 153 | 382 | 339 |
| TIC844_4/ NO: 18 | 129106.81 | 1139 | 5.026 | −39.539 | 110 | 153 | 382 | 340 |
| TIC844_5/ NO: 20 | 1291118.08 | 1069 | 5.325 | −27.535 | 105 | 136 | 363 | 321 |
| TIC844_6/ NO: 22 | 129252.02 | 1139 | 5.050 | −38.540 | 111 | 153 | 382 | 339 |
| TIC844_7/ NO: 24 | 129149.84 | 1139 | 5.050 | −38.539 | 111 | 153 | 381 | 340 |
| TIC844_8/ NO: 26 | 129102.82 | 1139 | 5.026 | −39.539 | 110 | 153 | 382 | 339 |
| Cry1Da1/ NO: 28 | 132481.87 | 1165 | 5.087 | −39.319 | 113 | 156 | 388 | 347 |
| Cry1Da1_2.nno/ NO: 30 | 132552.95 | 1166 | 5.087 | −39.319 | 113 | 156 | 389 | 347 |
| Cry1Da1_3nno/ NO: 32 | 132476.85 | 1166 | 5.087 | −39.318 | 113 | 156 | 389 | 347 |
| Cry1Da1_4.nno/ NO: 34 | 132622.06 | 1166 | 5.112 | −38.319 | 114 | 156 | 389 | 346 |
| Cry1Da1_5.nno/ NO: 36 | 132519.88 | 1166 | 5.112 | −38.318 | 114 | 156 | 388 | 347 |
| Cry1Da1_6.nno/ NO: 38 | 132501.90 | 1166 | 5.112 | −39.319 | 114 | 156 | 388 | 346 |
| Cry1Da1_7.nno/ NO: 40 | 132472.86 | 1166 | 5.087 | −39.318 | 113 | 156 | 389 | 346 |
| TIC844_9.nno/ NO: 42 | 129253.99 | 1140 | 5.026 | −39.540 | 110 | 153 | 383 | 340 |
| TIC844_11.nno/ NO: 44 | 129173.90 | 1140 | 5.026 | −39.539 | 110 | 153 | 383 | 339 |

Fragments of the engineered insecticidal proteins described herein can be truncated forms wherein one or more amino acids are deleted from the N-terminal end, C-terminal end, the middle of the protein, or combinations thereof without a loss of insect inhibitory activity. These fragments should retain the insect inhibitory activity of the parent engineered insecticidal protein.

Proteins that resemble the engineered insecticidal proteins can be identified by comparison to each other using various computer based algorithms known in the art. For example, amino acid sequence identities of proteins related to the engineered insecticidal proteins can be analyzed using a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment.

As described further in the Examples of this application, synthetic or artificial sequences encoding the scaffold proteins and the engineered insecticidal proteins were designed for use in plants. Exemplary synthetic nucleotide sequences that were designed for use in plants are set forth in SEQ ID NO:27 (Cry1Da1.nno), SEQ ID NO:29 (Cry1Da1_2.nno), SEQ ID NO:31 (Cry1Da1_3.nno), SEQ ID NO:33 (Cry1Da1_4.nno), SEQ ID NO:35 (Cry1Da1_5.nno), SEQ ID NO:37 (Cry1Da1_6.nno), SEQ ID NO:39 (Cry1Da1_7.nno), SEQ ID NO:41 (TIC844_9.nno) and SEQ ID NO:43 (TIC844_11.nno).

Expression cassettes and vectors containing these synthetic or artificial nucleotide sequences were constructed and introduced into corn, cotton and soybean plant cells in accordance with transformation methods and techniques known in the art. Transformed cells were regenerated into transformed plants that were observed to be expressing the engineered insecticidal protein or the scaffold protein. To test pesticidal activity, bioassays were performed in the presence of Lepidopteran pest larvae using plant leaf disks obtained from the transformed plants.

Recombinant nucleic acid molecule compositions that encode the engineered insecticidal proteins are contemplated. For example, an engineered insecticidal protein can be expressed with recombinant DNA constructs in which a polynucleotide molecule with an ORF encoding the engineered insecticidal protein is operably linked to genetic expression elements such as a promoter and any other regulatory element necessary for expression in the system for which the construct is intended. Non-limiting examples include a plant-functional promoter operably linked to the synthetic engineered insecticidal protein encoding sequences for expression of the engineered insecticidal protein in plants or a Bt-functional promoter operably linked to an engineered insecticidal protein encoding sequence for expression of the protein in a Bt bacterium or other *Bacillus* species. Other elements can be operably linked to the engineered insecticidal protein encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herein include, but are not limited to, a heterologous promoter operably linked to a polynucleotide such as SEQ ID NO:3, SEQ ID NO:5, SEQ ID NO:7, SEQ ID NO:9, SEQ ID NO:11, SEQ ID NO:15, SEQ ID NO:17, SEQ ID NO:19, SEQ ID NO:21, SEQ ID NO:23, SEQ ID NO:25, SEQ ID NO:31, SEQ ID NO:33, SEQ ID NO:35, SEQ ID NO:37, SEQ ID NO:39 and SEQ ID NO:43, that encodes the polypeptide or protein having the amino acid sequence as set forth in SEQ ID NO:4 (Cry1Da1_3), SEQ ID NO:6 (Cry1Da1_4), SEQ ID NO:8 (Cry1Da1_5), SEQ ID NO:10 (Cry1Da1_6), SEQ ID NO:12 (Cry1Da1_7), SEQ ID NO:16 (TIC844_2), SEQ ID NO:18 (TIC844_4), SEQ ID NO:20 (TIC844_5), SEQ ID NO:22 (TIC844_6), SEQ ID NO:24 (TIC844_7), SEQ ID NO:26 (TIC844_8), SEQ ID NO:32 (Cry1Da1_3.nno), SEQ ID NO:34 (Cry1Da1_4.nno), SEQ ID NO:36 (Cry1Da1_5.nno), SEQ ID NO:38 (Cry1Da1_6.nno), SEQ ID NO:40 (Cry1Da1_7.nno) and SEQ ID NO:44 (TIC844_11.nno). A heterologous promoter can also be operably linked to synthetic DNA coding sequences encoding a plastid targeted engineered insecticidal protein and untargeted engineered insecticidal protein. It is contemplated that the codons of a recombinant nucleic acid molecule encoding for an engineered insecticidal protein disclosed herein can be substituted by synonymous codons (known in the art as a silent substitution).

A recombinant DNA molecule or construct comprising an engineered insecticidal protein encoding sequence can further comprise a region of DNA that encodes for one or more toxic agents which can be configured to concomitantly express or co-express with a DNA sequence encoding an engineered insecticidal protein, a protein different from an engineered insecticidal protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA molecule or construct can be assembled so that all proteins or dsRNA molecules are expressed from one promoter or each protein or dsRNA molecule is under separate promoter control or some combination thereof. The proteins of this invention can be expressed from a multi-gene expression system in which an engineered insecticidal protein is expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked expression cassettes, each expressing a different protein or other toxic agent such as one or more dsRNA molecules.

Recombinant nucleic acid molecules or recombinant DNA constructs comprising an engineered insecticidal protein encoding sequence can be delivered to host cells by vectors, e.g., a plasmid, baculovirus, synthetic chromosome, virion, cosmid, phagemid, phage, or viral vector. Such vectors can be used to achieve stable or transient expression of an engineered insecticidal protein encoding sequence in a host cell, or subsequent expression of the encoded polypeptide. An exogenous recombinant polynucleotide or recombinant DNA construct that comprises an engineered insecticidal protein sequence encoding sequence and that is introduced into a host cell is referred herein as a "transgene".

Transgenic bacteria, transgenic plant cells, transgenic plants, and transgenic plant parts that contain a polynucleotide that encodes any one or more of the engineered insecticidal proteins are provided herein. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include but is not limited to a dicotyledonous cell or a monocotyledonous cell. Contemplated plants and plant cells include, but are not limited to, alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise Lepidoptera-inhibitory amounts of an engineered insecticidal proteins are provided. Such plants can be made by introducing a polynucleotide that encodes the engineered insecticidal proteins provided in this application into a plant cell, and selecting a plant derived from said plant cell that expresses an insect or Lepidoptera-inhibitory amount of the engineered insecticidal protein. Plants can be derived from the plant cells by regeneration, seed, pollen, or meristem transformation techniques. Methods for transforming plants are known in the art.

Plants expressing the engineered insecticidal proteins can be crossed by breeding with transgenic events expressing other insecticidal proteins and/or expressing other transgenic traits such as other insect control traits, herbicide tolerance genes, genes conferring yield or stress tolerance traits, and the like, or such traits can be combined in a single vector so that the traits are all linked.

Processed plant products, wherein the processed product comprises a detectable amount of an engineered insecticidal protein, an insect inhibitory segment or fragment thereof, or any distinguishing portion thereof, are also disclosed in this application. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of an engineered insecticidal protein.

Methods of controlling insects, in particular Lepidoptera infestations of crop plants, with the engineered insecticidal proteins are also disclosed in this application. Such methods can comprise growing a plant comprising an insect- or Lepidoptera-inhibitory amount of the engineered insecticidal protein. In certain embodiments, such methods can further comprise any one or more of: (i) applying any composition comprising or encoding an engineered insecticidal protein to a plant or a seed that gives rise to a plant; and (ii) transforming a plant or a plant cell that gives rise to a plant with a polynucleotide encoding an engineered insecticidal protein. In general, it is contemplated that engineered insecticidal protein can be provided in a composition, provided in a microorganism, or provided in a transgenic plant to confer insect inhibitory activity against Lepidopteran insects.

In certain embodiments, the engineered insecticidal protein is the insecticidally active ingredient of an insect inhibitory composition prepared by culturing recombinant *Bacillus* or any other recombinant bacterial cell transformed to express an engineered insecticidal protein under conditions suitable for expression. Such a composition can be prepared by desiccation, lyophilization, homogenization, extraction, filtration, centrifugation, sedimentation, or concentration of a culture of such recombinant cells expressing/producing the engineered insecticidal protein. Such a process can result in a *Bacillus* or other entomopathogenic bacterial cell extract, cell suspension, cell homogenate, cell lysate, cell supernatant, cell filtrate, or cell pellet. By obtaining the engineered insecticidal protein so produced, a composition that includes the engineered insecticidal protein can include bacterial cells, bacterial spores, and parasporal inclusion bodies and can be formulated for various uses, including as agricultural insect inhibitory spray products or as insect inhibitory formulations in diet bioassays.

In an embodiment, in order to reduce the likelihood of resistance development, an insect inhibitory composition or transgenic plant comprising an engineered insecticidal protein can further comprise at least one additional toxic agent that exhibits insect inhibitory activity against the same Lepidopteran insect species, but which is different from the engineered insecticidal protein. Possible additional toxic agents for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide (s) for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. Patent Publication No. 10/525,318), Cry1C (U.S. Pat. No. 6,033,874), Cry1D, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U. S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1); and the like.

In other embodiments, an insect inhibitory composition or transgenic plant can further comprise at least one additional toxic agent that exhibits insect inhibitory activity to an insect pest that is not inhibited by the engineered insecticidal proteins of the present invention (such as Coleopteran, Hemipteran and Homopteran pests), in order to expand the spectrum of insect inhibition obtained.

Such additional toxic agent for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), axmi207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), IP3 and variants thereof (U.S. Patent Publication 2012-0210462 A1), and $\overline{\omega}$-Hexatoxin-Hv1a (U.S. Patent Application Publication US2014-0366227 A1).

Such additional toxic agent for the control of Hemipteran pests may be selected from the group consisting of Hemipteran-active proteins such as, but not limited to, TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Additional polypeptides for the control of Coleopteran, Lepidopteran, and Hemipteran insect pests can be found on the *Bacillus thuringiensis* toxin nomenclature website maintained by Neil Crickmore (on the world wide web at btnomenclature.info).

Engineered insecticidal protein-encoding sequences and sequences having a substantial percentage identity to the engineered insecticidal proteins can be identified using methods known to those of ordinary skill in the art such as polymerase chain reaction (PCR), thermal amplification and hybridization. For example, the engineered insecticidal proteins can be used to produce antibodies that bind specifically to related proteins, and can be used to screen for and to find other proteins that are closely related.

Furthermore, nucleotide sequences encoding the engineered insecticidal proteins can be used as probes and primers for screening to identify other members of the class using thermal-cycle or isothermal amplification and hybridization methods. For example, oligonucleotides derived from sequences as set forth in SEQ ID NO: 3 can be used to determine the presence or absence of an engineered insecticidal transgene in a deoxyribonucleic acid sample derived from a commodity product. Given the sensitivity of certain nucleic acid detection methods that employ oligonucleotides, it is anticipated that oligonucleotides derived from sequences as set forth in any of SEQ ID NO: 3 can be used to detect the respective engineered insecticidal protein in commodity products derived from pooled sources where only a fraction of the commodity product is derived from a transgenic plant containing any of SEQ ID NO: 3.

Other features and advantages of the invention will be apparent from the following Examples and claims.

EXAMPLES

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

Example 1

Design of Modified Test Proteins and Sample Preparation for Insect Bioassay Testing This Example illustrates the methods undertaken to identify relevant amino acid residues in the scaffold proteins to modify to create modified test proteins, and the cloning and expressing of the resultant modified test proteins.

Several molecular engineering techniques were employed in a tiered approach to construct improved variants of Cry1Da1 having an enhanced Lepidopteran inhibitory spectrum and/or improved Lepidopteran inhibitory activity compared to the scaffold proteins of Cry1Da1 and TIC844, a homolog of Cry1Da1. The first tier, or initial round of design, was primarily hypothesis driven. The second and third tiers were statistically-driven rounds of design. For example, in the second tier of design, statistically non-deleterious mutations were combined with putative beneficial mutations to produce double mutations which satisfied defined statistical criteria. In the third tier of design, all the data from the previous tests was analyzed using multiple statistical methods. Only mutations showing statistically significant improvement in more than one statistical method were selected to the final pool of mutations. The variants designed in this tier contained one or two more positive mutations from variants previously confirmed positive. Thus, the third tier design significantly enriched the active variants compared to the first and second tier. As demonstrated in the subsequent Examples, the use of the three-tiered design strategy identified both single and synergistic mutations that provided significant improvement in activity against CEW for certain improved variants relative to the TIC844 and Cry1Da1 scaffolds.

The methods which were utilized to create the modified test proteins included, but were not limited to, semi-random modifications, directed modifications of variances in alignment of TIC844/Cry1Da1 with other native *Bacillus thuringensis* (Bt) proteins, and structure/function assisted design. Examples of utilized molecular engineering techniques include the following.

Receptor binding. Susceptibility of Lepidopteran pests, specifically Corn Earworm (CEW, *Helicoverpa zea*) to Cry1Da1/TIC844 improved variants may be attributable to different targeted gut receptors. Designs which were utilized to improve binding to receptors in the gut, thus increasing toxicity, included: (1) mutating every position in the apical loops of domain II to all amino-acid types; and (2) swapping all possible combinations of the apical loops of domain II with those from other Cry1Da1 homologs (e.g., Cry1db1, Cry1Dc1) and CEW-active three-domain toxins (e.g., Cry1Bb1, Cry1Ja1 and Cry2Ab2).

Alignment based approaches. Alignment of Cry1Da1 with other homologs (e.g., Cry1db1 and Cry1Dc1) was used to identify regions of variability. As a result of the alignment, one hundred fifty (150) positions and two hundred ninety five (295) unique single mutations were identified. These positions were located throughout the three domains. Positions within four (4) amino acids from one another were grouped together. Only mutations from the same parental sequences were nominated for every group of positions, rendering one hundred thirty two (132) unique variants.

Surface mutagenesis approaches. The polynucleotides encoding the surface positions in domains II and III of the scaffold proteins were mutagenized by a scan. Amino acid residues were modified to alanine where an alanine was not already present in the scaffold protein. At surface positions where the native residues were lysine, arginine mutations were introduced in addition to the alanine mutations. The rational for the lysine to arginine mutations was based on the observation that Lepidopteran-active toxins tend to have very few lysine and many arginine and, therefore, it was hypothesized that changing the surface lysine positions in domains II and III to arginine would increase the Lepidopteran activity of the modified test protein.

Alteration of proteolytic events. The proteolytic process was hypothesized to be an important aspect of the activity of three-domain toxins in the Lepidopteran insect guts. In order to test this, several sets of mutations were made to potentially alter any proteolytic cleavage. Potential cleavage sites are located at the N-terminus and between domain III and the protoxin. The mutational positions included predicted loop regions from the N-terminus to the beginning of helix 4 and from the C-terminus of domain III to ~40 amino acids into the protoxin. Generally, glycine residues were hypothesized to promote proteolysis either through proteolytic site recognition or by increasing the protein flexibility, thereby rendering it more susceptible to proteolytic cleavage. Further, trypsin and chymotripsin are two proteases that are widely accepted as viable proteases in Lepidopteran midguts. Lysine residues provide recognition sites for trypsin and tyrosine residues provide recognition sites for chymotripsin. Thus, selected mutational positions in the potential cleavage sites were mutated to either glycine, lysine or tyrosine.

Potential hot-spot mutations from other CEW-active toxins. Activity and absence of activity data against CEW for a large set of proteins (including chimeras, fragments and native sequences) was analyzed. Information gained from a statistical analysis of this data was utilized to identify potential specific mutations or positions for mutation that would be likely to increase CEW activity in the resultant modified test proteins.

The modified test proteins which resulted from the molecular engineering methodologies described above were cloned using methods known in the art into a recombinant Bt plasmid expression vector downstream of a sporulation specific expression promoter and transformed into an acrystalliferous Bt host cell.

Example 2

Testing of Modified Test Proteins in Diet Bioassays Against Lepidopteran Pests

This Example illustrates the testing of the modified test proteins created from the engineering efforts described in Example 1.

From the engineering efforts described in Example 1, about two thousand five hundred (2,500) recombinant Bt strains were produced which expressed more than two thousand three hundred (2,300) different modified test proteins. These modified test proteins were expressed in Bt and assayed for toxicity to various species of Lepidoptera. Feeding assays were conducted with neonate larvae (<24 hour post hatch) of various Lepidopteran species, including corn earworm (CEW, *Helicoverpa zea*) and fall armyworm (FAW, *Spodoptera frugiperda*). Insect eggs for the CEW testing were obtained from two different laboratory colonies: Benson Research, Carlisle, Pa. and Monsanto Company, Union City, Tenn. All of the expressed modified test proteins were tested on CEW and some of those modified test proteins demonstrating improved activity against CEW compared to their parent scaffold proteins were tested on FAW, in addition to performing additional bioassays to confirm CEW activity.

Various protocols for bioassays and scoring insects for mortality and stunting are known in the art. Variations of methods, such as those described in PCT Patent Application Publication No. WO 2012/139004 and in U.S. Pat. No. 7,927,598, were used.

Example 3

Modified Test Proteins Exhibiting Improved CEW Activity

This Example illustrates the discovery of an enhanced Lepidopteran inhibitory spectrum and/or improved or greater Lepidopteran inhibitory activity for some of the modified test proteins when compared to the activities of the scaffold TIC844 or Cry1Da1 proteins in multiple testing rounds.

The modified tests proteins created from the engineering efforts described in Example 1 and and tested in insect bioassay as described in Example 2 were tested in repetitive rounds in which the Lepidopteran species activities of the modified test proteins were compared to their respective parent scaffold proteins (i.e., TIC844 or Cry1Da1). In a first round, three hundred and seventy (370) different modified test proteins demonstrated increased toxicity against CEW relative to TIC844 or Cry1Da1 in diet bioassays. In each of these diet bioassays, identical amounts of the protein (either modified test protein or scaffold protein) was provided to CEW under controlled single-dose assay conditions. The potency of the modified test proteins and scaffold proteins was determined by measuring and comparing the observed mortality and stunting of each of the modified test protein bioassays to the observed mortality and stunting of the parent scaffold protein bioassays.

Of the three hundred and seventy (370) modified test proteins which demonstrated increased toxicity against CEW when compared to the scaffold proteins in single-dose assay screens, about one hundred eighty (180) of them were further tested in FAW bioassays to determine whether these modified test proteins maintained or exhibited increased FAW activity compared to their scaffold protein parents. About forty (40) to fifty (50) of these modified test proteins exhibited similar or better FAW activity than their parent scaffold proteins. These further-screened modified test proteins were also tested in additional CEW bioassays to confirm CEW activity. These rounds of selecting and testing modified test proteins which demonstrated improved CEW activity while maintaining or improving FAW activity resulted in a final list of improved variants (referred to herein as the "engineered insecticidal proteins"). Table 2 identifies these engineered insecticidal proteins and the amino acid mutations in each engineered insecticidal protein. Table 2 also demonstrates the activity of the scaffold and the engineered insecticidal proteins against CEW and FAW (insecticidal activity is demonstrated in $LC_{50}$ value (the toxin concentration required to kill 50% of an insect population during a fixed exposure duration. The lower the $LC_{50}$ value, the greater the toxicity) and the $MIC_{50}$ value (the concentration required to inhibit molting to a specific instar of 50% of the larvae during a fixed exposure duration). This Table demonstrates that the engineered insecticidal proteins have improved CEW-activity, while maintaining or improving FAW activity.

TABLE 2

Amino Acid Mutations and Activity Data for Scaffold Proteins and Engineered Insecticidal Proteins.

| Protein (Name/SEQ ID NO.) | Amino Acid Mutations* | $LC_{50}$ ($\mu g/cm^2$) against CEW Benzon colony with spore-crystal bioassay prep | $MIC_{50}$ ($\mu g/cm^2$) against CEW Benzon colony with spore-crystal bioassay prep |
|---|---|---|---|
| Cry1Da1/ NO: 2, 28 | None (scaffold protein) | NA** | ~3.0 |
| Cry1Da1_3/ NO: 4 | Cry1Da1 + Y316S | NA** | NA** |
| Cry1Da1_4/ NO: 6 | Cry1Da1 + S374R | NA** | NA** |
| Cry1Da1_5/ NO: 8 | Cry1Da1 + Y316S_I368R | NA** | NA** |
| Cry1Da1_6/ NO: 10 | Cry1Da1 + S282K_Y316S_I368P | NA** | NA** |
| Cry1Da1_7/ NO: 12 | Cry1Da1 + S282V_Y316S_I368P | NA** | NA** |
| TIC844/ NO: 14 | None (scaffold protein) | 41.90 | 3.73 |
| TIC844_2/ NO: 16 | TIC844 + Y316S_N375H_I432L | 0.81 | 0.65 |
| TIC844_4/ NO: 18 | TIC844 + Y316S | 0.98 | 0.57 |
| TIC844_5/ NO: 20 | TIC844 + S282K_Y316S_I368P | 0.32 | 0.33 |
| TIC844_6/ NO: 22 | TIC844 + S374R | 4.09 | 1.39 |
| TIC844_7/ NO: 24 | TIC844 + Y316S_I368R | 0.93 | 0.61 |
| TIC844_8/ NO: 26 | TIC844 + S282V_Y316S_I368P | 0.221 | .064 |

*The amino acid mutations are identified using the standard IUPAC amino acid code. See IUPAC-IUB Joint Commission on Biochemical Nomenclature. Nomenclature and Symbolism for Amino Acids and Peptides. Eur. J. Biochem. 138:9-37(1984). The first amino acid sequence abbreviation indicates the original amino acid in the given scaffold protein, the number represents the position of the amino acid, and the second amino acid sequence abbreviation indicates the amino acid placed in that position in the improved variant protein.
**The core toxin of Cry1Da1 is identical to the core toxin of TIC844.

Further demonstrating the enhanced Lepidopteran inhibitory spectrum and improved Lepidopteran inhibitory activity of the engineered insecticidal proteins, the lethality of engineered insecticidal protein TIC844_8 relative to its parent scaffold protein is demonstrated in FIG. 1. The bar chart of FIG. 1 demonstrates the $MIC_{50}$ values of TIC844_8 compared to the scaffold protein TIC844 for two different CEW colonies, Union City and Benzon. The bioassay results depicted in FIG. 1 were calculated from sucrose gradient-purified bioassay preparations. The reason these secondary bioassays were run with sucrose gradient-purified preparation of the proteins opposed to spore-crystal preparations of the proteins was to ensure that the improved activity of TIC844_8 persisted with more extensive purification. Further, the Union City colony was tested to confirm the improved activity observed on the Benzon colony. As demonstrated in FIG. 1, the mutations in three residues for TIC844_8 (S282V_Y316S_I368P), imparted an 8-fold improvement in CEW lethality, relative to TIC844, for the Union City colony and a 50-fold improvement in CEW lethality, relative to TIC844, for the Benzon colony.

Even further demonstrating enhanced Lepidopteran inhibitory spectrum and improved Lepidopteran inhibitory activity of the engineered insecticidal proteins, the insect activity profiles for TIC844 and TIC844_8 from diet bioassay studies, conducted against a broad spectrum of Lepidopteran insect species, are shown in Table 3. The insects tested against in the bioassay studies in Table 3 include black cutworm (BCW, *Agrotis ipsilon*), corn earworm (CEW, *Helicoverpa zea*), fall armyworm (FAW, *Spodoptera frugiperda*), southern armyworm (SAW, *Spodoptera eridiania*), cabbage looper (CLW, *Trichoplusia ni*), European corn borer (ECB, *Ostrinia nubilalis*), southwestern corn borer (SWC, *Diatraea grandiosella*), tobacco budworm (TBW, *Heliothis virescens*), velvetbean caterpillars (VBC, *Anticarsia gemmatalis*), soybean looper (SBL, *Chrysodeixis includes*), and sugarcane borer (SCB, *Diatraea saccharalis*). This Table 3 demonstrates the enhanced Lepidopteran inhibitory spectrum of TIC844_8 compared to the parent scaffold protein TIC844, specifically with improved activity against CEW and VBC.

Example 4

Synthesis of Genes Encoding Engineered Insecticidal Proteins and

TABLE 5-continued

Polynucleotide Sequences Designed for Use in Plants Encoding Scaffold and Engineered Insecticidal Proteins.

| NUCLEOTIDE SEQ ID NO. | PROTEIN | VARIANT |
|---|---|---|
| 39 | Cry1Da1_7.nno | Cry1Da1 + S282V_Y316S_I368P + A2 |
| 41 | TIC844_9.nno | TIC844 + A2 |
| 43 | TIC844_11.nno | TIC844 + S282V_Y316S_I368P + A2 |

**Variant designation "A2" indicates insertion of an alanine residue at amino acid position 2 compared to the native sequence for cloning purposes into plant expression vectors.

Example 5

Expression Cassettes for Expression of Engineered Insecticidal Proteins in Plants This Example illustrates the construction of expression cassettes comprising polynucleotide sequences designed for use in plants which encode scaffold and engineered insecticidal proteins.

A variety of plant expression cassettes were constructed with the polynucleotide sequences encoding scaffold and engineered insecticidal proteins designed for plant expression provided in Table 5. Such expression cassettes are useful for transient expression in plant protoplasts or transformation of plant cells. Typical expression cassettes were designed with respect to the eventual placement of the protein within the cell. One set of expression cassettes was designed in a manner to allow the protein to be translated and remain in the cytosol. Another set of expression cassettes was designed to have a transit peptide contiguous with the toxin protein to allow targeting to an organelle of the cell such as the chloroplast or plastid. All expression cassettes were designed to begin at the 5' end with a promoter, which can be comprised of multiple promoter elements, enhancer elements, or other expression elements known to those of ordinary skill in the art operably linked to boost the expression of the transgene. The promoter sequence was usually followed contiguously with one or more leader sequences 3' to the promoter. An intron sequence was usually provided 3' to the leader sequence to improve expression of the transgene. A coding sequence for the toxin or transit peptide and coding sequence for the toxin was usually located 3' to the operably linked promoter, leader and intron configuration. A 3'UTR sequence was usually provided 3' of the coding sequence to facilitate termination of transcription and to provide sequences important for the polyadenylation of the resulting transcript. All of the elements described above were operably linked and arranged sequentially, often with additional sequences provided for the construction of the expression cassette.

Example 6

Transformation Vectors Containing a Scaffold or Engineered Insecticidal Protein Expression Cassette This Example illustrates the incorporation of scaffold or engineered insecticidal proteins into plant tissues.

Methods for producing a transgenic plant which expresses a nucleic acid segment encoding a scaffold protein or an engineered insecticidal protein can be done utilizing variations of methods well known in the art. In general, the method comprises transforming a suitable host cell with a DNA segment which contains a promoter operatively linked to a coding region that encodes one or more of the engineered insecticidal proteins or scaffold proteins. Such a coding region is generally operatively linked to a transcription-terminating region, whereby the promoter is capable of driving the transcription of the coding region in the cell, and hence providing the cell the ability to produce the polypeptide in vivo. Vectors, plasmids, cosmids, and DNA segments for use in transforming such cells will generally comprise operons, genes, or gene-derived sequences, either native or synthetically-derived, and particularly those encoding the disclosed engineered insecticidal proteins. These DNA constructs can further include structures such as promoters, enhancers, polylinkers, or other gene sequences which can have regulating activity upon the particular genes of interest. The resultant transgenic plant, plant parts and plant cells are tested for the expression and bioactivity of the encoded protein.

Examples of methods which can be modified for obtaining transgenic plants that express Lepidopteran-active proteins include those describing, for example, Cry1A proteins (U.S. Pat. No. 5,880,275), Cry1B (U.S. patent application Ser. No. 10/525,318), Cry1C (U.S. Pat. No. 6,033,874), Cry1A/F chimeras (U.S. Pat. Nos. 7,070,982; 6,962,705, and 6,713,063), and a Cry2Ab protein (U.S. Pat. No. 7,064,249).

Example 7

Lepidopteran Activity of Engineered Insecticidal Proteins in Stably Transformed Corn This Example illustrates the inhibitory activity exhibited by the engineered insecticidal proteins against Lepidopteran pests when expressed in corn plants and provided as a diet to the respective insect pest.

R0 transgenic corn plants expressing Cry1Da1 and Cry1Da1_7.nno proteins were produced using vectors containing the expression cassettes described in Example 6. F1 transgenic corn plants were grown from seed produced by pollinating ears of non-transformed wild-type commercial germplasm plants with pollen from R0 transformants.

The transformed cells were induced to form plants by methods known in the art. Bioassays using plant leaf disks were performed analogous to those described in U.S. Pat. No. 8,344,207. A non-transformed plant was used to obtain tissue for a negative control. Multiple transformation events from each binary vector were assessed, and the results were tabulated.

The insecticidal activity of transgenic corn plants expressing Cry1Da1 and Cry1Da1_7.nno proteins at F1 and R0 is provided in Table 6, in addition to activity against transgenic corn plants expressing Cry1Da1 and Cry1Da1_7.nno proteins at F1 in the field. Specifically, Table 6 demonstrates the Lepidopteran activity profile for Cry1Da1_7.nno compared to the parent scaffold protein Cry1Da1 when tested against CEW, FAW, and SWC. As can be seen in Table 6, unlike Cry1Da1, Cry1Da1_7.nno demonstrates activity against both CEW and FAW in R0 and F1 bioassay and F1 field tests.

TABLE 6

Insect activity profile for Cry1Da1 and Cry1Da1_7.nno expressed in corn plants.

| Protein (SEQ ID NO.) | CEW | | | FAW | | | SWC | | |
|---|---|---|---|---|---|---|---|---|---|
| | R0 | F1 | Field | R0 | F1 | Field | R0 | F1 | Field |
| Cry1Da1 (28) | − | NT | NT | + | NT | NT | − | NT | NT |
| Cry1Da1_7.nno (40) | + | + | + | + | + | + | − | − | − |

+ Active against insect species;
− Inactive against insect species;
NT Not Tested

Example 8

Lepidopteran Activity of Engineered Insecticidal Proteins in Stably Transformed Cotton This Example illustrates the inhibitory activity exhibited by the engineered insecticidal proteins against Lepidopteran pests when expressed in cotton plants and provided as a diet to the respective insect pest.

Cotton plants expressing Cry1Da1_7.nno and TIC844_11.nno proteins were produced using vectors containing the expression cassettes described in Example 6. The transformed cells were induced to form plants by methods known in the art. Cotton leaf tissue was used in bioassay as described in Example 7 and tested against CBW, FAW, Tobacco budworm (TBW, *Heliothis virescens*), and SBL. Table 7 shows the activity observed against these Lepidopteran species in stably transformed $R_0$ generation cotton. As can be seen in Table 7, Cry1Da1_7.nno and TIC844_11.nno demonstrated activity against two or more Lepidopteran pest species in stably transformed $R_0$ generation cotton.

TABLE 7

Bioassay activity profile of Cry1Da1_7.nno, and TIC844_11.nno expressed in $R_0$ generation cotton.

| Toxin | CBW | FAW | TBW | SBL |
|---|---|---|---|---|
| Cry1Da1_7.nno (SEQ ID NO: 40) | + | + | + | + |
| TIC844_11.nno (SEQ ID NO: 44) | + | + | − | + |

+ Active against insect species; − Inactive against insect species.

Selected transformed events were used to produce $R_1$ plants. $R_1$ plants expressing Cry1Da1_7.nno were assayed for resistance to CBW, FAW and SBL. Leaf, square and boll tissues were used in bioassay, in addition to field tests conducted in screenhouses. Table 8 shows the activity observed in these tests. As demonstrated in Table 8, Cry1Da1_7.nno demonstrated activity against CBW, FAW and SBL in bioassay and field tests.

TABLE 8

Insect activity profile of Cry1Da1_7.nno expressed in $R_1$ generation cotton.

| Toxin | CBW | | | FAW | | | SBL | Screenhouse | |
|---|---|---|---|---|---|---|---|---|---|
| | Leaf | Square | Boll | Leaf | Square | Boll | Leaf | CBW | FAW |
| Cry1Da1_7.nno (SEQ ID NO: 40) | + | + | + | + | + | + | + | + | + |

+ Active against insect species;
− Inactive against insect species.

Example 9

Lepidopteran Activity of Engineered Insecticidal Proteins in Stably Transformed Soybean This Example illustrates the inhibitory activity exhibited by the engineered insecticidal proteins against Lepidopteran pests when expressed in soybean plants and provided as a diet to the respective insect pest.

Soybean plants expressing Cry1Da1_7.nno, TIC844_9.nno and TIC844_11.nno proteins were produced using vectors containing the expression cassettes described in Example 6. Leaf tissue was harvested and used in bioassay as described in Example 7 or, alternatively, lyophilized tissue was used in the insect diet for bioassay. Bioassay was performed against various Lepidopteran species, including SAW, SBL and Soybean Pod Worm (SPW, *Helicoverpa zea*). Table 9 shows the activity observed against these Lepidopteran pests in stably transformed R0 generation soybeans. As can be seen in Table 9, Cry1Da1_7.nno and TIC844_11.nno demonstrated activity against SPW, SAW and SBL. TIC844_9.nno (TIC844 plus a bonus alanine for cloning) did not demonstrate activity against SPW.

TABLE 9

Bioassay activity profile of Cry1Da1_7.nno, TIC844_9.nno and TIC844_11.nno expressed in R₀ generation soybean.

| Toxin | SPW | SAW | SBL |
|---|---|---|---|
| Cry1Da1_7.nno (SEQ ID NO: 40) | + | + | + |
| TIC844_11.nno (SEQ ID NO: 44) | + | + | + |
| TIC844_9.nno (SEQ ID NO: 42) | − | + | + |

+ Active against insect species; − Inactive against insect species.

Selected transformed events were used to produce $R_1$ plants. $R_1$ plants expressing Cry1Da1_7.nno were assayed for resistance to SAW, SBL, SPW and Velvetbean caterpillar (VBC, *Anticarsia gemmatalis*). Leaf tissue was harvested from the $R_1$ generation plants and used in a feeding bioassay. Table 10 shows the activity observed in these tests. As demonstrated in Table 10, Cry1Da1_7.nno demonstrated activity against SPW, SAW and SBL.

TABLE 10

Bioassay activity profile of Cry1Da1_7.nno expressed in $R_1$ generation soybean.

| Toxin | SPW | SAW | SBL | VBC |
|---|---|---|---|---|
| Cry1Da1_7.nno (SEQ ID NO: 40) | + | + | + | − |

+ Active against insect species; − Inactive against insect species.

Table 11 shows the results of field tests conducted in screenhouses with stably transformed $R_1$ generation soybean plants expressing Cry1Da1_7.nno. Species used to infest plants in the screenhouses include Black armyworm (BLAW, *Spodoptera cosmioides*), Bean shoot moth (BSM, *Crocidosema aporema*), South American podworm (SAPW, *Helicoverpa gelotopoeon*), Sunflower looper (SFL, *Rachiplusia nu*) and VBC. Table 11 shows the activity observed in these tests. As demonstrated in Table 11, Cry1Da1_7.nno demonstrated activity against BLAW, SAPW and SFL.

TABLE 11

Activity profile of Cry1Da1_7.nno expressed in $R_1$ generation soybean tested in screenhouse field tests.

| Toxin | BLAW | BSM | SAPW | SFL | VBC |
|---|---|---|---|---|---|
| Cry1Da1_7.nno (SEQ ID NO: 40) | + | − | + | + | − |

+ Active against insect species; − Inactive against insect species.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

What is claimed is:

1. An engineered insecticidal protein comprising the amino acid sequence as set forth in SEQ ID NO: 40 or an insect inhibitory fragment thereof, wherein the insect inhibitory fragment comprises domains I, II, and III.

2. The engineered insecticidal protein of claim 1, wherein the engineered insecticidal protein exhibits inhibitory activity against an insect species of the order Lepidoptera.

3. The engineered insecticidal protein of claim 2, wherein the Lepidoptera is selected from the group consisting of a *Spodoptera* and a *Helicoverpa.*

4. The engineered insecticidal protein of claim 2, wherein the Lepidoptera is selected from the group consisting of *Helicoverpa zea* and *Spodoptera frugiperda.*

5. A polynucleotide encoding the engineered insecticidal protein or the insect inhibitory fragment thereof of claim 1, wherein the polynucleotide is operably linked to a heterologous promoter.

6. A polynucleotide comprising a nucleotide sequence that encodes the engineered insecticidal protein or the insect inhibitory fragment thereof of claim 1.

7. A host cell comprising the polynucleotide of claim 6, wherein the host cell is selected from the group consisting of a bacterial host cell or a plant host cell.

8. The host cell of claim 7, wherein the bacterial host cell is selected from the group consisting of *Agrobacterium, Rhizobium, Bacillus, Brevibacillus, Escherichia, Pseudomonas, Klebsiella*, and *Erwinia.*

9. The host cell of claim 7, wherein the plant host cell is selected from the group of plants consisting of monocot plant cell and dicot plant cell.

10. An insect inhibitory composition comprising the engineered insecticidal protein or the insect inhibitory fragment thereof of claim 1, wherein said engineered insecticidal protein or the insect inhibitory fragment thereof is present in an insect inhibitory amount.

11. The insect inhibitory composition of claim 10, wherein said composition further comprises a second insect inhibitory agent different from the engineered insecticidal protein.

12. The insect inhibitory composition of claim 11, wherein said second insect inhibitory agent is selected from the group consisting of an insect inhibitory protein and an insect inhibitory dsRNA molecule.

13. The insect inhibitory composition of claim 12, wherein said second insect inhibitory agent exhibits activity against one or more pest species selected from the group of the orders consisting of Lepidoptera, Coleoptera, Hemiptera, Homoptera, and Thysanoptera.

14. A seed comprising the polynucleotide of claim 6, wherein said polynucleotide is operably linked to a heterologous promoter.

15. A method of controlling a Lepidopteran pest, the method comprising contacting the Lepidopteran pest with an insect inhibitory amount of the engineered insecticidal protein or the insect inhibitory fragment thereof of claim 1.

16. A transgenic plant cell, plant or plant part comprising the engineered insecticidal protein or the insect inhibitory fragment thereof of claim 1.

17. A method of controlling a Lepidopteran pest, comprising exposing the pest to the transgenic plant cell, plant or plant part of claim 16, wherein said plant cell, plant or plant part expresses a Lepidopteran inhibitory amount of the engineered insecticidal protein or the insect inhibitory fragment thereof.

18. A commodity product derived from the plant cell, plant, or plant part of claim 16, wherein the product comprises a detectable amount of the engineered insecticidal protein or the insect inhibitory fragment thereof.

19. The commodity product of claim 18, wherein the commodity product is selected from the group consisting of plant biomass, oil, meal, animal feed, flour, flakes, bran, lint, hulls, and processed seed.

20. A method of producing a seed comprising the engineered insecticidal protein or the insect inhibitory fragment thereof of claim 1, the method comprising:

a. planting at least one seed comprising the engineered insecticidal protein or the insect inhibitory fragment thereof;
b. growing plants from said seed; and
c. harvesting seed from said plants, wherein said harvested seed comprises the engineered insecticidal protein or the insect inhibitory fragment thereof.

21. The engineered insecticidal protein or the insect inhibitory fragment thereof of claim 1, wherein the insect inhibitory fragment is a C-terminal truncation of the engineered insecticidal protein that retains the insect inhibitory activity of the engineered insecticidal protein.

* * * * *

SEQUENCE LISTING

```
Sequence total quantity: 44
SEQ ID NO: 1            moltype = DNA  length = 3498
FEATURE                 Location/Qualifiers
misc_feature            1..3498
                        note = Nucleotide sequence used for expression in a
                        bacterial cellencoding Cry1Da1.
source                  1..3498
                        mol_type = other DNA
                        organism = Bacillus thuringiensis
SEQUENCE: 1
atggaaataa ataatcaaaa ccaatgtgtg ccttacaatt gtttaagtaa tcctaaggag   60
ataatattag gcgaggaaag gctagaaaca gggaatactg tagcagacat ttcattaggg  120
cttattaatt ttctatattc taattttgta ccaggaggag gatttatagt aggtttacta  180
gaattaatat ggggatttat agggccttcg caatgggata ttttttttagc tcaaattgag  240
caattgatta gtcaaagaat agaagaattt gctaggaatc aggcaatttc aagattggag  300
gggctaagca atctttataa ggtctatgtt agagcgttta gcgactggga gaaagatcct  360
actaatcctg ctttaaggga agaaatgcgt atacaattta atgacatgaa tagtgctctc  420
ataacggcta ttccactttt tagagttcaa aattatgaag ttgctctttt atctgtatat  480
gttcaagccg caaacttaca tttatctatt ttaagggatg tttcagtttt cggagaaaga  540
tgggggatatg atacagcgac tatcaataat cgctatagtg atctgactag ccttattcat  600
gtttatacta accattgtgt ggatacgtat aatcagggat taaggcgttt ggaaggtcgt  660
tttcttagcg attggattgt atataatcgt ttccggagac aattgacaat ttcagtatta  720
gatattgttg cgttttttcc aaattatgat attagaacat atccaattca aacagctact  780
cagctaacga gggaagtcta tctggattta cctttttatta atgaaaatct ttctcctgca  840
gcaagctatc caacctttttc agctgctgaa agtgctataa ttagaagtcc tcatttagta  900
gacttttttaa atagctttac catttataca gatagtctgg cacgttatgc atattgggga  960
gggcacttgg taaattcttt ccgcacagga accactacta atttgataag atcccctttta 1020
tatggaaggg aaggaaatac agagcgcccc gtaactatta ccgcatcacc tagcgtacca 1080
atatttagaa cactttcata tattacaggc cttgacaatt caaatcctgt agctggaatc 1140
gagggagtgg aattccaaaa tactataagt agaagtatct atcgtaaaag cggtccaata 1200
```

-continued gattctttta gtgaattacc acctcaagat gccagcgtat ctcctgcaat tgggtatagt 1260
caccgtttat gccatgcaac atttttagaa cggattagtg gaccaagaat agcaggcacc 1320
gtattttctt ggacacaccg tagtgccagc cctactaacg aagtaagtcc atctagaatt 1380
acacaaattc catgggtaaa ggcgcatact cttgcatctg gtgcctccgt cattaaaggt 1440
cctggattta caggtggaga tattctgact aggaatagta tgggcgagct ggggacctta 1500
cgagtaacct tcacaggaag attaccacaa agttattata tacgtttccg ttatgcttcg 1560
gtagcaaata ggagtggtac atttagatat tcacagccac cttcgtatgg aatttcattt 1620
ccaaaaacta tggacgcagg tgaaccacta acatctcgtt cgttcgctca tacaacactc 1680
ttcactccaa taacctttc acgagctcaa gaagaatttg atctatacat ccaatcgggt 1740
gtttatatag atcgaattga atttataccg gttactgcaa catttgaggc agaatatgat 1800
ttagaaagag cgcaaaaggt ggtgaatgcc ctgtttacgt ctacaaacca actagggcta 1860
aaaacagatg tgacggatta tcatattgat caggtatcca atctagttgc gtgtttatcg 1920
gatgaatttt gtctggatga aaagagagaa ttgtccgaga aagttaaaca tgcaaagcga 1980
ctcagtgatg agcggaattt acttcaagat ccaaacttca gagggatcaa taggcaacca 2040
gaccgtggct ggagaggaag tacggatatt actatccaag gaggagatga cgtattcaaa 2100
gagaattacg ttacgctacc gggtaccttt gatgagtgct atccaacgta tttatatcaa 2160
aaaatagatg agtcgaaatt aaaagcctat acccgttatc aattaagagg gtatatcgaa 2220
gatagtcaag acttagaaat ctatttaatt cgttacaatg caaaacacga aatagtaaat 2280
gtaccaggta caggaagttt atggcctctt tctgtagaaa atcaaattgg accttgtgga 2340
gaaccgaatc gatgcgcgcc acaccttgaa tggaatcctg atttacactg ttcctgcaga 2400
gacggggaaa aatgtgcaca tcattctcat catttctctt tggacattga tgttggatgt 2460
acagacttaa atgaggactt aggtgtatgg gtgatattca agattaagac gcaagatggc 2520
cacgcacgac tagggaatct agagtttctc gaagagaaac cattattagg agaagcacta 2580
gctcgtgtga aaagagcgga gaaaaaatgg agagacaaac gcgaaacatt acaattggaa 2640
acaactatcg tttataaaga ggcaaaagaa tctgtagatg ctttatttgt aaactctcaa 2700
tatgatagat tacaagcgga tacgaacatc gcgatgattc atgcggcaga taaacgcgtt 2760
catagaattc gagaagcgta tctgccggag ctgtctgtga ttccgggtgt caatgcggct 2820
atttttgaag aattagaaga gcgtattttc actgcatttt ccctatatga tgcgagaaat 2880
attattaaaa atggcgattt caataatggc ttattatgct ggaacgtgaa agggcatgta 2940
gaggtagaag aacaaaacaa tcaccgttca gtcctggtta tcccagaatg ggaggcagaa 3000
gtgtcacaag aggttcgtgt ctgtccaggt cgtggctata tccttcgtgt tacagcgtac 3060
aaagagggat atggagaagg ttgcgtaacg atccatgaga tcgagaacaa tacagacgaa 3120
ctgaaattca acaactgtgt agaagaggaa gtatatccaa acaacacggt aacgtgtatt 3180
aattatactg cgactcaaga agaatatgag ggtacgtaca cttctcgtaa tcgaggatat 3240
gacgaagcct atggtaataa cccttccgta ccagctgatt atgcgtcagt ctatgaagaa 3300
aaatcgtata cagatagacg aagagagaat ccttgtgaat ctaacagagg atatggagat 3360
tacacaccac taccagctgg ttatgtaaca aaggaattag agtacttccc agagaccgat 3420
aaggtatgga ttgagattgg agaaacagaa ggaacattca tcgtggacag cgtggaatta 3480
ctccttatgg aggaatag 3498

SEQ ID NO: 2 moltype = AA length = 1165
FEATURE Location/Qualifiers
REGION 1..1165
note = MISC_FEATURE - Amino acid sequence of the protein Cry1Da1.
source 1..1165
mol_type = protein
organism = Bacillus thuringiensis
SEQUENCE: 2
MEINNQNQCV PYNCLSNPKE IILGEERLET GNTVADISLG LINFLYSNFV PGGGFIVGLL 60
ELIWGFIGPS QWDIFLAQIE QLISQRIEEF ARNQAISRLE GLSNLYKVYV RAFSDWEKDP 120
TNPALREEMR IQFNDMNSAL ITAIPLFRVQ NYEVALLSVY VQAANLHLSI LRDVSVFGER 180
WGYDTATINN RYSDLTSLIH VYTNHCVDTY NQGLRRLEGR FLSDWIVYNR FRRQLTISVL 240
DIVAFFPNYD IRTYPIQTAT QLTREVYLDL PFINENLSPA ASYPTFSAAE SAIIRSPHLV 300
DFLNSFTIYT DSLARYAYWG GHLVNSFRTG TTTNLIRSPL YGREGNTERP VTITASPSVP 360
IFRTLSYITG LDNSNPVAGI EGVEFQNTIS RSIYRKSGPI DSFSELPPQD ASVSPAIGYS 420
HRLCHATFLE RISGPRIAGT VFSWTHRSAS PTNEVSPSRI TQIPWVKAHT LASGASVIKG 480
PGFTGGDILT RNSMGELGTL RVTFTGRLPQ SYYIRFRYAS VANRSGTFRY SQPPSYGISF 540
PKTMDAGEPL TSRSFAHTTL FTPITFSRAQ EEFDLYIQSG VYIDRIEFIP VTATFEAEYD 600
LERAQKVVNA LFTSTNQLGL KTDVTDYHID QVSNLVACLS DEFCLDEKRE LSEKVKHAKR 660
LSDERNLLQD PNFRGINRQP DRGWRGSTDI TIQGGDDVFK ENYVTLPGTF DECYPTYLYQ 720
KIDESKLKAY TRYQLRGYIE DSQDLEIYLI RYNAKHEIVN VPGTGSLWPL SVENQIGPCG 780
EPNRCAPHLE WNPDLHCSCR DGEKCAHHSH HFSLDIDVGC TDLNEDLGVW VIFKIKTQDG 840
HARLGNLEFL EEKPLLGEAL ARVKRAEKKW RDKRETLQLE TTIVYKEAKE SVDALFVNSQ 900
YDRLQADTNI AMIHAADKRV HRIREAYLPE LSVIPGVNAA IFEELEERIF TAFSLYDARN 960
IIKNGDFNNG LLCWNVKGHV EVEEQNNHRS VLVIPEWEAE VSQEVRVCPG RGYILRVTAY 1020
KEGYGEGCVT IHEIENNTDE LKFNNCVEEE VYPNNTVTCI NYTATQEEYE GTYTSRNRGY 1080
DEAYGNNPSV PADYASVYEE KSYTDRRREN PCESNRGYGD YTPLPAGYVT KELEYFPETD 1140
KVWIEIGETE GTFIVDSVEL LLMEE 1165

SEQ ID NO: 3 moltype = DNA length = 3498
FEATURE Location/Qualifiers
misc_feature 1..3498
note = Nucleotide sequence used for expression in a bacterial cellencoding Cry1Da1_3.
source 1..3498
mol_type = other DNA
organism = synthetic construct
SEQUENCE: 3

```
atggaaataa ataatcaaaa ccaatgtgtg ccttacaatt gtttaagtaa tcctaaggag    60
ataatattag gcgaggaaag gctagaaaca gggaatactg tagcagacat ttcattaggg   120
cttattaatt ttctatattc taattttgta ccaggaggag gatttatagt aggtttacta   180
gaattaatat ggggatttat agggccttcg caatgggata ttttttttagc tcaaattgag   240
caattgatta gtcaaagaat agaagaattt gctaggaatc aggcaatttc aagattggag   300
gggctaagca atctttataa ggtctatgtt agagcgttta gcgactggga aaagatcct   360
actaatcctg ctttaaggga gaaaatgcgt atacaattta tgacatgaa tagtgctctc   420
ataacggcta ttccactttt tagagttcaa aattatgaag ttgctctttt atctgtatat   480
gttcaagccg caaacttaca tttatctatt ttaagggatg tttcagtttt cggagaaaga   540
tggggatatg atacagcgac tatcaataat cgctatagtg atctgactag ccttattcat   600
gtttatacta accattgtgt ggatacgtat aatcagggat taaggcgttt ggaaggtcgt   660
tttcttagcg attggattgt atataatcgt ttccggagac aattgacaat ttcagtatta   720
gatattgttg cgttttttcc aaaattatgat attagaacat atccaattca aacagctact   780
cagctaacga gggaagtcta tctggattta cctttttata atgaaaatct ttctcctgca   840
gcaagctatc caacctttttc agctgctgaa agtgctataa ttagaagtcc tcatttagta   900
gactttttaa atagctttac catttataca gatagtctgg cacgtagtgc atattgggga   960
gggcacttgg taaattcttt ccgcacagga accactacta atttgataag atcccctta  1020
tatgaaggga aaggaaatac agagcgcccc gtaactatca ccgcatcacc tagcgtacca  1080
atatttagaa cactttccata tattacaggc cttgacaatt caaatcctgt agctggaatc  1140
gagggagtgg aattccaaaa tactataagt agaagtatct atcgtaaaag cggtccaata  1200
gattctttta gtgaattacc acctcaagat gccagctat ctcctgcaat tgggtatagt  1260
caccgtttat gccatgcaac attttttagaa cggattagtg gaccaagaat agcaggcacc  1320
gtattttctt ggacacaccg tagtgccagc cctactaacg aagtaagtcc atctagaatt  1380
acacaaattc catgggtaaa ggcgcatact cttgcatctg gtgcctccgt cattaaaggt  1440
cctgatttta caggtggaga tattctgact aggaatagta tgggcgagct ggggacctta  1500
cgagtaacct tcacaggaag attaccacaa agttattata tacgttttcgg ttatgcttcg  1560
gtagcaaata ggagtggtac atttagatat tcacagccac cttcgtatgg aatttcattt  1620
ccaaaaacta tggacgcagg tgaaccacta acatctcgtt cgttcgctca tacaacactc  1680
ttcactccaa taacctttttc acgagctcaa gaagaatttg atctatacat ccaatcgggt  1740
gtttatatag atcgaattga catttataccg gttactgaaa catttgaggc agaatatgat  1800
ttagaaagag cgcaaaaggt ggtgaatgcc ctgtttacgt ctacaaacca actagggcta  1860
aaaacagatg tgacggatta tcatattgat caggtatcca atctagttgc gtgtttatcg  1920
gatgaattttt gtctgatga aaagagagaa ttgtccgaga aagttaaaca tgcaaagcga  1980
ctcagtgatg agcggaattt acttcaagat ccaaacttca gagggatcaa taggcaacca  2040
gaccgtggct ggagaggaag tacggatatt actatccaag gaggagatga cgtattcaaa  2100
gagaattacg ttacgctacc gggtaccttt gatgagtgct atccaacgta tttatatcaa  2160
aaaatagatg agtcgaaatt aaaagcctat acccgttatc aattaagagg gtatatcgaa  2220
gatagtcaag acttagaaat ctatttaatt cgttacaatg caaaacacga aatagtaaat  2280
gtaccaggta caggaagttt atggcctctt tctgtagaaa atcaaattgg accttgtgga  2340
gaaccgaatc gatgcgcgcc acaccttgaa tggaatcctg atttacactg ttcctgcaga  2400
gacgggaaa atgtgcaca tcattctcat catttctctt tggacattga tgttggatgt  2460
acagacttaa atgaggactt aggtgtatgg gtgatattca agattaagac gcaagatggc  2520
cacgcacgac tagggaatct agagttttctc gaagagaaac cattattagg agaagcacta  2580
gctcgtgtga aaagagcgga gaaaaatgg agagacaaac gcgaaacatt acaattggaa  2640
acaactatcg tttataaaga ggcaaagaaa tctgtagatg ctttatttgt aaaactctcaa  2700
tatgatagat acaagcggga tacgaacatc gcgatgatc atgcggcaga taaacgcgtt  2760
catagaattc gagaagcgta tctgccggag ctgtctgtga ttccgggtgt caatgcggct  2820
attttttgaag aattgaagag gcgtattttc actgtcattt ccctatatga tgcgagaaat  2880
attattaaaa atggcgattt caataatggc ttattatgct ggaacgtgaa agggcatgta  2940
gaggtagaag aacaaaacaa tcaccgttca gtcctggtta tccagaatgg ggaggcagaa  3000
gtgtcacaag aggttcgtgt ctgtccaggt cgtggctata tccttcgtgt tacagcgtac  3060
aaagagggat atggagaagg ttgcgtaacg atccatgaga tcgagaacaa tacagacgaa  3120
ctgaaattca caactgtgt agaagaggaa gtatatccaa acaacacggt aacgtgtatt  3180
aattatactg cgactcaaga gaatatgag ggtacgtaca cttctcgtaa tcgaggatat  3240
gacgaagcct atggtaataa cccttccgta ccagctgatt atgcgtcagat ctatgaagaa  3300
aaatcgtata cagatagacg aagagaagaat ccttgtgaat ctaacagagg atatggagat  3360
tacacaccac taccagctgg ttatgtaaca aaggaattag agtacttccc agagaccgat  3420
aaggtatgga ttgagattgg agaaacagaa ggaacattca tcgtggacag cgtggaatta  3480
ctccttatgg aggaatag                                                3498
```

| SEQ ID NO: 4 | moltype = AA   length = 1165 |
|---|---|
| FEATURE | Location/Qualifiers |
| REGION | 1..1165 |
| | note = Amino acid sequence of the engineered insecticidal proteinCry1Da1_3. |
| source | 1..1165 |
| | mol_type = protein |
| | organism = synthetic construct |

SEQUENCE: 4

```
MEINNQNQCV PYNCLSNPKE IILGEERLET GNTVADISLG LINFLYSNFV PGGGFIVGLL    60
ELIWGFIGPS QWDIFLAQIE QLISQRIEEF ARNQAISRLE GLSNLYKVYV RAFSDWEKDP   120
TNPALREEMR IQFNDMNSAL ITAIPLFRVQ NYEVALLSVY VQAANLHLSI LRDVSVFGER   180
WGYDTATINN RYSDLTSLIH VYTNHCVDTY NQGLRRLEGR FLSDWIVYNR FRRQLTISVL   240
DIVAFFPNYD IRTYPIQTAT QLTREVYLDL PFINENLSPA ASYPTFSAAE SAIIRSPHLV   300
DFLNSFTIYT DSLARSAYWG GHLVNSFRTG TTTNLIRSPL YGREGNTERP VTITASPSVP   360
IFRTLSYITG LDNSNPVAGI EGVEFQNTIS RSIYRKSGPI DSFSELPPQD ASVSPAIGYS   420
HRLCHATFLE RISGPRIAGT VFSWTHRSAS PTNEVSPSRI TQIPWVKAHT LASGASVIKG   480
PGFTGGDILT RNSMGELGTL RVTFTGRLPQ SYYIRFRYAS VANRSGTFRY SQPPSYGISF   540
PKTMDAGEPL TSRSFAHTTL FTPITFSRAQ EEFDLYIQSG VYIDRIEFIP VTATFEAEYD   600
```

-continued

```
LERAQKVVNA LFTSTNQLGL KTDVTDYHID QVSNLVACLS DEFCLDEKRE LSEKVKHAKR  660
LSDERNLLQD PNFRGINRQP DRGWRGSTDI TIQGGDDVFK ENYVTLPGTF DECYPTYLYQ  720
KIDESKLKAY TRYQLRGYIE DSQDLEIYLI RYNAKHEIVN VPGTGSLWPL SVENQIGPCG  780
EPNRCAPHLE WNPDLHCSCR DGEKCAHHSH HFSLDIDVGC TDLNEDLGVW VIFKIKTQDG  840
HARLGNLEFL EEKPLLGEAL ARVKRAEKKW RDKRETLQLE TTIVYKEAKE SVDALFVNSQ  900
YDRLQADTNI AMIHAADKRV HRIREAYLPE LSVIPGVNAA IFEELEERIF TAFSLYDARN  960
IIKNGDFNNG LLCWNVKGHV EVEEQNNHRS VLVIPEWEAE VSQEVRVCPG RGYILRVTAY  1020
KEGYGEGCVT IHEIENNTDE LKFNNCVEEE VYPNNTVTCI NYTATQEEYE GTYTSRNRGY  1080
DEAYGNNPSV PADYASVYEE KSYTDRRREN PCESNRGYGD YTPLPAGYVT KELEYFPETD  1140
KVWIEIGETE GTFIVDSVEL LLMEE                                        1165

SEQ ID NO: 5            moltype = DNA  length = 3498
FEATURE                 Location/Qualifiers
misc_feature            1..3498
                        note = Nucleotide sequence used for expression in a
                         bacterial cellencoding Cry1Da1_4.
source                  1..3498
                        mol_type = other DNA
                        organism = synthetic construct
SEQUENCE: 5
atggaaataa ataatcaaaa ccaatgtgtg ccttacaatt gtttaagtaa tcctaaggag  60
ataatattag gcgaggaaag gctagaaaca gggaatactg tagcagacat ttcattaggg  120
cttattaatt ttctatattc taattttgta ccaggaggag gatttatagt aggtttacta  180
gaattaatat ggggatttat agggccttcg caatgggata tttttttagc tcaaattgag  240
caattgatta gtcaaagaat agaagaattt gctaggaatc aggcaatttc aagattggag  300
gggctaagca atctttataa ggtctatgtt agagcgttta gcgactggga gaaagatcct  360
actaatcctg ctttaaggga agaaatgcgt atacaattta atgacatgaa tagtgctctc  420
ataacggcta ttccactttt tagagttcaa aattatgaag ttgctctttt atctgtatat  480
gttcaagccg caaacttaca tttatctatt ttaagggatg tttcagtttt cggagaaaga  540
tggggatatg atacagcgac tatcaataat cgctatagtg atctgactag ccttattcat  600
gtttatacta accattgtgt ggatacgtat aatcagggat taaggcgttt ggaaggtcgt  660
tttcttagcg attggattgt atataatcgt ttccggagac aattgacaat ttcagtatta  720
gatattgttg cgtttttcc aaattatgat attagaacat atccaattca aacagctact  780
cagctaacga gggaagtcta tctggattta ccttttatta atgaaaatct ttctcctgca  840
gcaagctatc caacctttc agctgctgaa agtgctataa ttagaagtcc tcatttagta  900
gactttttaa atagctttac catttataca gatagtctgg cacgttatgc atattgggga  960
gggcacttgg taaattcttt ccgcacagga accactacta atttgataag atccccttta  1020
tatggaaggg aaggaaatac agagcgcccc gtaactatta ccgcatcacc tagcgtacca  1080
atatttagaa cactttcata tattacaggc cttgacaatc gtaatcctgt agctggaatc  1140
gagggagtgg aattccaaaa tactataagt agaagtatct atcgtaaaag cggtccaata  1200
gattctttta gtgaattacc acctcaagat gccagcgtat ctcctgcaat tgggtatagt  1260
caccgtttat gccatgcaac atttttagaa cggattagtg gaccaagaat agcaggcacc  1320
gtattttctt ggacacaccg tagtgccagc cctactaacg aagtaagtcc atctagaatt  1380
acacaaattc catgggtaaa ggcgcatact cttgcatctg gtgcctccgt cattaaaggt  1440
cctggattta caggtggaga tattctgact aggaatagta tgggcgagct ggggacctta  1500
cgagtaacct tcacaggaag attaccacaa agttattata tacgtttccg ttatgcttcg  1560
gtagcaaata ggagtggtac atttagatat tcacagccac cttcgtatgg aatttcattt  1620
ccaaaaacta tggacgcagg tgaaccacta acatctcgtt cgttcgctca tacaacactc  1680
ttcactccaa taacctttc acgagctcaa gaagaatttg atctatacat ccaatcgggt  1740
gtttatatag atcgaattga atttataccg gttactgcaa catttgaggc agaatatgat  1800
ttagaaagag cgcaaaaggt ggtgaatgcc ctgtttacgt ctacaaacca actagggcta  1860
aaaacagatg tgacggatta tcatattgat caggtatcca atctagttgc gtgtttatcg  1920
gatgaatttt gtctggatga aaagagagaa ttgtccgaga aagttaaaca tgcaaagcga  1980
ctcagtgatg agcggaattt acttcaagat ccaaacttca gagggatcaa taggcaacca  2040
gaccgtggct ggagaggaag tacggatatt actatccaag gaggagatga cgtattcaaa  2100
gagaattacg ttacgctacc gggtaccttt gatgagtgct atccaacgta tttatatcaa  2160
aaaatagatg agtcgaaatt aaaagcctat acccgttatc aattaagagg gtatatcgaa  2220
gatagtcaag acttagaaat ctatttaatt cgttacaatg caaaacacga aatagtaaat  2280
gtaccaggta caggaagttt atggcctctt tctgtagaaa atcaaattgg accttgtgga  2340
gaaccgaatc gatgcgcgcc acaccttgaa tggaatcctg atttacactg ttcctgcaga  2400
gacggggaaa aatgtgcaca tcattctcat catttctctt tggacattga tgttggatgt  2460
acagacttaa atgaggactt aggtgtatgg gtgatattca agattaagac gcaagatggc  2520
cacgcacgac tagggaatct agagtttctc gaagagaaac cattattagg agaagcacta  2580
gctcgtgtga aaagagcgga gaaaaaatgg agagacaaac gcgaaacatt acaattggaa  2640
acaactatcg tttataaaga ggcaaaagaa tctgtagatg ctttatttgt aaactctcaa  2700
tatgatagat tacaagcgga tacgaacatc gcgatgattc atgcggcaga taaacgcgtt  2760
catagaattc gagaagcgta tctgccggag ctgtctgtga ttccgggtgt caatgcggct  2820
atttttgaag aattagaaga gcgtattttc actgcatttt ccctatatga tgcgagaaat  2880
attattaaaa atggcgattt caataatggc ttattatgct ggaacgtgaa agggcatgta  2940
gaggtagaag aacaaaacaa tcaccgttca gtcctggtta tcccagaatg ggaggcagaa  3000
gtgtcacaag aggttcgtgt ctgtccaggt cgtggctata tccttcgtgt tacagcgtac  3060
aaagagggat atggagaagg ttgcgtaacg atccatgaga tcgagaacaa tacagacgaa  3120
ctgaaattca acaactgtgt agaagaggaa gtatatccaa acaacacggt aacgtgtatt  3180
aattatactg cgactcaaga agaatatgag ggtacgtaca cttctcgtaa tcgaggatat  3240
gacgaagcct atggtaataa cccttccgta ccagctgatt atgcgtcagt ctatgaagaa  3300
aaatcgtata cagatagacg aagagagaat ccttgtgaat ctaacagagg atatggagat  3360
tacacaccac taccagctgg ttatgtaaca aaggaattag agtacttccc agagaccgat  3420
aaggtatgga ttgagattgg agaaacagaa ggaacattca tcgtggacag cgtggaatta  3480
ctccttatgg aggaatag                                                3498
```

-continued

```
SEQ ID NO: 6            moltype = AA   length = 1165
FEATURE                 Location/Qualifiers
REGION                  1..1165
                        note = Amino acid sequence of the engineered insecticidal
                         proteinCry1Da1_4.
source                  1..1165
                        mol_type = protein
                        organism = synthetic construct
SEQUENCE: 6
MEINNQNQCV PYNCLSNPKE IILGEERLET GNTVADISLG LINFLYSNFV PGGGFIVGLL    60
ELIWGFIGPS QWDIFLAQIE QLISQRIEEF ARNQAISRLE GLSNLYKVYV RAFSDWEKDP   120
TNPALREEMR IQFNDMNSAL ITAIPLFRVQ NYEVALLSVY VQAANLHLSI LRDVSVFGER   180
WGYDTATINN RYSDLTSLIH VYTNHCVDTY NQGLRRLEGR FLSDWIVYNR FRRQLTISVL   240
DIVAFFPNYD IRTYPIQTAT QLTREVYLDL PFINENLSPA ASYPTFSAAE SAIIRSPHLV   300
DFLNSFTIYT DSLARYAYWG GHLVNSFRTG TTTNLIRSPL YGREGNTERP VTITASPSVP   360
IFRTLSYITG LDNRNPVAGI EGVEFQNTIS RSIYRKSGPI DSFSELPPQD ASVSPAIGYS   420
HRLCHATFLE RISGPRIAGT VFSWTHRSAS PTNEVSPSRI TQIPWVKAHT LASGASVIKG   480
PGFTGGDILT RNSMGELGTL RVTFTGRLPQ SYYIRFRYAS VANRSGTFRY SQPPSYGISF   540
PKTMDAGEPL TSRSFAHTTL FTPITFSRAQ EEFDLYIQSG VYIDRIEFIP VTATFEAEYD   600
LERAQKVVNA LFTSTNQLGL KTDVTDYHID QVSNLVACLS DEFCLDEKRE LSEKVKHAKR   660
LSDERNLLQD PNFRGINRQP DRGWRGSTDI TIQGGDIVFK ENYVTLPGTF DECYPTYLYQ   720
KIDESKLKAY TRYQLRGYIE DSQDLEIYLI RYNAKHEIVN VPGTGSLWPL SVENQIGPCG   780
EPNRCAPHLE WNPDLHCSCR DGEKCAHHSH HFSLDIDVGC TDLNEDLGVW VIFKIKTQDG   840
HARLGNLEFL EEKPLLGEAL ARVKRAEKKW RDKRETLQLE TTIVYKEAKE SVDALFVNSQ   900
YDRLQADTNI AMIHAADKRV HRIREAYLPE LSVIPGVNAA IFEELEERIF TAFSLYDARN   960
IIKNGDFNNG LLCWNVKGHV EVEEQNNHRS VLVIPEWEAE VSQEVRVCPG RGYILRVTAY  1020
KEGYGEGCVT IHEIENNTDE LKFNNCVEEE VYPNNTVTCI NYTATQEEYE GTYTSRNRGY  1080
DEAYGNNPSV PADYASVYEE KSYTDRRREN PCESNRGYGD YTPLPAGYVT KELEYFPETD  1140
KVWIEIGETE GTFIVDSVEL LLMEE                                        1165

SEQ ID NO: 7            moltype = DNA   length = 3498
FEATURE                 Location/Qualifiers
misc_feature            1..3498
                        note = Nucleotide sequence used for expression in a
                         bacterial cellencoding Cry1Da1_5.
source                  1..3498
                        mol_type = other DNA
                        organism = synthetic construct
SEQUENCE: 7
atggaaataa ataatcaaaa ccaatgtgtg cctacaatt gtttaagtaa tcctaaggag     60
ataatattag gcgaggaaag gctagaaaca gggaatactg tagcagacat ttcattaggg   120
cttattaatt ttctatattc taatttttgta ccaggaggga gatttatagt aggtttacta   180
gaattaatat ggggatttat agggccttcg caatgggata ttttttttagc tcaaattgag   240
caattgatta gtcaaagaat agaagaattt gctaggaatc aggcaatttc aagattggag   300
gggctaagca atctttataa ggtctatgtt agagcgttta gcgactggga gaaagatcct   360
actaatcctg ctttaaggga agaaatgcgt atacaattta atgacatgaa tagtgctctc   420
ataacggcta ttccactttt tagagttcaa aattatgaag ttgctctttt atctgtatat   480
gttcaagccg caaacttaca tttatctatt ttaagggatg tttcagtttt cggagaaaga   540
tggggatatg atacagcgac tatcaataat cgctatagtg atctgactag ccttattcat   600
gtttatacta accattgtgt ggatacgtat aatcagggat taaggcgttt ggaaggtcgt   660
tttcttagcg attggattgt atataatcgt ttccggagac aattgacaat ttcagtatta   720
gatattgttg cgtttttttcc aaattatgat attagaacat atccaattca aacagctact   780
cagctaacga gggaagtcta tctggattta cctttatta tgaaaatct ttctcctgca    840
gcaagctatc caacctttc agctgctgaa agtgctataa ttagaagtcc tcatttagta   900
gactttttaa atagctttac catttataca gatagtctgg cacgttctgc atattgggga   960
gggcacttgg taaattcttt ccgcacagga accactacta atttgataag atccccctta  1020
tatgaaggga aggaaaatac agagcgcccc gtaactatta ccgcatcacc tagcgtacca  1080
atatttagaa cactttcata tagaacaggc cttgacaatt caaatcctgt agctggaatc  1140
gagggagtgg aattccaaaa tactataagt agaagtatct atcgtaaaag cggtccaata  1200
gattctttta gtgaattacc acctcaagat gccagcgtat ctcctgcaat ggggtatagt  1260
caccgtttat gccatgcaac attttagaa cggattagtg gaccaagaat agcaggcacc   1320
gtattttctt ggacacaccg tagtgccagc cctactaacg aagtaagtcc atctagaatt  1380
acacaaattc catgggtaaa ggcgcatact cttgcatctg gtgcctccgt cattaaaggt  1440
cctggattta caggtggaga tattctgact aggaataca tgggcgagct ggggacctta   1500
cgagtaacct tcacaggaag attaccacaa agttattata tacgtttccg ttatgcttcg  1560
gtagcaaata ggagtggtac atttagatat tcacagccac cttcgtatgg aatttcattt  1620
ccaaaaacta tggacgcagg tgaaccacta acatctcgtt cgttcgctca tacaacactc  1680
ttcactccaa taccctttc acgagctcaa gaagaatttg atctatacat ccaatcgggt  1740
gtttatatag atcgaattga atttatacc gttactgcaa catttgaggc agaatatgat   1800
ttagaaagag cgcaaaaggt ggtgaatgcc ctgtttacgt ctacaaacca actagggcta  1860
aaaacagatg tgacggatta tcatattgat caggtatcca atctagttgc gtgtttatcg  1920
gatgaatttt gtctggatga aaagagagaa ttgtccgaga agtttaaaca tgcaaagcga  1980
ctcagtgatg agcggaattt acttcaagat ccaaacttca ggaacaacca              2040
gaccgtggct ggagaggaag tacggatatt actatccaag gaggagatga cgtattcaaa  2100
gagaattacg ttacgctacc gggtaccttt gatgagtgct atccaacgta tttatatcaa  2160
aaaatagatg agtcgaaatt aaaagcctat acccgttatc aattaagagg gtatatcgaa  2220
gatagtcaag acttagaaat ctatttaatt cgttacaatg caaacacga aatagtaaat   2280
gtaccaggta caggaagttt atggcctctt tctgtagaaa atcaaattgg accttgtgga  2340
```

-continued

```
gaaccgaatc gatgcgcgcc acaccttgaa tggaatcctg atttacactg ttcctgcaga    2400
gacgggaaa  aatgtgcaca tcattctcat catttctctt tggacattga tgttggatgt    2460
acagacttaa atgaggactt aggtgtatgg gtgatattca agattaagac gcaagatggc    2520
cacgcacgac tagggaatct agagtttctc gaagagaaac cattattagg agaagcacta    2580
gctcgtgtga aaagagcgga gaaaaatgg  agagacaaca gcgaaacatt acaattggaa    2640
acaactatcg tttataaaga ggcaaaagaa tctgtagatg ctttatttgt aaactctcaa    2700
tatgatagat tacaagcgga tacgaacatc gcgatgattc atgcggcaga taaacgcgtt    2760
catagaattc gagaagcgta tctgccggag ctgtctgtga ttccgggtgt caatgcggct    2820
attttgaag  aattagaaga gcgtattttc actgcatttt ccctatatga tgcgagaaat    2880
attattaaaa atggcgattt caataatggc ttattatgct ggaacgtgaa agggcatgta    2940
gaggtagaag aacaaaacaa tcaccgttca gtcctggtta tcccagaatg ggaggcagaa    3000
gtgtcacaag aggttcgtgt ctgtccaggt cgtggctata tccttcgtgt tacagcgtac    3060
aaagagggat atggagaagg ttgcgtaacg atccatgaga tcgaacaca  tacagacgaa    3120
ctgaaattca acaactgtgt agaagaggaa gtatatccaa acaacacggt aacgtgtatt    3180
aattatactg cgactcaaga agaatatgag ggtacgtaca cttctcgtaa tcgaggatat    3240
gacgaagcct atggtaataa cccttccgta ccagctgatt atgcgtcagt ctatgaagaa    3300
aaatcgtata cagatagacg aagagagaat ccttgtgaat ctaacagagg atatggagat    3360
tacacaccac taccagctgg ttatgtaaca aaggaattag agtacttccc agagaccgat    3420
aaggtatgga ttgagattgg agaaacagaa ggaacattca tcgtggacag cgtggaatta    3480
ctccttatgg aggaatag                                                  3498

SEQ ID NO: 8           moltype = AA   length = 1165
FEATURE                Location/Qualifiers
REGION                 1..1165
                       note = Amino acid sequence of the engineered insecticidal
                         proteinCry1Da1_5.
source                 1..1165
                       mol_type = protein
                       organism = synthetic construct
SEQUENCE: 8
MEINNQNQCV PYNCLSNPKE IILGEERLET GNTVADISLG LINFLYSNFV PGGGFIVGLL     60
ELIWGFIGPS QWDIFLAQIE QLISQRIEEF ARNQAISRLE GLSNLYKVYV RAFSDWEKDP    120
TNPALREEMR IQFNDMNSAL ITAIPLFRVQ NYEVALLSVY VQAANLHLSI LRDVSVFGER    180
WGYDTATINN RYSDLTSLIH VYTNHCVDTY NQGLRRLEGR FLSDWIVYNR FRRQLTISVL    240
DIVAFFPNYD IRTYPIQTAT QLTREVYLDL PFINENLSPA ASYPTFSAAE SAIIRSPHLV    300
DFLNSFTIYT DSLARSAYWG GHLVNSFRTG TTTNLIRSPL YGREGNTERP VTITASPSVP    360
IFRTLSYRTG LDNSNPVAGI EGVEFQNTIS RSIYRKSGPI DSFSELPPQD ASVSPAIGYS    420
HRLCHATFLE RISGPRIAGT VFSWTHRSAS PTNEVSPSRI TQIPWVKAHT LASGASVIKG    480
PGFTGGDILT RNSMGELGTL RVTFTGRLPQ SYYIRFRYAS VANRSGTFRY SQPPSYGISF    540
PKTMDAGEPL TSRSFAHTTL FTPITFSRAQ EEFDLYIQSG VYIDRIEFIP VTATFEAEYD    600
LERAQKVVNA LFTSTNQLGL KTDVTDYHID QVSNLVACLS DEFCLDEKRE LSEKVKHAKR    660
LSDERNLLQD PNFRGINRQP DRGWRGSTDI TIQGGDDVFK ENYVLPGTF  DECYPTYLYQ    720
KIDESKLKAY TRYQLRGYIE DSQDLEIYLI RYNAKHEIVN VPGTGSLWPL SVENQIGPCG    780
EPNRCAPHLE WNPDLHCSCR DGEKCAHHSH HFSLDIDVGC TDLNEDLGVW VIFKIKTQDG    840
HARLGNLEFL EEKPLLGEAL ARVKRAEKKW RDKRETLQLE TTIVYKEAKE SVDALFVNSQ    900
YDRLQADTNI AMIHAADKRV HRIREAYLPE LSVIPGVNAA IFEELEERIF TAFSLYDARN    960
IIKNGDFNNG LLCWNVKGHV EVEEQNNHRS VLVIPEWEAE VSQEVRVCPG RGYILRVTAY   1020
KEGYGEGCVT IHEIENNTDE LKFNNCVEEE VYPNNTVTCI NYTATQEEYE GTYTSRNRGY   1080
DEAYGNNPSV PADYASVYEE KSYTDRRREN PCESNRGYGD YTPLPAGYVT KELEYFPETD   1140
KVWIEIGETE GTFIVDSVEL LLMEE                                         1165

SEQ ID NO: 9           moltype = DNA   length = 3498
FEATURE                Location/Qualifiers
misc_feature           1..3498
                       note = Nucleotide sequence used for expression in a
                         bacterial cellencoding Cry1Da1_6.
source                 1..3498
                       mol_type = other DNA
                       organism = synthetic construct
SEQUENCE: 9
atggaaataa ataatcaaaa ccaatgtgtg cctacaatt  gtttaagtaa tcctaaggag     60
ataatattag gcgaggaaag gctagaaaca gggaatactg tagcagacat ttcattaggg    120
cttattaatt ttctatattc taattttgta ccaggaggag gatttatagt aggtttacta    180
gaattaatat ggggatttat agggccttcg caatggatta tttttttagc tcaaattgag    240
caattgatta gtcaaagaat agaagaattt gctaggaatc aggcaatttc aagattggag    300
gggctaagca atctttataa ggtctatgtt agagcgttta gcgactggga aaagatcct     360
actaatcctg ctcttaaggga gaaatgcgt atacaattta tgacatgaa  tagtgctctc    420
ataacggcta ttccactttt tagagttcaa aattatgaag ttgctcttct atctgtatat    480
gttcaagccg caaacttaca tttatctatt ttaagggatg tttcagtttt cggagaaaga    540
tggggatatg atacagcgac tatcaataat cgctatagtg atctgactag ccttattcat    600
gtttatacta accattgtgt ggatacgtat aatcaggat  taaggcgttt ggaaggtcgt    660
tttcttagcg attggattgt atataatcgt ttccggagac aattgacaat ttcagtatta    720
gatattgttg cgttttttcc aaattatgat attagaacat atccaattca aacagctact    780
cagctaacga gggaagtcta tctgatttta ttttttatag gtagaaaatct ttctcctgca    840
gcaaaatatc caacctttc  agctgctgaa agtgctataa ttagaagtcc tcatttagta    900
gactttttaa atagctttac catttataca gatagtctgg cacgttctgc atattgggga    960
gggcacttgg taaattcttt ccgcacagga accactacta atttgataag atcccctta   1020
tatggaaggg aaggaaatac agagcgcccc gtaactatta ccgcatcacc tagcgtacca   1080
atatttagaa cactttcata tccaacaggc cttgacaatt caaatcctgt agctggaatc   1140
```

-continued

```
gagggagtgg aattccaaaa tactataagt agaagtatct atcgtaaaag cggtccaata  1200
gattctttta gtgaattacc acctcaagat gccagcgtat ctcctgcaat tgggtatagt  1260
caccgtttat gccatgcaac atttttagaa cggattagtg gaccaagaat agcaggcacc  1320
gtattttctt ggacacaccg tagtgccagc cctactaacg aagtaagtcc atctagaatt  1380
acacaaattc catgggtaaa ggcgcatact cttgcatctg gtgcctccgt cattaaaggt  1440
cctggattta caggtggaga tattctgact aggaatagta tgggcgagct ggggacctta  1500
cgagtaacct tcacaggaag attaccacaa agttattata tacgtttccg ttatgcttcg  1560
gtagcaaata ggagtggtac atttagatat tcacagccac cttcgtatgg aatttcattt  1620
ccaaaaacta tggacgcagg tgaaccacta acatctcgtt cgttcgctca tacaacactc  1680
ttcactccaa taacctttc acgagctcaa gaagaatttg atctatacat ccaatcgggt  1740
gtttatatag atcgaattga atttataccg gttactgcaa catttgaggc agaatatgat  1800
ttagaaagag cgcaaaaggt ggtgaatgcc ctgtttacgt ctacaaacca actagggcta  1860
aaaacagatg tgacggatta tcatattgat caggtatcca atctagttgc gtgtttatcg  1920
gatgaatttt gtctggatga aaagagagaa ttgtccgaga aagttaaaca tgcaaagcga  1980
ctcagtgatg agcggaattt acttcaagat ccaaacttca gagggatcaa taggcaacca  2040
gaccgtggct ggagaggaag tacggatatt actatccaag gaggagatga cgtattcaaa  2100
gagaattacg ttacgctacc gggtaccttt gatgagtgct atccaacgta tttatatcaa  2160
aaaatagatg agtcgaaatt aaaagcctat acccgttatc aattaagagg gtatatcgaa  2220
gatagtcaag acttagaaat ctatttaatt cgttacaatg caaaacacga aatagtaaat  2280
gtaccaggta caggaagttt atggcctctt tctgtagaaa atcaaattgg accttgtgga  2340
gaaccgaatc gatgcgcgcc acaccttgaa tggaatcctg atttacactg ttcctgcaga  2400
gacggggaaa aatgtgcaca tcattctcat catttctctt tggacattga tgttggatgt  2460
acagacttaa atgaggactt aggtgtatgg gtgatattca agattaagac gcaagatggc  2520
cacgcacgac tagggaatct agagtttctc gaagagaaac cattattagg agaagcacta  2580
gctcgtgtga aaagagcgga gaaaaaatgg agagacaaac gcgaaacatt acaattggaa  2640
acaactatcg tttataaaga ggcaaaagaa tctgtagatg ctttatttgt aaactctcaa  2700
tatgatagat tacaagcgga tacgaacatc gcgatgattc atgcggcaga taaacgcgtt  2760
catagaattc gagaagcgta tctgccggag ctgtctgtga ttccgggtgt caatgcggct  2820
atttttgaag aattagaaga gcgtattttc actgcatttt ccctatatga tgcgagaaat  2880
attattaaaa atggcgattt caataatggc ttattatgct ggaacgtgaa agggcatgta  2940
gaggtagaag aacaaaacaa tcaccgttca gtcctggtta tcccagaatg ggaggcagaa  3000
gtgtcacaag aggttcgtgt ctgtccaggt cgtggctata tccttcgtgt tacagcgtac  3060
aaagagggat atggagaagg ttgcgtaacg atccatgaga tcgagaacaa tacagacgaa  3120
ctgaaattca acaactgtgt agaagaggaa gtatatccaa acaacacggt aacgtgtatt  3180
aattatactg cgactcaaga agaatatgag ggtacgtaca cttctcgtaa tcgaggatat  3240
gacgaagcct atggtaataa cccttccgta ccagctgatt atgcgtcagt ctatgaagaa  3300
aaatcgtata cagatagacg aagagagaat ccttgtgaat ctaacagagg atatggagat  3360
tacacaccac taccagctgg ttatgtaaca aaggaattag agtacttccc agagaccgat  3420
aaggtatgga ttgagattgg agaaacagaa ggaacattca tcgtggacag cgtggaatta  3480
ctccttatgg aggaatag                                                 3498

SEQ ID NO: 10           moltype = AA  length = 1165
FEATURE                 Location/Qualifiers
REGION                  1..1165
                        note = Amino acid sequence of the engineered insecticidal
                         proteinCry1Da1_6.
source                  1..1165
                        mol_type = protein
                        organism = synthetic construct
SEQUENCE: 10
MEINNQNQCV PYNCLSNPKE IILGEERLET GNTVADISLG LINFLYSNFV PGGGFIVGLL  60
ELIWGFIGPS QWDIFLAQIE QLISQRIEEF ARNQAISRLE GLSNLYKVYV RAFSDWEKDP  120
TNPALREEMR IQFNDMNSAL ITAIPLFRVQ NYEVALLSVY VQAANLHLSI LRDVSVFGER  180
WGYDTATINN RYSDLTSLIH VYTNHCVDTY NQGLRRLEGR FLSDWIVYNR FRRQLTISVL  240
DIVAFFPNYD IRTYPIQTAT QLTREVYLDL PFINENLSPA AKYPTFSAAE SAIIRSPHLV  300
DFLNSFTIYT DSLARSAYWG GHLVNSFRTG TTTNLIRSPL YGREGNTERP VTITASPSVP  360
IFRTLSYPTG LDNSNPVAGI EGVEFQNTIS RSIYRKSGPI DSFSELPPQD ASVSPAIGYS  420
HRLCHATFLE RISGPRIAGT VFSWTHRSAS PTNEVSPSRI TQIPWVKAHT LASGASVIKG  480
PGFTGGDILT RNSMGELGTL RVTFTGRLPQ SYYIRFRYAS VANRSGTFRY SQPPSYGISF  540
PKTMDAGEPL TSRSFAHTTL FTPITFSRAQ EEFDLYIQSG VYIDRIEFIP VTATFEAEYD  600
LERAQKVVNA LFTSTNQLGL KTDVTDYHID QVSNLVACLS DEFCLDEKRE LSEKVKHAKR  660
LSDERNLLQD PNFRGINRQP DRGWRGSTDI TIQGGDDVFK ENYVTLPGTF DECYPTYLYQ  720
KIDESKLKAY TRYQLRGYIE DSQDLEIYLI RYNAKHEIVN VPGTGSLWPL SVENQIGPCG  780
EPNRCAPHLE WNPDLHCSCR DGEKCAHHSH HFSLDIDVGC TDLNEDLGVW VIFKIKTQDG  840
HARLGNLEFL EEKPLLGEAL ARVKRAEKKW RDKRETLQLE TTIVYKEAKE SVDALFVNSQ  900
YDRLQADTNI AMIHAADKRV HRIREAYLPE LSVIPGVNAA IFEELEERIF TAFSLYDARN  960
IIKNGDFNNG LLCWNVKGHV EVEEQNNHRS VLVIPEWEAE VSQEVRVCPG RGYILRVTAY  1020
KEGYGEGCVT IHEIENNTDE LKFNNCVEEE VYPNNTVTCI NYTATQEEYE GTYTSRNRGY  1080
DEAYGNNPSV PADYASVYEE KSYTDRRREN PCESNRGYGD YTPLPAGYVT KELEYFPETD  1140
KVWIEIGETE GTFIVDSVEL LLMEE                                          1165

SEQ ID NO: 11           moltype = DNA  length = 3498
FEATURE                 Location/Qualifiers
misc_feature            1..3498
                        note = Nucleotide sequence used for expression in a
                         bacterial cellencoding Cry1Da1_7.
source                  1..3498
                        mol_type = other DNA
                        organism = synthetic construct
```

-continued

```
SEQUENCE: 11
atggaaataa ataatcaaaa ccaatgtgtg ccttacaatt gtttaagtaa tcctaaggag    60
ataatattag gcgaggaaag gctagaaaca gggaatactg tagcagacat ttcattaggg   120
cttattaatt ttctatattc taattttgta ccaggaggag gatttatagt aggtttacta   180
gaattaatat ggggatttat agggccttcg caatggatta ttttttttagc tcaaattgga   240
caattgatta gtcaaagaat agaagaattt gctaggaatc aggcaatttc aagattggag   300
gggctaagca atctttataa ggtctatgtt agagcgttta gcgactggga aaagatcct   360
actaatcctg ctttaaggga gaaatgcgt atacaattta tgacatgaa tagtgctctc   420
ataacggcta ttccactttt tagagttcaa aattatgaag ttgctctttt atctgtatat   480
gttcaagccg caaacttaca tttatctatt ttaagggatg tttcagtttt cggagaaaga   540
tggggatatg atacagcgac tatcaataat cgctatagtg atctgactag ccttattcat   600
gtttatacta accattgtgt ggatacgtat aatcagggat taaggcgttt ggaaggtcgt   660
tttcttagcg attggattgt atataatcgt ttccggagac aattgacaat ttcagtatta   720
gatattgttg cgttttttcc aaattatgat attagaacat atccaattca aacagctact   780
cagctaacga gggaagtcta tctgattta ccttttatta atgaaaatct ttctcctgca   840
gcagtatatc caaccttttc agctgctgaa agtgctataa ttagaagtcc tcatttagta   900
gactttttaa atagctttac catttataca gatagtctgg cacgttctgc atattgggga   960
gggcacttgg taaattcttt ccgcacagga accactaca atttgataag atcccctta  1020
tatgaagggg aaggaaatac agagcgcccc gtaactatta ccgcatcacc tagcgtacca  1080
atatttagaa cactttcata tccaacaggc cttgacaatt caaatcctgt agctggaatc  1140
gagggagtgg aattccaaaa tactataagt agaagtatct atcgtaaaag cggtccaata  1200
gattcttta gtgaattacc accctcaagat gccagcgtat ctcctgcaat tgggtatagt  1260
caccgtttat gccatgcaac attttaaga cggattagtg gaccaagaat agcaggcacc  1320
gtattttctt ggacacaccg tagtgccagc cctactaacg aagtaagtcc atctagaatt  1380
acacaaattc catgggtaaa ggcgcatact cttgcatctg gtgcctccgt cattaaaggt  1440
cctggattta caggtggaga tattctgact aggaatagta tgggcgagct ggggaccta  1500
cgagtaacct tcacaggaag attaccacaa agttattata tacgtttccg ttatgcttcg  1560
gtagcaaata ggagtggtac atttagatat tcacagccac cttcgtatgg aatttcattt  1620
ccaaaaacta tggacgcagg tgaaccacta acatctcgtt cgttcgctca tacaacactc  1680
ttcactccaa taccttttc acgagctcaa gaagaatttg atctatacat ccaatcggtt  1740
gtttatatag atcgaattga atttataccg gttactgcaa catttgaggc agaatatgat  1800
ttagaaaagag cgcaaaaggt ggtgaatgcc ctgtttacgt ctacaaacca actagggcta  1860
aaaacagatg tgacggatta tcatattgat caggtatcca atctagttgc gtgtttatcg  1920
gatgaattt gtctggatga aaagagagaa ttgtccgaga aagttaaaca tgcaaagcga  1980
ctcagtgatg agcggaattt acttcaagat ccaaacttca gagggatcaa taggcaacca  2040
gaccgtggct ggagaggaag tacgatatt actatccaag gaggagatga cgtattcaaa  2100
gagaattacg ttacgctacc gggtaccttt gatgagtgct atccaacgta tttatatcaa  2160
aaaatgatg agtcgaaatt aaaagcctat acccgttatc aattaagag gtatatcgaa  2220
gatagtcaag acttagaaat ctatttaatt cgttacaatg caaaacacga aatagtaaat  2280
gtaccaggta caggaagttt atggcctctt tctgtagaaa atcaaattgg accttgtgga  2340
gaaccgaatc gatgcgcgcc acaccttgaa tggaatcctg atttacactg ttcctgcaga  2400
gacggggaaa atgtgcaca tcattctcat catttctctt tggacattga tgttggatgt  2460
acagacttaa atgaggactt aggtgtatgg gtgatattca agattaagac gcaagatgc  2520
cacgcacgac tagggaatct agagttctc gaagagaaac cattattagg agaagcacta  2580
gctcgtgtga aaagagcgga gaaaaaatgg agagacaaac gcgaaacatt acaattggaa  2640
acaactatcg tttataaaga ggcaaagaa tctgtagatg ctttatttgt aaactctcaa  2700
tatgatagat tacaagcgga tacgaacatc gcgatgatc atgcggcaga taacgcgtt  2760
catagaattc gagaagcgta tctgccgag ctgtctgtga ttccgggtgt caatgcggct  2820
atttttgaag aattagaaga gcgtatttc actgcatttt ccctatatga tgcgagaaat  2880
attattaaaa atgcgattt caataatggc ttattatgct ggaacgtgaa agggcatgta  2940
gaggtagaag aacaaaacaa tcaccgttca gtcctggtta tcccagaatg gaggcagaa  3000
gtgtcacaag aggttcgtgt ctgtccaggt cgtggctata tccttcgtgt tacagcgtac  3060
aaagagggat atggagaagg ttgcgtaacg atccatgaga tcgagaacaa tacagacgaa  3120
ctgaaattca caactgtgt agaagaggaa gtatatccaa caacacggt aacgtgtatt  3180
aattatactg cgactcaaga agaatatgag gtacgtaca cttctcgtaa tcgaggatat  3240
gacgaagcct atggtaataa ccctccgta ccagctgatt atgcgtcagt ctatgaagaa  3300
aaatcgtata cagatagcg aagagagaat ccttgtgaat ctaacagagg atatggagat  3360
tacacaccac taccagctgg ttatgtaaca aaggaattag agtactcc agagaccgat  3420
aaggtatgga ttgagattgg agaaacagaa ggaacattca tcgtggacag cgtggaatta  3480
ctccttatgg aggaatag                                                  3498

SEQ ID NO: 12     moltype = AA  length = 1165
FEATURE           Location/Qualifiers
REGION            1..1165
                  note = Amino acid sequence of the engineered insecticidal
                  proteinCry1Da1_7.
source            1..1165
                  mol_type = protein
                  organism = synthetic construct
SEQUENCE: 12
MEINNQNQCV PYNCLSNPKE IILGEERLET GNTVADISLG LINFLYSNFV PGGGFIVGLL    60
ELIWGFIGPS QWDIFLAQIE QLISQRIEEF ARNQAISRLE GLSNLYKVYV RAFSDWEKDP   120
TNPALREEMR IQFNDMNSAL ITAIPLFRVQ NYEVALLSVY VQAANLHLSI LRDVSVFGER   180
WGYDTATINN RYSDLTSLIH VYTNHCVDTY NQGLRRLEGR FLSDWIVYNR FRRQLTISVL   240
DIVAFFPNYD IRTYPIQTAT QLTREVYLDL PFINENLSPA AVYPTFSAAE SAIIRSPHLV   300
DFLNSFTIYT DSLARSAYWG GHLVNSFRTG TTTNLIRSPL YGREGNTERP VTITASPSVP   360
IFRTLSYPTG LDNSNPVAGI EGVEFQNTIS RSIYRKSGPI DSFSELPPQD ASVSPAIGYS   420
HRLCHATFLE RISGPRIAGT VFSWTHRSAS PTNEVSPSRI TQIPWVKAHT LASGASVIKG   480
PGFTGGDILT RNSMGELGTL RVTFTGRLPQ SYYIRFRYAS VANRSGTFRY SQPPSYGISF   540
```

```
PKTMDAGEPL TSRSFAHTTL FTPITFSRAQ EEFDLYIQSG VYIDRIEFIP VTATFEAEYD   600
LERAQKVVNA LFTSTNQLGL KTDVTDYHID QVSNLVACLS DEFCLDEKRE LSEKVKHAKR   660
LSDERNLLQD PNFRGINRQP DRGWRGSTDI TIQGGDDVFK ENYVTLPGTF DECYPTYLYQ   720
KIDESKLKAY TRYQLRGYIE DSQDLEIYLI RYNAKHEIVN VPGTGSLWPL SVENQIGPCG   780
EPNRCAPHLE WNPDLHCSCR DGEKCAHHSH HFSLDIYGC TDLNEDLGVW VIFKIKTQDG   840
HARLGNLEFL EEKPLLGEAL ARVKRAEKKW RDKRETLQLE TTIVYKEAKE SVDALFVNSQ   900
YDRLQADTNI AMIHAADKRV HRIREAYLPE LSVIPGVNAA IFEELEERIF TAFSLYDARN   960
IIKNGDFNNG LLCWNVKGHV EVEEQNNHRS VLVIPEWEAE VSQEVRVCPG RGYILRVTAY  1020
KEGYGEGCVT IHEIENNTDE LKFNNCVEEE VYPNNTVTCI NYTATQEEYE GTYTSRNRGY  1080
DEAYGNNPSV PADYASVYEE KSYTDRRREN PCESNRGYGD YTPLPAGYVT KELEYFPETD  1140
KVWIEIGETE GTFIVDSVEL LLMEE                                       1165

SEQ ID NO: 13              moltype = DNA  length = 3420
FEATURE                    Location/Qualifiers
misc_feature               1..3420
                           note = Nucleotide sequence used for expression in a
                           bacterial cellencoding TIC844.
source                     1..3420
                           mol_type = other DNA
                           organism = synthetic construct
SEQUENCE: 13
atggagatca acaaccagaa ccagtgcgtc ccgtacaact gcctgagcaa ccctaaggag   60
atcatcctgg gtgaggaacg cctggagacc ggcaacaccg tagccgacat tagcctgggc  120
ctcatcaact tcctctacag caacttcgtg cccggcggtg gcttcatcgt gggcctcctg  180
gagcttatct ggggcttcat cggcccgtcc cagtgggaca tcttcctcgc ccagatcgag  240
caactgatca gccagcggat cgaggagttc gctaggaaac aggccatctc ccgcctggaa  300
ggactctcca acctctacaa ggtgtacgtg cgcgcgttca gcgactggga gaaggacccg  360
accaaccccg ccctccgcga ggaaatgcgt atccagttca acgatatgaa ctcggccctc  420
atcaccgcca tcccgctctt ccgcgtgcag aactacgagg tggccctcct gtccgtgtac  480
gttcaagccg ccaacctcca cctctccatc ctccgcgacg tgagcgtgtt cggcgagcgc  540
tggggctacg acaccgccac catcaacaac cgctactccg acctcaccct cctcatccac  600
gtttacacca accactgcgt ggacacgtac aaccagggcc tccgcgcct ggagggccgc  660
ttcctctccg actggatcgt gtacaaccgc ttccgccgcc agctcaccat ctccgtcctg  720
gacatcgtcg ccttctttcc caactacgac atccgcacct accctatccg gaccgccacc  780
cagctcaccc gcgaggtcta cctcgacctc ccgttcatca acgagaacct cagcccggcc  840
gccagctacc cgaccttctc cgccgctgag tccgccatca ttcgcagccc gcacctcgtg  900
gacttcctca actccttcac catctacacc gactccctcg cccgctacgc ctactgggc   960
ggtcacctcg tgaactcctt ccgcaccggc accactacca acctcatccg cagcccgctc  1020
tacggccgcg agggcaacac cgagcgcccg gtgaccatca ccgcgaccgc gagcgtgccc  1080
atcttccgca ccctcagcta catcaccggc ctggacaaca gcaacccgt ggcgggcatc   1140
gagggcgtgg agttccagaa caccatctcc aggagcatct accgcaagag cggccctatc  1200
gacagcttca gcgagctgcc tcctcaggac gccagcgtga ccctgccat cggctacagc   1260
cacaggccgt gccacgccac cttcctggag cgcatcaggc gcctcgcat cgcgggcacc  1320
gtgttctcgt ggacccaccg cagcgcctct cctacgaacg aggtgtctcc tagtcgcatc  1380
acccagatcc cttgggtcaa ggcccacacc tggctagtg cgctagtgt catcaagggc   1440
cctggcttca ccggtggtga catcctgacc aggaactcta tgggcgagct gggcactctg  1500
agggtcacttt tcactggccg cctgcctcag tcttactaca tccgcttccg ctacgctagt  1560
gtcgctaacc gctctggtac tttccgctac tctcagcctc cgtcttacgg tatctctttc  1620
cctaagacta tggacgctgg tgagcctctg accagtagga gcttcgctca cactactctg  1680
ttcactccta tcactttctc tagggctcag gaggagttcg acctgtacat ccagtctggt  1740
gtgtacatcg acaggatcga gttcatcccc gtgaccgcca cgttccaggc cgagtacgac  1800
cttgagcgcg cccagaaggc tgtcaatgag ctcttcacgt ccagcaatca gatcggcctg  1860
aagaccgacg tcactgacta ccacatcgac caagtctcca acctcgtgga gtgcctctcc  1920
gatgagttct gcctcgacga gaagaaggag ctgtccgaga aggtgaagca tgccaagcgt  1980
ctcagcgacg agaggaatct cctccaggac cccaattcc gccgcatcaa caggcagctc  2040
gaccgcggct ggcgcggcag caccgacatc acgatccagg gcggcgacga tgtgttcaag  2100
gagaactacg tgactctcct gggcactttc gacgagtgct accctaccta cttgtaccag  2160
aagatcgatg agtccaagct caaggcttac actcgctacc agctccgcgg ctacatcgaa  2220
gacagccaag acctcgagat ttacctgatc cgctacaacg ccaagcacga gatcgtcaac  2280
gtgcccggta ctggttccct ctggccgctg agcgccccca gcccgatcgg caagtgtgcc  2340
caccacagcc accacttctc cttggacatc gatgtgggct gcaccgacct gaacgaggac  2400
ctcggagtct gggtcatctt caagatcaag acccaggacg ccacgcgcg cctgggcaac  2460
ctggagttcc tcgaggagaa gcccctggtc ggtgaggctc tggccagggt caagagggct  2520
gagaagaagt ggagggacaa gcgcgagctg cagctggag ccaacaat cgtttacagg    2580
gaggccaagg agagcgtcga cgccctgttc gtgaactccc agtacagacc cctgcaggcc  2640
gacaccaaca tcgccatgat ccacgctgcc gacaagaggg tgcacagcat cgcgaggcc   2700
tacctgcctg agctgtccgt gatccctggt gtgaacgctg ccatctttga ggagctggag  2760
ggccgcatct ttaccgcatt ctccctgtac gacgcccgca acgtgatcaa gaacggtgac  2820
ttcaacaatg gcctcagctg ctggaacgtc aagggccacg tggacgtcga ggaacagaac  2880
aaccaccgct ccgtcctggt cgtcccagag tgggaggctg aggtctccca gaggtccgc   2940
gtctgcccag gccgcggcta cattctcagg gtcaccgctt acaaggaggg ctacggtgag  3000
ggctgtgtga ccatccacga gatcgagaac aacaccgacg agcttaagtt ctccaactgc  3060
gtggaggagg aggtgtaccc aaacaacacc gttacttgca acgactacac cgccacccag  3120
gaggagtacg aggggaccta cacttccagg aacaggggct acggtgagag c           3180
aacagcagcg ttcctgctga ctacgcttcc gcctacgagg agaaggccta cacgggatgc  3240
cgcagggaca cccttgcga gagcaaccgg gctacggcg actacactcc cctgcccgcc   3300
ggctacgtta ccaaggagct ggagtacttc cggagactg caaggtgtg gatcgagatc   3360
ggcgagaccg agggcacctt catcgtggac agcgtggagc tgctcctgat ggaggagtag  3420
```

-continued

```
SEQ ID NO: 14            moltype = AA   length = 1139
FEATURE                  Location/Qualifiers
REGION                   1..1139
                         note = Amino acid sequence of the chimeric protein TIC844.
source                   1..1139
                         mol_type = protein
                         organism = synthetic construct
SEQUENCE: 14
MEINNQNQCV PYNCLSNPKE IILGEERLET GNTVADISLG LINFLYSNFV PGGGFIVGLL    60
ELIWGFIGPS QWDIFLAQIE QLISQRIEEF ARNQAISRLE GLSNLYKVYV RAFSDWEKDP   120
TNPALREEMR IQFNDMNSAL ITAIPLFRVQ NYEVALLSVY VQAANLHLSI LRDVSVFGER   180
WGYDTATINN RYSDLTSLIH VYTNHCVDTY NQGLRRLEGR FLSDWIVYNR FRRQLTISVL   240
DIVAFFPNYD IRTYPIQTAT QLTREVYLDL PFINENLSPA ASYPTFSAAE SAIIRSPHLV   300
DFLNSFTIYT DSLARYAYWG GHLVNSFRTG TTTNLIRSPL YGREGNTERP VTITASPSVP   360
IFRTLSYITG LDNSNPVAGI EGVEFQNTIS RSIYRKSGPI DSFSELPPQD ASVSPAIGYS   420
HRLCHATFLE RISGPRIAGT VFSWTHRSAS PTNEVSPSRI TQIPWVKAHT LASGASVIKG   480
PGFTGGDILT RNSMGELGTL RVTFTGRLPQ SYYIRFRYAS VANRSGTFRY SQPPSYGISF   540
PKTMDAGEPL TSRSFAHTTL FTPITFSRAQ EEFDLYIQSG VYIDRIEFIP VTATFEAEYD   600
LERAQKAVNE LFTSSNQIGL KTDVTDYHID QVSNLVECLS DEFCLDEKKE LSEKVKHAKR   660
LSDERNLLQD PNFRGINRQL DRGWRGSTDI TIQGGDDVFK ENYVTLLGTF DECYPTYLYQ   720
KIDESKLKAY TRYQLRGYIE DSQDLEIYLI RYNAKHETVN VPGTGSLWPL SAPSPIGKCA   780
HHSHHFSLDI DVGCTDLNED LGVWVIFKIK TQDGHARLGN LEFLEEKPLV GEALARVKRA   840
EKKWRDKREK LEWETNIVYK EAKESVDALF VNSQYDRLQA DTNIAMIHAA DKRVHSIREA   900
YLPELSVIPG VNAAIFEELE GRIFTAFSLY DARNVIKNGD FNNGLSCWNV KGHVDVEEQN   960
NHRSVLVVPE WEAEVSQEVR VCPGRGYILR VTAYKEGYGE GCVTIHEIEN NTDELKFSNC  1020
VEEEVYPNNT VTCNDYTATQ EEYEGTYTSR NRGYDGAYES NSSVPADYAS AYEEKAYTDG  1080
RRDNPCESNR GYGDYTPLPA GYVTKELEYF PETDKVWIEI GETEGTFIVD SVELLLMEE   1139

SEQ ID NO: 15            moltype = DNA   length = 3420
FEATURE                  Location/Qualifiers
misc_feature             1..3420
                         note = Nucleotide sequence used for expression in a
                         bacterial cellencoding TIC844_2.
source                   1..3420
                         mol_type = other DNA
                         organism = synthetic construct
SEQUENCE: 15
atggaaataa ataatcaaaa ccaatgtgtg ccttacaatt gtttaagtaa tcctaaggag    60
ataatattag gcgaggaaag gctagaaaca gggaatactg tagcagacat ttcattaggg   120
cttattaatt ttctatattc taattttgta ccaggaggag gatttatagt aggtttacta   180
gaattaatat ggggatttat agggccttcg caatgggata tttttttagc tcaaattgag   240
caattgatta gtcaaagaat agaagaattt gctaggaatc aggcaatttc aagattggag   300
gggctaagca atctttataa ggtctatgtt agagcgttgg gcgactggga aaagatcct   360
actaatcctg cttttaaggga agaaatgcgt atacaattta tgacatgaa tagtgctctc   420
ataacggcta ttccactttt tagagttcaa aattatgaag ttgctctttt atctgtatat   480
gttcaagccg caaacttaca tttatctatt ttaagggatg tttcagtttt cggagaaaga   540
tggggatatg atacagcgac tatcaataat cgctatagtg atctgactag ccttattcat   600
gtttatacta accattgtgt ggatacgtat aatcagggat taaggcgttt ggaaggtcgt   660
tttcttagcg attggattgt atataatcgt ttccggagac aattgacaat ttcagtatta   720
gatattgttg cgttttttcc aaattatgat attagaacat atccaattca aacagctact   780
cagctaacga gggaagtcta tctgagttta ccttttatta atgaaaatct ttctcctgca   840
gcaagctatc caacctttc agctgctgaa agtgctataa ttagaagtcc tcatttagta   900
gacttttaa atagctttac catttataca gatagtctgg cacgttctgc atattgggga   960
gggcacttgg taaattcttt ccgcacagga accactacta atttgataag atccccttta  1020
tatgggaagg aaggaaatac agagcgcccc gtaactacta ccgcatcacc tagcgtacca  1080
atatttagaa cactttcata tattacaggc cttgacaatt cacatcctgt agctggaatc  1140
gagggagtgg aattccaaaa tactataagt gaaagtatct atcgtaaaag cggtccaata  1200
gattctttta gtgaattacc acctcaagat gccagcgtat ctcctgcaat tgggtatagt  1260
caccgtttat gccatgcaac ttttttagaa cggttaagtg gaccaagaat agcaggcact  1320
gtatttcttt ggacacaccg tagtgccagc cctactacag aagtaagtcc atctagaatt  1380
acacaaattc catgggtaaa ggcgcatact cttgcatctg gtgcctccgt cattaaaggt  1440
cctggattta caggtggaga tattctgact aggaatagta tgggcgagct ggggacctta  1500
cgagtaacct tcacaggaag attaccacaa agttattata tacgtttccg ttatgcttcg  1560
gtagcaaata ggagtggtac attatagtat tcacagccac cttcgtatgg aatttcattt  1620
ccaaaaacta tggacgcagg tgaaccacta acatctcgtt cgttcgctca tacaacactc  1680
ttcactccaa taccttttc acgagctcaa gaagaatttg atctatacat ccaatcgggt  1740
gtttatatag atcgaattga atttataccg gttactgcaa catttgaggc agaatatgat  1800
ttagaaagag cacaaaaggc ggtgaatgag ctgttttctt cttccaatca aatcgggtta  1860
aaaacagatg tgacggatta tcatattgat caagtatca atttagttga gtgtttatct  1920
gatgaatttt gtctggatga aaaaaagaa ttgtccgaga aagtcaaaca tgcgaagcga  1980
cttagtgatg agcggaattt acttcaagat ccaaacttta gagggatcaa tagacaacta  2040
gaccgtggct ggagaggaag tacggatatt accatccaag gaggcgatga cgtattcaaa  2100
gagaattacg ttacgctatt gggtaccttt gatgagtgct atccaaacgta tttatatcaa  2160
aaaatagatg agtcgaaatt aaaagcgcta t acccgttacc aattaagagg gtatatcgaa  2220
gatagtcaag acttagaaat ctatttaatt cgctacaatg ccaaacacga aacagtaaat  2280
gtgccaggta cgggttcctt atggccgctt tcagccccaa gtccaatcgg aaaatgtgcc  2340
catcattccc atcattttc cttggacatt gatgttggat gtacagactt aaatgaggac  2400
ttaggtgtat gggtgatatt caagattaag acgcaagatg gccatgcaag actaggaaat  2460
ctagaatttc tcgaagagaa accattagta ggagaagcac tagctcgtgt gaaaagagcg  2520
```

-continued

```
gagaaaaaat ggagagacaa acgtgaaaaa ttggaatggg aaacaaatat tgtttataaa 2580
gaggcaaaag aatctgtaga tgctttattt gtaaactctc aatatgatag attacaagcg 2640
gataccaaca tcgcgatgat tcatgcggca gataaacgcg ttcatagcat tcgagaagct 2700
tatctgcctg agctgtctgt gattccgggt gtcaatgcgg ctatttttga agaattagaa 2760
gggcgtattt tcactgcatt ctccctatat gatgcgagca atgtcattaa aaatggtgat 2820
tttaataatg gcttatcctg ctggaacgtg aaagggcatg tagatgtaga agaacaaaac 2880
aaccaccgtt cggtccttgt tgttccgaaa tgggaagcag aagtgtcaca agaagttcgt 2940
gtctgtccgg gtcgtggcta tatccttcgt gtcacagcgt acaaggaggg atatggaaaa 3000
ggttgcgtaa ccattcatga gatcgagaac aatacagacg aactgaagtt tagcaactgt 3060
gtagaagagg aagtatatcc aaacaacacg gtaacgtgta atgattatac tgccgactgt 3120
gaagaatatg agggtacgta cacttctcgt aatcgaggat atgacggagc ctatgaaagc 3180
aattcttctg taccagctga ttatgcatca gcctatgaag aaaaagcata tacagatgga 3240
cgaagagaca atccttgtga atcaacaga ggatatgggg attacacacc actaccagct 3300
ggctatgtga caaaagaatt agagtacttc ccagaaaccg ataaggtatg gattgagatc 3360
ggagaaacgg aaggaacatt catcgtggac agcgtggaca tacttcttat ggaggaatag 3420

SEQ ID NO: 16        moltype = AA  length = 1139
FEATURE              Location/Qualifiers
REGION               1..1139
                     note = Amino acid sequence of the engineered insecticidal
                     chimericprotein TIC844_2.
source               1..1139
                     mol_type = protein
                     organism = synthetic construct
SEQUENCE: 16
MEINNQNQCV PYNCLSNPKE IILGEERLET GNTVADISLG LINFLYSNFV PGGGFIVGLL   60
ELIWGFIGPS QWDIFLAQIE QLISQRIEEF ARNQAISRLE GLSNLYKVYV RAFSDWEKDP  120
TNPALREEMR IQFNDMNSAL ITAIPLFRVQ NYEVALLSVY VQAANLHLSI LRDVSVFGER  180
WGYDTATINN RYSDLTSLIH VYTNHCVDTY NQGLRRLEGR FLSDWIVYNR FRRQLTISVL  240
DIVAFFPNYD IRTYPIQTAT QLTREVYLDL PFINENLSPA ASYPTFSAAE SAIIRSPHLV  300
DFLNSFTIYT DSLARSAYWG GHLVNSFRTG TTTNLIRSPL YGREGNTERP VTITASPSVP  360
IFRTLSYITG LDNSHPVAGI EGVEFQNTIS RSIYRKSGPI DSFSELPPQD ASVSPAIGYS  420
HRLCHATFLE RLSGPRIAGT VFSWTHRSAS PTNEVSPSRI TQIPWVKAHT LASGASVIKG  480
PGFTGGDILT RNSMGELGTL RVTFTGRLPQ SYYIRFRYAS VANRSGTFRY SQPPSYGISF  540
PKTMDAGEPL TSRSFAHTTL FTPITFSRAQ EEFDLYIQSG VYIDRIEFIP VTATFEAEYD  600
LERAQKAVNE LFTSSNQIGL KTDVTDYHID QVSNLVECLS DEFCLDEKKE LSEKVKHAKR  660
LSDERNLLQD PNFRGINRQL DRGWRGSTDI TIQGGDDVFK ENYVTLLGTF DECYPTYLYQ  720
KIDESKLKAY TRYQLRGYIE DSQDLEIYLI RYNAKHETVN VPGTGSLWPL SAPSPIGKCA  780
HHSHHFSLDI DVGCTDLNED LGVWWVIFKIK TQDGHARLGN LEFLEEKPLV GEALARVKRA  840
EKKWRDKREK LEWETNIVYK EAKESVDALF VNSQYDRLQA DTNIAMIHAA DKRVHSIREA  900
YLPELSVIPG VNAAIFEELE GRIFTAFSLY DARNVIKNGD FNNGLSCWNV KGHVDVEEQN  960
NHRSVLVVPE WEAEVSQEVR VCPGRGYILR VTAYKEGYGE GCVTIHEIEN NTDELKFSNC 1020
VEEEVYPNNT VTCNDYTATQ EEYEGTYTSR NRGYDGAYES NSSVPADYAS AYEEKAYTDG 1080
RRDNPCESNR GYGDYTPLPA GYVTKELEYF PETDKVWIEI GETEGTFIVD SVELLLMEE  1139

SEQ ID NO: 17        moltype = DNA  length = 3420
FEATURE              Location/Qualifiers
misc_feature         1..3420
                     note = Nucleotide sequence used for expression in a
                     bacterial cellencoding TIC844_4.
source               1..3420
                     mol_type = other DNA
                     organism = synthetic construct
SEQUENCE: 17
atggaaataa ataatcaaaa ccaatgtgtg ccttacaatt gtttaagtaa tcctaaggag   60
ataatattag gcgaggaaag gctagaaaca gggaatactg tagcagacat tcattaggg  120
cttattaatt ttctatattc taattttgta ccaggaggag gatttatagt aggttttacta 180
gaattaatat ggggatttat agggccttcg caatgggata ttttttttagc tcaaattgag 240
caattgatta gtcaaagaat aagagaattt gctaggaatc aggcaatttc aagattggag 300
gggctaagca atctttataa ggtctatgtt agagcgttta gcgactggga gaaagatcct 360
actaatcctg ctttaaggga gaaaatgcgt atacaattta tgacatgaa tagtgctctc 420
ataacggcta ttccactttt tagagttcaa aattatgaag ttgctctttt atctgtatat 480
gttcaagccg caaacttaca tttatctatt ttaagggatg tttcagtttt cggagaaaga 540
tggggatatg atacagcgac tatcaataat cgctattggt atctgacttg ccttattcat 600
gtttatacta accattgtgt ggatacgtat aatcaggat taaggcgttt ggaaggtcgt 660
tttcttagcg attggattgt atataatcgt ttccggagac aattgacaat tcagtatta 720
gatattgttg cgtttttttcc aaattatgat attagaacat atccaattca aacagctact 780
cagctaacga gggaagtcta tctggattta ccttttatta tgaaaaatct ttctcctgca 840
gcaagctatc caacctttc agctgctgaa agtgctataa ttagaagtcc tcatttagta 900
gacttttta atagctttac catttatac gatagtctgg cacgtagtgc atattgggga 960
gggcacttgg taaattcttt ccgcacagga accactacta atttgataag atccctta 1020
tatgaagggg aaggaaatac agagcgcccc gtaactatta ccgcatcacc tagcgtacca 1080
atatttgaa cactttcata tattacaggc cttgacaatt caaatcctgt agctggaatc 1140
gagggagtgg aattccaaaa tactataagt gaagtatct atcgtaaaag cggtccaata 1200
gattctttta gtgaattacc acctcaagat gccagcgtat ctcctgcaat gggtatagt 1260
caccgtttat gccatgcaac attttttagaa cggattagtg gaccaagaat agcaggcacc 1320
gtattttctt ggacacaccg tagtgccagc cctactaacg aagtaagtcc atctagaatt 1380
acacaaattc catgggtaaa ggcgcatact cttgcatctg gtgcctccgt cattaaaggt 1440
cctggattta caggtggaga tattctgact aggaatagta tgggcgagct ggggacctta 1500
```

-continued

```
cgagtaacct tcacaggaag attaccacaa agttattata tacgtttccg ttatgcttcg  1560
gtagcaaata ggagtggtac atttagatat tcacagccac cttcgtatgg aatttcattt  1620
ccaaaaacta tggacgcagg tgaaccacta acatctcgtt cgttcgctca tacaacactc  1680
ttcactccaa taaccttttc acgagctcaa gaagaatttg atctatacat ccaatcgggt  1740
gtttatatag atcgaattga atttataccg gttactgcaa catttgaggc agaatatgat  1800
ttagaaagag cacaaaaggc ggtgaatgag ctgtttactt cttccaatca aatcgggtta  1860
aaaacagatg tgacggatta tcatattgat caagtatcca atttagttga gtgtttatct  1920
gatgaatttt gtctggatga aaaaaaagaa ttgtccgaga aagtcaaaca tgcgaagcga  1980
cttagtgatg agcggaattt acttcaagat ccaaacttta gagggatcaa tagacaacta  2040
gaccgtggct ggagaggaag tacggatatt accatccaag gaggcgatga cgtattcaaa  2100
gagaattacg ttacgctatt gggtaccttt gatgagtgct atccaacgta tttatatcaa  2160
aaaatagatg agtcgaaatt aaaagcctat acccgttacc aattaagagg gtatatcgaa  2220
gatagtcaag acttagaaat ctatttaatt cgctacaatg ccaaacacga aacagtaaat  2280
gtgccaggta cgggttcctt atggccgctt tcagccccaa gtccaatcgg aaaatgtgcc  2340
catcattccc atcatttctc cttggacatt gatgttggat gtacagactt aaatgaggac  2400
ttaggtgtat gggtgatatt caagattaag acgcaagatg gccatgcaag actaggaaat  2460
ctagaatttc tcgaagagaa accattagta ggagaagcac tagctcgtgt gaaaagagcg  2520
gagaaaaaat ggagagacaa acgtgaaaaa ttggaatggg aaacaaatat tgtttataaa  2580
gaggcaaaag aatctgtaga tgctttattt gtaaactctc aatatgatag attacaagcg  2640
gataccaaca tcgcgatgat tcatgcggca gataaacgcg ttcatagcat tcgagaagct  2700
tatctgcctg agctgtctgt gattccgggt gtcaatgcgg ctatttttga agaattagaa  2760
gggcgtattt tcactgcatt ctccctatat gatgcgagaa atgtcattaa aaatggtgat  2820
tttaataatg gcttatcctg ctggaacgtg aaagggcatg tagatgtaga agaacaaaac  2880
aaccaccgtt cggtccttgt tgttccggaa tgggaagcag aagtgtcaca agaagttcgt  2940
gtctgtccgg gtcgtggcta tatccttcgt gtcacagcgt acaaggaggg atatggagaa  3000
ggttgcgtaa ccattcatga gatcgagaac aatacagacg aactgaagtt tagcaactgt  3060
gtagaagagg aagtatatcc aaacaacacg gtaacgtgta atgattatac tgcgactcaa  3120
gaagaatatg agggtacgta cacttctcgt aatcgaggat atgacggagc ctatgaaagc  3180
aattcttctg taccagctga ttatgcatca gcctatgaag aaaaagcata tacagatgga  3240
cgaagagaca atccttgtga atctaacaga ggatatgggg attacacacc actaccagct  3300
ggctatgtga caaaagaatt agagtacttc ccagaaaccg ataaggtatg gattgagatc  3360
ggagaaacgg aaggaacatt catcgtggac agcgtggaat tacttcttat ggaggaatag  3420
```

```
SEQ ID NO: 18          moltype = AA  length = 1139
FEATURE                Location/Qualifiers
REGION                 1..1139
                       note = Amino acid sequence of the engineered insecticidal
                        chimericprotein TIC844_4.
source                 1..1139
                       mol_type = protein
                       organism = synthetic construct
SEQUENCE: 18
MEINNQNQCV PYNCLSNPKE IILGEERLET GNTVADISLG LINFLYSNFV PGGGFIVGLL  60
ELIWGFIGPS QWDIFLAQIE QLISQRIEEF ARNQAISRLE GLSNLYKVYV RAFSDWEKDP  120
TNPALREEMR IQFNDMNSAL ITAIPLFRVQ NYEVALLSVY VQAANLHLSI LRDVSVFGER  180
WGYDTATINN RYSDLTSLIH VYTNHCVDTY NQGLRRLEGR FLSDWIVYNR FRRQLTISVL  240
DIVAFFPNYD IRTYPIQTAT QLTREVYLDL PFINENLSPA ASYPTFSAAE SAIIRSPHLV  300
DFLNSFTIYT DSLARSAYWG GHLVNSFRTG TTTNLIRSPL YGREGNTERP VTITASPSVP  360
IFRTLSYITG LDNSNPVAGI EGVEFQNTIS RSIYRKSGPI DSFSELPPQD ASVSPAIGYS  420
HRLCHATFLE RISGPRIAGT VFSWTHRSAS PTNEVSPSRI TQIPWVKAHT LASGASVIKG  480
PGFTGGDILT RNSMGELGTL RVTFTGRLPQ SYYIRFRYAS VANRSGTFRY SQPPSYGISF  540
PKTMDAGEPL TSRSFAHTTL FTPITFSRAQ EEFDLYIQSG VYIDRIEFIP VTATFEAEYD  600
LERAQKAVNE LFTSSNQIGL KTDVTDYHID QVSNLVECLS DEFCLDEKKE LSEKVKHAKR  660
LSDERNLLQD PNFRGINRQL DRGWRGSTDI TIQGGDDVFK ENYVTLLGTF DECYPTYLYQ  720
KIDESKLKAY TRYQLRGYIE DSQDLEIYLI RYNAKHETVN VPGTGSLWPL SAPSPIGKCA  780
HHSHHFSLDI DVGCTDLNED LGVWVIFKIK TQDGHARLGN LEFLEEKPLV GEALARVKRA  840
EKKWRDKREK LEWETNIVYK EAKESVDALF VNSQYDRLQA DTNIAMIHAA DKRVHSIREA  900
YLPELSVIPG VNAAIFEELE GRIFTAFSLY DARNVIKNGD FNNGLSCWNV KGHVDVEEQN  960
NHRSVLVVPE WEAEVSQEVR VCPGRGYILR VTAYKEGYGE GCVTIHEIEN NTDELKFSNC  1020
VEEEVYPNNT VTCNDYTATQ EEYEGTYTSR NRGYDGAYES NSSVPADYAS AYEEKAYTDG  1080
RRDNPCESNR GYGDYTPLPA GYVTKELEYF PETDKVWIEI GETEGTFIVD SVELLLMEE   1139
```

```
SEQ ID NO: 19          moltype = DNA  length = 3420
FEATURE                Location/Qualifiers
misc_feature           1..3420
                       note = Nucleotide sequence used for expression in a
                        bacterial cellencoding TIC844_5.
source                 1..3420
                       mol_type = other DNA
                       organism = synthetic construct
SEQUENCE: 19
atggaaataa ataatcaaaa ccaatgtgtg ccttacaatt gtttaagtaa tcctaaggag  60
ataaatattag gcgaggaaag gctagaaaca gggaatactg tagcagacat ttcattaggg  120
cttattaatt ttctatattc taattttgta ccaggaggag gatttatagt aggtttacta  180
gaattaatat ggggatttat agggccttcg caatgggata ttttttagc tcaaattgag  240
caattgatta gtcaaagaat agaagaattt gctaggaatc aggcaatttc aagattggag  300
gggctaagca atctttataa ggtctatgtt agagcgttta gcgactggga gaaagatcct  360
actaatcctg ctttaaggga agaaatgcgt atacaattta atgacatgaa tagtgctctc  420
ataacggcta ttccactttt tagagttcaa aattatgaag ttgctctttt atctgtatat  480
```

-continued

```
gttcaagccg caaacttaca tttatctatt ttaagggatg tttcagtttt cggagaaaga  540
tggggatatg atacagcgac tatcaataat cgctatagtg atctgactag ccttattcat  600
gtttatacta accattgtgt ggatacgtat aatcagggat taaggcgttt ggaaggtcgt  660
tttcttagcg attggattgt atataatcgt ttccggagac aattgacaat ttcagtatta  720
gatattgttg cgtttttcc aaattatgat attagaacat atccaattca aacagctact  780
cagctaacga gggaagtcta tctggattta cctttatta atgaaaatct ttctcctgca  840
gcaaaatatc caacctttc agctgctgaa agtgctataa ttagaagtcc tcatttagta  900
gacttttaa atagctttac catttataca gatagtctgg cacgttctgc atattgggga  960
gggcacttgg taaattcttt ccgcacagga accactacta atttgataag atcccttta  1020
tatggaaggg aaggaaatac agagcgcccc gtaactatta ccgcatcacc tagcgtacca  1080
atatttagaa cactttcata tccaacaggc cttgacaatt caaatcctgt agctggaatc  1140
gagggagtgg aattccaaaa tactataagt agaagtatct atcgtaaaag cggtccaata  1200
gattctttta gtgaattacc acctcaagat gccagcgtat ctcctgcaat tgggtatagt  1260
caccgtttat gccatgcaac atttttagaa cggattagtg gaccaagaat agcaggcacc  1320
gtattttctt ggacacaccg tagtgccagc cctactaacg aagtaagtcc atctagaatt  1380
acacaaattc catgggtaaa ggcgcatact cttgcatctg gtgcctccgt cattaaaggt  1440
cctggattta caggtggaga tattctgact aggaatagta tgggcgagct ggggacctta  1500
cgagtaacct tcacaggaag attaccacaa agttattata tacgtttccg ttatgcttcg  1560
gtagcaaata ggagtggtac atttagatat tcacagccac cttcgtatgg aatttcattt  1620
ccaaaaacta tggacgcagg tgaaccacta acatctcgtt cgttcgctca tacaacactc  1680
ttcactccaa taacctttc acgagctcaa gaagaatttg atctatacat ccaatcgggt  1740
gtttatatag atcgaattga atttataccg gttactgcaa catttgaggc agaatatgat  1800
ttagaaagag cacaaaaggc ggtgaatgag ctgtttactt cttccaatca aatcgggtta  1860
aaaacagatg tgacggatta tcatattgat caagtatcca atttagttga gtgtttatct  1920
gatgaatttt gtctggatga aaaaaaagaa ttgtccgaga aagtcaaaca tgcgaagcga  1980
cttagtgatg agcggaattt acttcaagat ccaaacttta gagggatcaa tagacaacta  2040
gaccgtggct ggagaggaag tacggatatt accatccaag gaggcgatga cgtattcaaa  2100
gagaattacg ttacgctatt gggtaccttt gatgagtgct atccaacgta tttatatcaa  2160
aaaatagatg agtcgaaatt aaaagcctat acccgttacc aattaagagg gtatatcgaa  2220
gatagtcaag acttagaaat ctatttaatt cgctacaatg ccaaacacga aacagtaaat  2280
gtgccaggta cgggttcctt atggccgctt tcagccccaa gtccaatcgg aaaatgtgcc  2340
catcattccc atcatttctc cttggacatt gatgttggat gtacagactt aaatgaggac  2400
ttaggtgtat gggtgatatt caagattaag acgcaagatg gccatgcaag actaggaaat  2460
ctagaatttc tcgaagagaa accattagta ggagaagcac tagctcgtgt gaaaagagcg  2520
gagaaaaaat ggagagacaa acgtgaaaaa ttggaatggg aaacaaatat tgtttataaa  2580
gaggcaaaag aatctgtaga tgctttattt gtaaactctc aatatgatag attacaagcg  2640
gataccaaca tcgcgatgat tcatgcggca gataaacgcg ttcatagcat tcgagaagct  2700
tatctgcctg agctgtctgt gattccgggt gtcaatgcgg ctatttttga agaattagaa  2760
gggcgtattt tcactgcatt ctccctatat gatgcgagaa atgtcattaa aaatggtgat  2820
tttaataatg gcttatcctg ctggaacgtg aaagggcatg tagatgtaga agaacaaaac  2880
aaccaccgtt cggtccttgt tgttccggaa tgggaagcag aagtgtcaca agaagttcgt  2940
gtctgtccgg gtcgtggcta tatccttcgt gtcacagcgt acaaggaggg atatggagaa  3000
ggttgcgtaa ccattcatga gatcgagaac aatacagacg aactgaagtt tagcaactgt  3060
gtagaagagg aagtatatcc aaacaacacg gtaacgtgta atgattatac tgcgactcaa  3120
gaagaatatg agggtacgta cacttctcgt aatcgaggat atgacggagc ctatgaaagc  3180
aattcttctg taccagctga ttatgcatca gcctatgaag aaaaagcata tacagatgga  3240
cgaagagaca atccttgtga atctaacaga ggatatgggg attacacacc actaccagct  3300
ggctatgtga caaaagaatt agagtacttc ccagaaaccg ataaggtatg gattgagatc  3360
ggagaaacgg aaggaacatt catcgtggac agcgtggaat tacttcttat ggaggaatag  3420
```

```
SEQ ID NO: 20            moltype = AA  length = 1139
FEATURE                  Location/Qualifiers
REGION                   1..1139
                         note = Amino acid sequence of the engineered insecticidal
                          chimericprotein TIC844_5.
source                   1..1139
                         mol_type = protein
                         organism = synthetic construct
SEQUENCE: 20
MEINNQNQCV PYNCLSNPKE IILGEERLET GNTVADISLG LINFLYSNFV PGGGFIVGLL  60
ELIWGFIGPS QWDIFLAQIE QLISQRIEEF ARNQAISRLE GLSNLYKVYV RAFSDWEKDP  120
TNPALREEMR IQFNDMNSAL ITAIPLFRVQ NYEVALLSVY VQAANLHLSI LRDVSVFGER  180
WGYDTATINN RYSDLTSLIH VYTNHCVDTY NQGLRRLEGR FLSDWIVYNR FRRQLTISVL  240
DIVAFFPNYD IRTYPIQTAT QLTREVYLDL PFINENLSPA AKYPTFSAAE SAIIRSPHLV  300
DFLNSFTIYT DSLARSAYWG GHLVNSFRTG TTTNLIRSPL YGREGNTERP VTITASPSVP  360
IFRTLSYPTG LDNSNPVAGI EGVEFQNTIS RSIYRKSGPI DSFSELPPQD ASVSPAIGYS  420
HRLCHATFLE RISGPRIAGT VFSWTHRSAS PTNEVSPSRI TQIPWVKAHT LASGASVIKG  480
PGFTGGDILT RNSMGELGTL RVTFTGRLPQ SYYIRFRYAS VANRSGTFRY SQPPSYGISF  540
PKTMDAGEPL TSRSFAHTTL FTPITFSRAQ EEFDLYIQSG VYIDRIEFIP VTATFEAEYD  600
LERAQKAVNE LFTSSNQIGL KTDVTDYHID QVSNLVECLS DEFCLDEKKE LSEKVKHAKR  660
LSDERNLLQD PNFRGINRQL DRGWRGSTDI TIQGGDDVFK ENYVTLLGTF DECYPTYLYQ  720
KIDESKLKAY TRYQLRGYIE DSQDLEIYLI RYNAKHETVN VPGTGSLWPL SAPSPIGKCA  780
HHSHHFSLDI DVGCTDLNED LGVWVIFKIK TQDGHARLGN LEFLEEKPLV GEALARVKRA  840
EKKWRDKREK LEWETNIVYK EAKESVDALF VNSQYDRLQA DTNIAMIHAA DKRVHSIREA  900
YLPELSVIPG VNAAIFEELE GRIFTAFSLY DARNVIKNGD FNNGLSCWNV KGHVDVEEQN  960
NHRSVLVVPE WEAEVSQEVR VCPGRGYILR VTAYKEGYGE GCVTIHEIEN NTDELKFSNC  1020
VEEEVYPNNT VTCNDYTATQ EEYEGTYTSR NRGYDGAYES NSSVPADYAS AYEEKAYTDG  1080
RRDNPCESNR GYGDYTPLPA GYVTKELEYF PETDKVWIEI GETEGTFIVD SVELLLMEE   1139
```

| SEQ ID NO: 21 | moltype = DNA length = 3420 |
|---|---|
| FEATURE | Location/Qualifiers |
| misc_feature | 1..3420 |
| | note = Nucleotide sequence used for expression in a bacterial cellencoding TIC844_6. |
| source | 1..3420 |
| | mol_type = other DNA |
| | organism = synthetic construct |

SEQUENCE: 21

```
atggaaataa ataatcaaaa ccaatgtgtg ccttacaatt gtttaagtaa tcctaaggag   60
ataatattag gcgaggaaag gctagaaaca gggaatactg tagcagacat ttcattaggg  120
cttattaatt ttctatattc taattttgta ccaggaggag gatttatagt aggtttacta  180
gaattaatat ggggatttat agggccttcg caatgggata tttttttagc tcaaattgag  240
caattgatta gtcaaagaat agaagaattt gctaggaata aggcaatttc aagattggag  300
gggctaagca atctttataa ggtctatgtt agagcgttta gcgactggga aaagatcct   360
actaatcctg ctttaaggga gaaatgcgt atacaattta tgacatgaa tagtgctctc   420
ataacggcta ttccactttt tagagttcaa aattatgaag ttgctctttt atctgtatat  480
gttcaagccg caaacttaca tttatctatt taagggatg tttcagtttc cggagaaaga  540
tggggatatg atacagcgac tatcaataat cgctatagtg atctgactag ccttattcat  600
gtttatacta accattgtgt ggatacgtat aatcagggat taaggcgttt ggaaggtcgt  660
tttcttagcg attggattgt atataatcgt ttccggagac aattgacaat ttcagtatta  720
gatattgttg cgttttttcc aaattatgat attagaacta atccaattca aacagctact  780
cagctaacga gggaagtcta tctgatttta cctttatta atgaaaatct ttctcctgca   840
gcaagctatc caacctttc agctgctgaa agtgctataa ttagaagtcc tcatttagta   900
gacttttttaa atagctttac catttataca gatagtctgg cacgttatgc atattgggga  960
gggcacttgg taaattcttt ccgcacagga accactacta atttgataag atccccttta 1020
tatggaaggg aaggaaatac agagcgcccc gtaactatta ccgcatcacc tagcgtacca 1080
atatttagaa cactttcata tattacaggc cttgacaatc gtaatcctgt agctggaatc 1140
gagggagtgg aattccaaaa tactataagt agaagtatct atcgtaaaag cggtccaata 1200
gattctttta gtgaattacc acctcaagat gccagcgtat ctcctgcaat tgggtatagt 1260
caccgtttat gccatgcaac atttttagaa cggattagtg gaccaagaat agcaggcacc 1320
gtattttctt ggacacaccg tagtgccagc cctactaacg aagtaagtcc atctagaatt 1380
acacaaattc catgggtaaa ggcgcatact cttgcatctg tgcctccgt cattaaaggt 1440
cctggattta caggtggaga tattctgact aggaatagta tgggcgagct ggggaccta  1500
cgagtaacct tcacaggaag attaccacac agttattata tacgtttcg ttatgcttcg  1560
gtagcaaata ggagtggtac atttagatat tcacagccac cttcgtatgg aatttcattt 1620
ccaaaaacta tggacgcagg tgaaccacta acatctcgtt cgttcgctca tacaacactc 1680
ttcactccaa taccttttc acgagttcaa gaagaatttg atctatacat ccaatggggt 1740
gtttatatag atcgaattga atttataccg gttactgcaa catttgaggc agaatatgat 1800
ttagaaagag cacaaaaggc ggtgaatgag ctgtttactt cttccaatca aatcgggtta 1860
aaaacagatg tgacggatta tcatattgat caagtatcca atttagttga gtgtttatct 1920
gatgaatttt gtctggatga aaaaaagaa ttgtccgaga agtcaaaca tgcgaagcga  1980
cttagtgatg agcggaattt acttcaagat ccaaactta gagggatcaa tagacaacta 2040
gaccgtggct ggagaggaag tacgatatt accatccaag gaggcgatga cgtattcaaa 2100
gagaattacg ttacgctatt gggtaccttt gatgagtgct atccaacgta tttatatcaa 2160
aaaatagatg agtcgaaatt aaaagcctat acccgttacc aattaagagg gtatatcgaa 2220
gatgtcaag acttagaata ctatttaatt cgctacaatg ccaaacacga aacagtaaat 2280
gtgccaggta cgggttcctt atggccgctt tcagccccaa gtccaatcgg aaaatgtgcc 2340
catcattccc atcatttctc cttggacatt gatgttggat gtacagactt aaatgaggac 2400
ttaggtgtat gggtgatatt caagattaag acgcaagatg ccatgcaag actaggaaat 2460
ctagaatttc tcgaagagaa accattagta ggagaagcac tagctcgtgt gaaaaggcg  2520
gagaaaaaat ggagagacaa acgtgaaaaa ttggaatggg aaacaaatat tgtttataaa 2580
gaggcaaaag aatctgtaga tgctttattt gtaaactctc aatatgatag attacaagcg 2640
gataccaaca tcgcgatgat tcatgcggca gataaacgcg ttcatagcat tcgagaagct 2700
tatctgcctg agctgtctgt gattccgggt gtcaatgcg ctatttttga agaattagaa  2760
gggcgtattt tcactgcatt ctccctatat gatgcgagaa atgtcattaa aaatggtgat 2820
tttaataatg gttatcctg ctggaacgtg aaagggcatg tagatgtaga agaacaaaac  2880
aaccaccgtt cggtccttgt tgttccgaa tgggaagcag aagtgtcaca agaagttcgt  2940
gtctgtccgg gtcgtggcta tatccttcgt gtcacagcgt acaaggaggg atatggagaa 3000
ggttgcgtaa ccattcatga gatcgagaac aatacagacg aactgaagtt tagcaactgt 3060
gtagaagagg aagtatatcc aaacaacacg gtaacgtgta atgattatac tgcgactcaa 3120
gaagaatatg agggtacgta cacttctcgt aatcgaggat atgacggagc ctatgaaagc 3180
aattcttctg taccagctga ttatgcatca gcctatgaag aaaaagcata tacagatgga 3240
cgaagagaca atccttgtga atctaacaga ggatatggtg attacacacc actaccagct 3300
ggctatgtga caaagaatt agagtacttc ccagaaaccg ataaggtatg gattgagatc 3360
ggagaaacgg aaggaacatt catccgtgga cagcgtgaat tacttcttat ggaggaatag 3420
```

| SEQ ID NO: 22 | moltype = AA length = 1139 |
|---|---|
| FEATURE | Location/Qualifiers |
| REGION | 1..1139 |
| | note = Amino acid sequence of the engineered insecticidal chimericprotein TIC844_6. |
| source | 1..1139 |
| | mol_type = protein |
| | organism = synthetic construct |

SEQUENCE: 22

```
MEINNQNQCV PYNCLSNPKE IILGEERLET GNTVADISLG LINFLYSNFV PGGGFIVGLL   60
ELIWGFIGPS QWDIFLAQIE QLISQRIEEF ARNQAISRLE GLSNLYKVYV RAFSDWEKDP  120
TNPALREEMR IQFNDMNSAL ITAIPLFRVQ NYEVALLSVY VQAANLHLSI LRDVSVFGER  180
```

```
WGYDTATINN RYSDLTSLIH VYTNHCVDTY NQGLRRLEGR FLSDWIVYNR FRRQLTISVL    240
DIVAFFPNYD IRTYPIQTAT QLTREVYLDL PFINENLSPA ASYPTFSAAE SAIIRSPHLV    300
DPLNSFTIYT DSLARYAYWG GHLVNSFRTG TTTNLIRSPL YGREGNTERP VTITASPSVP    360
IFRTLSYITG LDNRNPVAGI EGVEFQNTIS RSIYRKSGPI DSFSELPPQD ASVSPAIGYS    420
HRLCHATFLE RISGPRIAGT VFSWTHRSAS PTNEVSPSRI TQIPWVKAHT LASGASVIKG    480
PGFTGGDILT RNSMGELGTL RVTFTGRLPQ SYYIRFRYAS VANRSGTFRY SQPPSYGISF    540
PKTMDAGEPL TSRSFAHTTL FTPITFSRAQ EEFDLYIQSG VYIDRIEFIP VTATFEAEYD    600
LERAQKAVNE LFTSSNQIGL KTDVTDYHID QVSNLVECLS DEFCLDEKKE LSEKVKHAKR    660
LSDERNLLQD PNFRGINRQL DRGWRGSTDI TIQGGDDVFK ENYVTLLGTF DECYPTYLYQ    720
KIDESKLKAY TRYQLRGYIE DSQDLEIYLI RYNAKHETVN VPGTGSLWPL SAPSPIGKCA    780
HHSHHFSLDI DVGCTDLNED LGVWVIFKIK TQDGHARLGN LEFLEEKPLV GEALARVKRA    840
EKKWRDKREK LEWETNIVYK EAKESVDALF VNSQYDRLQA DTNIAMIHAA DKRVHSIREA    900
YLPELSVIPG VNAAIFEELE GRIFTAFSLY DARNVIKNGD FNNGLSCWNV KGHVDVEEQN    960
NHRSVLVVPE WEAEVSQEVR VCPGRGYILR VTAYKEGYGE GCVTIHEIEN NTDELKFSNC   1020
VEEEVYPNNT VTCNDYTATQ EEYEGTYTSR NRGYDGAYES NSSVPADYAS AYEEKAYTDG   1080
RRDNPCESNR GYGDYTPLPA GYVTKELEYF PETDKVWIEI GETEGTFIVD SVELLLMEE    1139

SEQ ID NO: 23         moltype = DNA  length = 3420
FEATURE               Location/Qualifiers
misc_feature          1..3420
                      note = Nucleotide sequence used for expression in a
                      bacterial cellencoding TIC844_7.
source                1..3420
                      mol_type = other DNA
                      organism = synthetic construct
SEQUENCE: 23
atggaaataa ataatcaaaa ccaatgtgtg ccttacaatt gtttaagtaa tcctaaggag     60
ataatattag gcgaggaaag gctagaaaca gggaatactg tagcagacat ttcattaggg    120
cttattaatt ttctatattc taattttgta ccaggaggag gatttatagt aggtttacta    180
gaattaatat ggggatttat agggccttcg caatggattt ttttttggc tcaaattgat    240
caattgatta gtcaaagaat agaagaattt gctaggaatc aggcaatttc aagattggag    300
gggctaagca atctttataa ggtctatgtt agagcgttta gcgactggga aaagatcct     360
actaatcctg ctttaaggga gaaatgcgt atacaattta tgacatgaa tagtgctctc     420
ataacggcta ttccacttt tagagttcaa aattatgaag ttgctctttt atctgtatat     480
gttcaagccg caaacttaca tttatctatt ttaaggagtg tttcagtttt cggagaaaga    540
tggggatatg atacagcgac tatcaataat cgctatagtg atctgactag cctttattcat   600
gtttatacta accattgtgt ggatacgtat aatcagggat taaggcgttt ggaaggtcgt    660
tttcttagcg attggattgt atataatcgt ttccggagac aattgacaat tcagtatta     720
gatattgttg cgttttttcc aaattatgat attagaacat atccaattca aacagctact    780
cagctaacga gggaagtcta tctgatttta cctttatta atgaaaatct ttctcctgca    840
gcaagctatc caacctttc agctgctgaa agtgctataa ttagaagtcc tcatttagta    900
gacttttta atagctttac catttataca gatagtctgg cacgttctgc atattgggga    960
gggcacttgg taaattcttt ccgcacagga accactacta atttgataag atccccttta   1020
tatgaagggg aaggaaatac agagcgcccc gtaactatta ccgcatcacc tagcgtacca   1080
atatttagaa cactttcata tagaacaggc cttgacaatt caaatcctgt agctggaatc   1140
gagggagtgg aattccaaaa tactataagt agaagtatct atcgtaaaag cggtccaata   1200
gattctttta gtgaattacc acctcaagat gccagcgtat ctcctgcaat tgggtatagt   1260
caccgtttat gccatgcaac atttttagaa cggattagtg gaccaagaat agcaggcacc   1320
gtattttctt ggacacaccg tagtgccagc cctactaacg aagtaagtcc atctagaatt   1380
acacaaattc catgggtaaa ggcgcatact cttgcatctg tgcctccgt cattaaaggt    1440
cctggattta caggtggaga tattctgact aggaatagta tgggcgagct gggaacctta   1500
cgagtaacct tcacaggaag attaccacac agttattata tacgtttccg ttatgcttcg   1560
gtagcaaata ggagtggtac atttagatat tcacagccac cttcgtatgg aatttcattt   1620
ccaaaaacta tggacgcagg tgaaccacta acatctcgtt cgttcgctca tacaacactc   1680
ttcactccaa taccttttc acgagctcaa gaagaatttg atctatacat ccaatcgggt   1740
gtttatatag atcgaattga atttataccg gttactgcaa catttgaggc agaatatgat   1800
ttagaaagag cacaaaaggc ggtgaatgag ctgtttactt cttccaatca aatcgggtta   1860
aaaacagatg tgacggatta tcatattgat caagtatcca atttagttga gtgttttatct  1920
gatgaatttt gtctggatga aaaaaagaa ttgtccgaga aagtcaaaca tgcgaagcga   1980
cttagtgatg agcggaattt acttcaagat ccaaacttta gagggatcaa tagacaacta   2040
gaccgtggct ggagaggaag tacggatatt accatccaag gaggcgatga cgtattcaaa   2100
gagaattacg ttacgctatt gggtaccttt gatgagtgct atccaacgta tttatatcaa   2160
aaaatagatg agtcgaaatt aaaagcctat acccgttacc aattaagagg gtatatcgaa   2220
gatgtcaag acttagaatg ctatttaatt cgctacaatg ccaaacacga aacagtaaat   2280
gtgccaggta cgggttcctt atggccgctt tcagccccaa gtccaatcgg aaaatgtgcc   2340
catcattccc atcatttctc cttggacatt gatgttggat gtacagactt aaatgaggac   2400
ttaggtgtat gggtgatatt caagattaag acgcaagatg gccatgcaag actaggaaat   2460
ctagaatttc tcgaagagaa accattagta ggagaagcac tagctcgtgt gaaaagagcg   2520
gagaaaaaat ggagagacaa acgtgaatggg aaacaaatat tgtttataaa                   2580
gaggcaaaag aatctgtaga tgcttttatt gtaaactctc aatatgatag attacaagcg   2640
gataccaaca tcgcgatgat tcatgcggca gataaacgcg ttcatagcat tcgaaagct    2700
tatctgcctg agctgtctgt gattccgggt gtcaatgcgg ctatttttga agaattagaa   2760
gggcgtattt tcactgcatt ctccctatat gatgcgagaa atgtcattaa aaatggtgat   2820
tttaataatg gcttatcctg ctggaacgtg aaagggcatg tagatgtaga aagcaaaac   2880
aaccaccgtt cggtccttgt tgttccgaaa tgggaagcag aagtgtcaca agaagttcgt    2940
gtctgtccgg gtcgtggcta tattcttcgt gtcacagcgt acaaggaggg atatggaaa    3000
ggttgcgtaa ccattcatga gatcgagaac aatacagacg aactgaagtt tagcaactgt   3060
gtagaagagg aagtatatcc aaacaacacg gtaacgtgta atgattatac tgcgactcaa   3120
gaagaatatg agggtacgta cacttctcgt aatcgggat atgacggagc ctatgaaagc   3180
```

```
aattcttctg taccagctga ttatgcatca gcctatgaag aaaaagcata tacagatgga 3240
cgaagagaca atccttgtga atctaacaga ggatatgggg attacacacc actaccagct 3300
ggctatgtga caaaagaatt agagtacttc ccagaaaccg ataaggtatg gattgagatc 3360
ggagaaacgg aaggaacatt catcgtggac agcgtggaat tacttcttat ggaggaatag 3420
```

| | | |
|---|---|---|
| SEQ ID NO: 24 | moltype = AA   length = 1139 | |
| FEATURE | Location/Qualifiers | |
| REGION | 1..1139 | |
| | note = Amino acid sequence of the engineered insecticidal chimericprotein TIC844_7. | |
| source | 1..1139 | |
| | mol_type = protein | |
| | organism = synthetic construct | |

SEQUENCE: 24
```
MEINNQNQCV PYNCLSNPKE IILGEERLET GNTVADISLG LINFLYSNFV PGGGFIVGLL   60
ELIWGFIGPS QWDIFLAQIE QLISQRIEEF ARNQAISRLE GLSNLYKVYV RAFSDWEKDP  120
TNPALREEMR IQFNDMNSAL ITAIPLFRVQ NYEVALLSVY VQAANLHLSI LRDVSVFGER  180
WGYDTATINN RYSDLTSLIH VYTNHCVDTY NQGLRRLEGR FLSDWIVYNR FRRQLTISVL  240
DIVAFFPNYD IRTYPIQTAT QLTREVYLDL PFINENLSPA ASYPTFSAAE SAIIRSPHLV  300
DFLNSFTIYT DSLARSAYWG GHLVNSFRTG TTTNLIRSPL YGREGNTERP VTITASPSVP  360
IFRTLSYRTG LDNSNPVAGI EGVEFQNTIS RSIYRKSGPI DSFSELPPQD ASVSPAIGYS  420
HRLCHATFLE RISGPRIAGT VFSWTHRSAS PTNEVSPSRI TQIPWVKAHT LASGASVIKG  480
PGFTGGDILT RNSMGELGTL RVTFTGRLPQ SYYIRFRYAS VANRSGTFRY SQPPSYGISF  540
PKTMDAGEPL TSRSFAHTTL FTPITFSRAQ EEFDLYIQSG VYIDRIEFIP VTATFEAEYD  600
LERAQKAVNE LFTSSNQIGL KTDVTDYHID QVSNLVECLS DEFCLDEKKE LSEKVKHAKR  660
LSDERNLLQD PNFRGINRQL DRGWRGSTDI TIQGGDDVFK ENYVTLLGTF DECYPTYLYQ  720
KIDESKLKAY TRYQLRGYIE DSQDLEIYLI RYNAKHETVN VPGTGSLWPL SAPSPIGKCA  780
HHSHHFSLDI DVGCTDLNED LGVWVIFKIK TQDGHARLGN LEFLEEKPLV GEALARVKRA  840
EKKWRDKREK LEWETNIVYK EAKESVDALF VNSQYDRLQA DTNIAMIHAA DKRVHSIREA  900
YLPELSVIPG VNAAIFEELE GRIFTAFSLY DARNVIKNGD FNNGLSCWNV KGHVDVEEQN  960
NHRSVLVVPE WEAEVSQEVR VCPGRGYILR VTAYKEGYGE GCVTIHEIEN NTDELKFSNC 1020
VEEEVYPNNT VTCNDYTATQ EEYEGTYTSR NRGYDGAYES NSSVPADYAS AYEEKAYTDG 1080
RRDNPCESNR GYGDYTPLPA GYVTKELEYF PETDKVWIEI GETEGTFIVD SVELLLMEE  1139
```

| | | |
|---|---|---|
| SEQ ID NO: 25 | moltype = DNA   length = 3420 | |
| FEATURE | Location/Qualifiers | |
| misc_feature | 1..3420 | |
| | note = Nucleotide sequence used for expression in a bacterial cellencoding TIC844_8. | |
| source | 1..3420 | |
| | mol_type = other DNA | |
| | organism = synthetic construct | |

SEQUENCE: 25
```
atggaaataa ataatcaaaa ccaatgtgtg ccttacaatt gtttaagtaa tcctaaggag   60
ataatattag gcgaggaaag gctagaaaca gggaatactg tagcagacat ttcattaggg  120
cttattaatt ttctatattc aaattttgta ccaggaggag gatttatagt aggtttacta  180
gaattaatat ggggatttat agggccttcg caatggatat ttttttttagc tcaaattgag  240
caattgatta gtcaaagaat agaagaattt gctaggaatc aggcaatttc aagattggag  300
gggctaagca atcttataaa ggtctatgtt agacgtttta gcgactggga aaagatcct  360
actaatcctg ctttaaggga gaaaatgcgt atacaattta tgacatgaa tagtgctctc  420
ataacgcta ttccacttttt tagagttcaa aattatgaag ttgctcttttt atctgtatat  480
gttcaagccg caaacttaca tttatctatt ttaagggatg tttcagtttt cggagaagga  540
tggggatatg atacagcgac tataataat cgctatagtg atctgactag ccttattcat  600
gtttatacta accattgtgt ggatacgtat aatcaggat taaggcgttt ggaaggtcgt  660
tttcttagcg attggattgt atataatcgt ttccggagac aattgacaat ttcagtatta  720
gatattgttg cgttttttcc aaattatgat attagaacat atccaattca aacagctact  780
cagctaacga gggaagtcta tctggattta cctttttatta atgaaaatct ttctcctgca  840
gcagtatatc caacctttc agctgctgaa agtgctataa ttagaagtcc tcattagta  900
gacttttaa atagctttac catttataca gatagtctgg cacgttctgc atattgggga  960
gggcacttgg taaattcttt ccgcacagga accactacta atttgataag atcccctta 1020
tatgaagg aaggaaatac agagcgcccc gtaactatta ccgcatcacc tagcgtacca 1080
atatttagaa cactttcata tccaacaggc cttgacaatt caaatcctgt agctggaatc 1140
gagggagtgg aattccaaaa tactatagtt agaagtatct atcgtaaaag cggtccaata 1200
gattcttta gtgaattacc acctcaagat gccagcgtat ctcctgcaat tgggtatgt 1260
caccgtttat gccatgcaac attttttagaa cggattagtg gaccaagaat agcaggcacc 1320
gtattttctt ggacacaccg tagtgccagc cctactaacg aagtaagtcc atctagaatt 1380
acacaaattc catgggtaaa ggcgcatact cttgcatctg gtgcctccgt cattaaaggt 1440
cctggattta caggtggaga tattctgact aggaatagta tgggcgagct ggggaccta 1500
cgagtaacct tcacaggaag attaccacac agttattata tacgtttccg ttatgcttcg 1560
gtagcaaata ggagtggtac atttagatat tcacagccac cttcgtatgg aatttcattt 1620
ccaaaaacta tggacgcagg tgaaccacta acatctcgtt cgttcgctca tacaacactc 1680
ttcactccaa taacctttc acgagctcaa gaagaatttg atctatacat ccaatcgggt 1740
gtttatatag atcgaattga atttataccg gttactgcaa catttgaggc agaatatgat 1800
ttagaaagga cacaaaaggc ggtgaatgag ctgttttacctt cttccaatca aatcgggtta 1860
aaaacagatg tgacggatta tcatattgat caagtatcca atttagttga gtgtttatct 1920
gatgaatttt gtctggatga aaaaaagaa ttgtccgaga aagtcaaaca tgcgaagcga 1980
cttagtgatg agcggaattt acttcaagat ccaaacttta gagggatcaa tagacaacta 2040
gaccgtggct ggagaggaag tacgatatt accatccaag gaggcgatga cgtattcaaa 2100
gagaattacg ttacgctatt gggtaccttt gatgagtgct atccaacgta tttatatcaa 2160
```

-continued

```
aaaatagatg agtcgaaatt aaaagcctat acccgttacc aattaagagg gtatatcgaa    2220
gatagtcaag acttagaaat ctatttaatt cgctacaatg ccaaacacga aacagtaaat    2280
gtgccaggta cgggttcctt atggccgctt tcagccccaa gtccaatcgg aaaatgtgcc    2340
catcattccc atcatttctc cttgacatt gatgttggat gtacagactt aaatgaggac     2400
ttaggtgtat gggtgatatt caagattaag acgcaagatg gccatgcaag actaggaaat    2460
ctagaatttc tcgaagagaa accattagta ggagaagcac tagctcgtgt gaaaagagcg    2520
gagaaaaaat ggagagacaa acgtgaaaaa ttggaatggg aaacaaatat tgtttataaa    2580
gaggcaaaag aatctgtaga tgctttattt gtaaactctc aatatgatag attacaagcg    2640
gataccaaca tcgcgatgat tcatgcggca gataaacgcg ttcatagcat tcgagaagct    2700
tatctgcctg agctgtctgt gattcgggt gtcaatgccg ctattttga agaattagaa      2760
gggcgtattt tcactgcatt ctccctatat gatgcgagaa atgtcattaa aaatggtgat    2820
tttaataatg gcttatcctg ctggaacgtg aaagggcatg tagatgtaga agaacaaaac    2880
aaccaccgtt cggtccttgt tgttccggaa tgggaagcag aagtgtcaca agaagttcgt    2940
gtctgtccgg gtcgtggcta tatccttcgt gtcacacgt acaaggaggg atatggagaa    3000
ggttgcgtaa ccattcatga gatcgagaac aatacagacg aactgaagtt tagcaactgt    3060
gtagaagagg aagtatatcc aaacaacacg gtaacgtgta atgattatac tgcgactcaa    3120
gaagaatatg agggtacgta cacttctcgt aatcgaggat atgacggagc ctatgaaagc    3180
aattcttctg taccagctga ttatgcatca gcctatgaag aaaaagcata tacagatgga    3240
cgaagagaca atccttgtga atctaacaga ggatatgggg attacacacc actaccagct    3300
ggctatgtga caaagaatt agagtacttc ccagaaaccg ataaggtatg gattgagatc    3360
ggagaaacgg aaggaacatt catccgtgga cagcgtgaat tacttcttat ggaggaatag    3420
```

```
SEQ ID NO: 26           moltype = AA   length = 1139
FEATURE                 Location/Qualifiers
REGION                  1..1139
                        note = Amino acid sequence of the engineered insecticidal
                          chimericprotein TIC844_8.
source                  1..1139
                        mol_type = protein
                        organism = synthetic construct
SEQUENCE: 26
MEINNQNQCV PYNCLSNPKE IILGEERLET GNTVADISLG LINFLYSNFV PGGGFIVGLL   60
ELIWGFIGPS QWDIFLAQIE QLISQRIEEF ARNQAISRLE GLSNLYKVYV RAFSDWEKDP   120
TNPALREEMR IQFNDMNSAL ITAIPLFRVQ NYEVALLSVR VQAANLHLSI LRDVSVFGER   180
WGYDTATINN RYSDLTSLIH VYTNHCVDTY NQGLRRLEGR FLSDWIVYNR FRRQLTISVL   240
DIVAFFPNYD IRTYPIQTAT QLTREVYLDL PFINENLSPA AVYPTFSAAE SAIIRSPHLV   300
DFLNSFTIYT DSLARSAYWG GHLVNSFRTG TTTNLIRSPL YGREGNTERP VTITASPSVP   360
IFRTLSYPTG LDNSNPVAGI EGVEFQNTIS RSIYRKSGPI DSFSELPPQD ASVSPAIGYS   420
HRLCHATFLE RISGPRIAGT VFSWTHRSAS PTNEVSPSRI TQIPWVKAHT LASGASVIKG   480
PGFTGGDILT RNSMGELGTL RVTFTGRLPQ SYYIRFRYAS VANRSGTFRY SQPPSYGISF   540
PKTMDAGEPL TSRSFAHTTL FTPITFSRAQ EEFDLYIQSG VYIDRIEFIP VTATFEAEYD   600
LERAQKAVNE LFTSSNQIGL KTDVTDYHID QVSNLVECLS DEFCLDEKKE LSEKVKHAKR   660
LSDERNLLQD PNFRGINRQL DRGWRGSTDI TIQGGDHVFK ENYVTLLGTF DECYPTYLYQ   720
KIDESKLKAY TRYQLRGYIE DSQDLEIYLI RYNAKHETVN VPGTGSLWPL SAPSPIGKCA   780
HHSHHFSLDI DVGCTDLNED LGVWVIFKIK TQDGHARLGN LEFLEEKPLV GEALARVKRA   840
EKKWRDKREK LEWETNIVYK EAKESVDALF VNSQYDRLQA DTNIAMIHAA DKRVHSIREA   900
YLPELSVIPG VNAAIFEELE GRIFTAFSLY DARNVIKNGD FNNGLSCWNV KGHVDVEEQN   960
NHRSVLVVPE WEAEVSQEVR VCPGRGYILR VTAYKEGYGE GCVTIHEIEN NTDELKFSNC   1020
VEEEVYPNNT VTCNDYTATQ EEYEGTYTSR NRGYDGAYES NSSVPADYAS AYEEKAYTDG   1080
RRDNPCESNR GYGDYTPLPA GYVTKELEYF PETDKVWIEI GETEGTFIVD SVELLLMEE    1139
```

```
SEQ ID NO: 27           moltype = DNA   length = 3498
FEATURE                 Location/Qualifiers
misc_feature            1..3498
                        note = Synthetic DNA sequence designed for plant expression
                          encodingCry1Da1.
source                  1..3498
                        mol_type = other DNA
                        organism = synthetic construct
SEQUENCE: 27
atggagatca acaaccagaa ccagtgcgtc ccgtacaact gcctgagcaa ccctaaggag    60
atcatcctgg gtgaggaacg cctggagacc ggcaacaccg tagccgacat tagcctgggc    120
ctcatcaact tcctctacag caacttcgtg cccggcggtg gcttcatcgt gggcctcctg    180
gagcttatct ggggcttcat cggccgtcc cagtcggaca tcttcctcgc ccagatcgaa    240
caactgatca gccagcggat cgaggagttc gctaggaacc aggccatctc cgcctggag    300
ggactctcca acctctacaa ggtgtacgtg cgcgcgttca gcgactggga aaggaccccg    360
accaaccccg ccctccgcga ggaaatgcgt atccagttca acgatatgaa ctcggccctc    420
atcaccgcca tcccgctctt ccgcgtgcag aactacgagg tggcccctcct gtccgtgtac    480
gttcaagccg ccaacctcca cctctccatc ctccgcgacg tgagcgtgtt cggcgagcgc    540
tgggctacg acaccgccac catcaacaac cgctactacg acctcacctc cctcatccac    600
gtttacacca accactgcgt ggacacgtac aaccagggcc tccgccgcct ggagggccgc    660
ttcctctccg actggatcgt gtacaaccgc ttcgcccgcc agctcaccat ctccgtcctg    720
gacatcgtcg cctttttccc caactacgac atccgcacct acctatcca gaccgccacc    780
cagctcaccc gcgaggtcta cctcgacctc ccgttcatca acgagaacct ctcccctgca    840
gccagctacc cgaccttctc cgccgctgag tccgccatca ttcgcagccc gcacctcgtg    900
gacttcctca actccttcac catctacacc gactcctcg cccgctacgc ctactggggc    960
ggtcacctcg tgaactcctt ccgcaccggc accactacca acctcatccg cagcccgctc    1020
tacggccgcg agggcaacac cgagcgcccg gtgaccatca ccgccagccc gagcgtgccc    1080
atcttccgca ccctcagcta catcaccggc ctggacaaca gcaaccctgt ggcgggcatc    1140
```

-continued

```
gagggcgtgg agttccagaa caccatctcc aggagcatct accgcaagag cggccctatc  1200
gacagcttca gcgagctgcc tcctcaggac gccagcgtga gccctgccat cggctacagc  1260
cacaggctgt gccacgccac cttcctggag cgcatcagcg gccctcgcat cgcgggcacc  1320
gtgttctcgt ggacccaccg cagcgcctct cctacgaacg aggtgtctcc tagtcgcatc  1380
acccagatcc cttgggtcaa ggcccacacc ctggctagtg gcgctagtgt catcaagggc  1440
cctggcttca ccggtggtga catcctgacc aggaactcta tgggcgagct gggcactctg  1500
agggtcactt tcactggccg cctgcctcag tcttactaca tccgcttccg ctacgctagt  1560
gtcgctaacc gctctggtac tttccgctac tctcagcctc cgtcttacgg tatctctttc  1620
cctaagacta tggacgctgg tgagcctctg accagtagga gcttcgctca cactactctg  1680
ttcactccta tcactttctc tagggctcag gaggagttcg acctgtacat ccagtctggt  1740
gtgtacatcg acaggatcga gttcatcccc gtgaccgcca cgttcgaggc cgagtacgac  1800
cttgagcgcg cccagaaggt ggtgaacgcc ctcttcacta gcactaacca gctaggcctg  1860
aagactgacg tgaccgacta ccacatcgac caagtgagca acctagtggc ctgcctctcc  1920
gacgagttct gcctcgacga gaagcgcgag ctgtccgaga aggtgaagca cgccaagcgc  1980
ctctccgacg agcgcaacct gctccaggac cccaacttca ggggcatcaa caggcagccc  2040
gaccgcggct ggcgcggctc caccgacatc accatccagg gcggtgacga cgtattcaag  2100
gagaactacg ttaccctccc cggcaccttc gacgagtgtt accccaccta cctctaccag  2160
aagatcgacg agtccaagct gaaggcctac acccgctacc agctccgcgg ctacatcgag  2220
gactcccagg acctggaaat ctacctcatc cgctacaacg ccaagcacga gatcgtgaac  2280
gtgcctggca ccggcagcct ctggcctctc agcgtggaga accagatcgg cccttgcggc  2340
gagcctaacc gctgcgcccc tcacctcgag tggaaccctg acctccactg ctcgtgcagg  2400
gacggcgaga agtgcgccca ccatagccac cacttctctc tggacatcga cgtgggctgc  2460
accgacctga acgaggacct gggcgtgtgg gttatcttca agatcaagac ccaggacggt  2520
cacgccaggc tgggtaacct ggagttcctt gaggaaaagc ctctgctggg tgaggccctg  2580
gccagggtca agagggctga gaagaaatgg agggataaga gggagaccct gcagctggag  2640
accactatcg tctacaagga ggctaaggag tctgtcgatg ctctgttcgt caactctcag  2700
tacgatagac tgcaagctga taccaacatc gctatgatcc acgctgcgga taagcgggtc  2760
caccggatcc gggaggctta ccttccggag ctttctgtca tcccgggtgt caacgctgcg  2820
atcttcgagg aacttgagga acggatcttc actgcgttta gtctttacga tgcgcggaac  2880
atcatcaaga acggggactt caacaatggt ctgctgtgct ggaacgtcaa gggtcatgtc  2940
gaggtcgagg aacaaaacaa tcatcgtagt gtccttgtca ttcctgagtg ggaggcggag  3000
gtctctcaag aggtccgtgt ttgcccgggg cgtgggtaca ttcttcgtgt tactgcgtac  3060
aaggaggggt acggggaggg gtgcgttact attcatgaga ttgagaacaa tactgatgag  3120
cttaagttca acaattgtgt tgaggaggag gtttacccga acaatactgt tacgtgcatc  3180
aactacacgg caacgcaaga ggaatacgag gggacgtaca cctcgcgtaa tagagggtat  3240
gatgaggcgt acggaaacaa cccgtcggtt ccagcagatt atgcctcggt ttatgaggag  3300
aagtcgtaca cggatagacg acgcgagaat ccatgtgagt caaatcgagg atacggagat  3360
tacacaccat taccagcagg atacgttaca aaggagttgg aatacttccc ggaaacagat  3420
aaagtttgga ttgaaatcgg agaaacagaa ggaacattca tcgtcgactc agtagaattg  3480
ttgttgatgg aagaatga                                                3498

SEQ ID NO: 28           moltype = AA  length = 1165
FEATURE                 Location/Qualifiers
REGION                  1..1165
                        note = Amino acid sequence of Cry1Da1 encoded by a
                         synthetic DNAsequence.
source                  1..1165
                        mol_type = protein
                        organism = synthetic construct
SEQUENCE: 28
MEINNQNQCV PYNCLSNPKE IILGEERLET GNTVADISLG LINFLYSNFV PGGGFIVGLL  60
ELIWGFIGPS QWDIFLAQIE QLISQRIEEF ARNQAISRLE GLSNLYKVYV RAFSDWEKDP  120
TNPALREEMR IQFNDMNSAL ITAIPLFRVQ NYEVALLSVY VQAANLHLSI LRDVSVFGER  180
WGYDTATINN RYSDLTSLIH VYTNHCVDTY NQGLRRLEGR FLSDWIVYNR FRRQLTISVL  240
DIVAFFPNYD IRTYPIQTAT QLTREVYLDL PFINENLSPA ASYPTFSAAE SAIIRSPHLV  300
DFLNSFTIYT DSLARYAYWG GHLVNSFRTG TTTNLIRSPL YGREGNTERP VTITASPSVP  360
IFRTLSYITG LDNSNPVAGI EGVEFQNTIS RSIYRKSGPI DSFSELPPQD ASVSPAIGYS  420
HRLCHATFLE RISGPRIAGT VFSWTHRSAS PTNEVSPSRI TQIPWVKAHT LASGASVIKG  480
PGFTGGDILT RNSMGELGTL RVTFTGRLPQ SYYIRFRYAS VANRSGTFRY SQPPSYGISF  540
PKTMDAGEPL TSRSFAHTTL FTPITFSRAQ EEFDLYIQSG VYIDRIEFIP VTATFEAEYD  600
LERAQKVVNA LFTSTNQLGL KTDVTDYHID QVSNLVACLS DEFCLDEKRE LSEKVKHAKR  660
LSDERNLLQD PNFRGINRQP DRGWRGSTDI TIQGGDDVFK ENYVTLPGTF DECYPTYLYQ  720
KIDESKLKAY TRYQLRGYIE DSQDLEIYLI RYNAKHEIVN VPGTGSLWPL SVENQIGPCG  780
EPNRCAPHLE WNPDLHCSCR DGEKCAHHSH HFSLDIDVGC TDLNEDLGVW VIFKIKTQDG  840
HARLGNLEFL EEKPLLGEAL ARVKRAEKKW RDKRETLQLE TTIVYKEAKE SVDALFVNSQ  900
YDRLQADTNI AMIHAADKRV HRIREAYLPE LSVIPGVNAA IFEELEERIF TAFSLYDARN  960
IIKNGDFNNG LLCWNVKGHV EVEEQNNHRS VLVIPEWEAE VSQEVRVCPG RGYILRVTAY  1020
KEGYGEGCVT IHEIENNTDE LKFNNCVEEE VYPNNTVTCI NYTATQEEYE GTYTSRNRGY  1080
DEAYGNNPSV PADYASVYEE KSYTDRRREN PCESNRGYGD YTPLPAGYVT KELEYFPETD  1140
KVWIEIGETE GTFIVDSVEL LLMEE                                        1165

SEQ ID NO: 29           moltype = DNA  length = 3501
FEATURE                 Location/Qualifiers
misc_feature            1..3501
                        note = Synthetic DNA sequence designed for plant expression
                         encodingCry1Da1 with an additional Alanine residue
                         inserted at position2.
source                  1..3501
                        mol_type = other DNA
```

-continued organism = synthetic construct
SEQUENCE: 29
atggctgaga tcaacaacca gaaccagtgc gtcccgtaca actgcctgag caaccctaag 60
gagatcatcc tgggtgagga acgcctggag accggcaaca ccgtagccga cattagcctg 120
ggcctcatca acttcctcta cagcaacttc gtgcccggcg gtggcttcat cgtgggcctc 180
ctggagctta tctggggctt catcggcccg tcccagtggg acatcttcct cgcccagatc 240
gagcaactga tcagccagcg gatcgaggag ttcgctagga accaggccat ctcccgcctg 300
gagggactct ccaacctcta caaggtgtac gtgcgcgcgt tcagcgactg ggagaaggac 360
ccgaccaacc cggccctccg cgaggaaatg cgtatccagt tcaacgatat gaactcggcc 420
ctcatcaccg ccatcccgct cttccgcgtg cagaactacg aggtggccct cctgtccgtg 480
tacgttcaag ccgccaacct ccacctctcc atcctccgcg acgtgagcgt gttcggcgag 540
cgctggggct acgacaccgc caccatcaac aaccgctact ccgacctcac ctccctcatc 600
cacgtttaca ccaaccactg cgtggacacg tacaaccagg gcctccgccg cctggagggc 660
cgcttcctct ccgactggat cgtgtacaac cgcttccgcc gccagctcac catctccgtc 720
ctggacatcg tcgccttctt tcccaactac gacatccgca cctaccctat ccagaccgcc 780
acccagctca cccgcgaggt ctacctcgac ctcccgttca tcaacgagaa cctcagcccg 840
gccgccagct acccgacctt ctccgccgct gagtccgcca tcattcgcag cccgcacctc 900
gtggacttcc tcaactcctt caccatctac accgactccc tcgcccgcta cgcctactgg 960
ggcggtcacc tcgtgaactc cttccgcacc ggcaccacta ccaacctcat ccgcagcccg 1020
ctctacggcc gcgagggcaa caccgagcgc ccggtgacca tcaccgccag cccgagcgtg 1080
cccatcttcc gcaccctcag ctacatcacc ggcctggaca acagcaaccc tgtggcgggc 1140
atcgagggcg tggagttcca gaacaccatc tccaggagca tctaccgcaa gagcggccct 1200
atcgacagct tcagcgagct gcctcctcag gacgccagcg tgagccctgc catcggctac 1260
agccacaggc tgtgccacgc caccttcctg gagcgcatca gcggccctcg catcgcgggc 1320
accgtgttct cgtggaccca ccgcagcgcc tctcctacga acgaggtgtc tcctagtcgc 1380
atcacccaga tcccttgggt caaggcccac accctggcta gtggcgctag tgtcatcaag 1440
ggccctggct tcaccggtgg tgacatcctg accaggaact ctatgggcga gctgggcact 1500
ctgagggtca ctttcactgg ccgcctgcct cagtcttact acatccgctt ccgctacgct 1560
agtgtcgcta accgctctgg tactttccgc tactctcagc ctccgtctta cggtatctct 1620
ttccctaaga ctatggacgc tggtgagcct ctgaccagta ggagcttcgc tcacactact 1680
ctgttcactc ctatcacttt ctctagggct caggaggagt tcgacctgta catccagtct 1740
ggtgtgtaca tcgacaggat cgagttcatc cccgtgaccg ccacgttcga ggccgagtac 1800
gaccttgagc gcgcccagaa ggtggtgaac gccctcttca ctagcactaa ccagctaggc 1860
ctgaagactg acgtgaccga ctaccacatc gaccaagtga gcaacctagt ggcctgcctc 1920
tccgacgagt tctgcctcga cgagaagcgc gagctgtccg agaaggtgaa gcacgccaag 1980
cgcctctccg acgagcgcaa cctgctccag gaccccaact tcaggggcat caacaggcag 2040
cccgaccgcg gctggcgcgg ctccaccgac atcaccatcc agggcggtga cgacgtattc 2100
aaggagaact acgttaccct ccccggcacc ttcgacgagt gttaccccac ctacctctac 2160
cagaagatcg acgagtccaa gctgaaggcc tacacccgct accagctccg cggctacatc 2220
gaggactccc aggacctgga aatctacctc atccgctaca acgccaagca cgagatcgtg 2280
aacgtgcctg gcaccggcag cctctggcct ctcagcgtgg agaaccagat cggcccttgc 2340
ggcgagccta accgctgcgc ccctcacctc gagtggaacc ctgacctcca ctgctcgtgc 2400
agggacggcg agaagtgcgc ccaccatagc caccacttct ctctggacat cgacgtgggc 2460
tgcaccgacc tgaacgagga cctgggcgtg tgggttatct tcaagatcaa gacccaggac 2520
ggtcacgcca ggctgggtaa cctggagttc cttgaggaaa agcctctgct gggtgaggcc 2580
ctggccaggg tcaagagggc tgagaagaaa tggagggata agagggagac cctgcagctg 2640
gagaccacta tcgtctacaa ggaggctaag gagtctgtcg atgctctgtt cgtcaactct 2700
cagtacgata gactgcaagc tgataccaac atcgctatga tccacgctgc ggataagcgg 2760
gtccaccgga tccgggaggc ttaccttccg gagctttctg tcatcccggg tgtcaacgct 2820
gcgatcttcg aggaacttga ggaacggatc ttcactgcgt ttagtcttta cgatgcgcgg 2880
aacatcatca agaacgggga cttcaacaat ggtctgctgt gctggaacgt caagggtcat 2940
gtcgaggtcg aggaacaaaa caatcatcgt agtgtccttg tcattcctga gtgggaggcg 3000
gaggtctctc aagaggtccg tgtttgcccg ggcgtgggt acattcttcg tgttactgcg 3060
tacaaggagg ggtacgggga ggggtgcgtt actattcatg agattgagaa caatactgat 3120
gagcttaagt tcaacaattg tgttgaggag gaggtttacc cgaacaatac tgttacgtgc 3180
atcaactaca cggcaacgca agaggaatac gaggggacgt acacctcgcg taatagaggg 3240
tatgatgagg cgtacggaaa caacccgtcg gttccagcag attatgcctc ggtttatgag 3300
gagaagtcgt acacggatag acgacgcgag aatccatgtg agtcaaatcg aggatacgga 3360
gattacacac cattaccagc aggatacgtt acaaaggagt tggaatactt cccggaaaca 3420
gataaagttt ggattgaaat cggagaaaca gaaggaacat tcatcgtcga ctcagtagaa 3480
ttgttgttga tggaagaatg a 3501

SEQ ID NO: 30 moltype = AA length = 1166
FEATURE Location/Qualifiers
REGION 1..1166
note = Amino acid sequence of Cry1Da1 encoded by a synthetic DNAsequence wherein an additional Alanine residue has been insertedat position 2.
source 1..1166
mol_type = protein
organism = synthetic construct
SEQUENCE: 30
MAEINNQNQC VPYNCLSNPK EIILGEERLE TGNTVADISL GLINFLYSNF VPGGGFIVGL 60
LELIWGFIGP SQWDIFLAQI EQLISQRIEE FARNQAISRL EGLSNLYKVY VRAFSDWEKD 120
PTNPALREEM RIQFNDMNSA LITAIPLFRV QNYEVALLSV YVQAANLHLS ILRDVSVFGE 180
RWGYDTATIN NRYSDLTSLI HVYTNHCVDT YNQGLRRLEG RFLSDWIVYN RFRRQLTISV 240
LDIVAFFPNY DIRTYPIQTA TQLTREVYLD LPFINENLSP AASYPTFSAA ESAIIRSPHL 300
VDFLNSFTIY TDSLARYAYW GGHLVNSFRT GTTTNLIRSP LYGREGNTER PVTITASPSV 360
PIFRTLSYIT GLDNSNPVAG IEGVEFQNTI SRSIYRKSGP IDSFSELPPQ DASVSPAIGY 420

-continued

```
SHRLCHATFL ERISGPRIAG TVFSWTHRSA SPTNEVSPSR ITQIPWVKAH TLASGASVIK  480
GPGFTGGDIL TRNSMGELGT LRVTFTGRLP QSYYIRFRYA SVANRSGTFR YSQPPSYGIS  540
FPKTMDAGEP LTSRSFAHTT LFTPITFSRA QEEFDLYIQS GVYIDRIEFI PVTATFEAEY  600
DLERAQKVVN ALFTSTNQLG LKTDVTDYHI DQVSNLVACL SDEFCLDEKR ELSEKVKHAK  660
RLSDERNLLQ DPNFRGINRQ PDRGWRGSTD ITIQGGDDVF KENYVTLPGT FDECYPTYLY  720
QKIDESKLKA YTRYQLRGYI EDSQDLEIYL IRYNAKHEIV NVPGTGSLWP LSVENQIGPC  780
GEPNRCAPHL EWNPDLHCSC RDGEKCAHHS HHFSLDIDVG CTDLNEDLGV WVIFKIKTQD  840
GHARLGNLEF LEEKPLLGEA LARVKRAEKK WRDKRETLQL ETTIVYKEAK ESVDALFVNS  900
QYDRLQADTN IAMIHAADKR VHRIREAYLP ELSVIPGVNA AIFEELEERI FTAFSLYDAR  960
NIIKNGDFNN GLLCWNVKGH VEVEEQNNHR SVLVIPEWEA EVSQEVRVCP GRGYILRVTA  1020
YKEGYGEGCV TIHEIENNTD ELKFNNCVEE EVYPNNTVTC INYTATQEEY EGTYTSRNRG  1080
YDEAYGNNPS VPADYASVYE EKSYTDRRRE NPCESNRGYG DYTPLPAGYV TKELEYFPET  1140
DKVWIEIGET EGTFIVDSVE LLLMEE                                      1166

SEQ ID NO: 31          moltype = DNA  length = 3501
FEATURE                Location/Qualifiers
misc_feature           1..3501
                       note = Synthetic DNA sequence designed for plant expression
                        encodingCry1Da1_3 with an additional Alanine residue
                        inserted at position2.
source                 1..3501
                       mol_type = other DNA
                       organism = synthetic construct
SEQUENCE: 31
atggctgaga tcaacaacca gaaccagtgc gtcccgtaca actgcctgag caaccctaag  60
gagatcatcc tgggtgagga acgcctggag accggcaaca ccgtagccga cattagcctg  120
ggcctcatca acttcctcta cagcaacttc gtgcccggcg gtggcttcat cgtgggcctc  180
ctggagctta tctggggctt catcggcccg tcccagtggg acatcttcct cgcccagatc  240
gagcaactga tcagccagcg gatcgaggag ttcgctagga accaggccat ctcccgcctg  300
gagggactct ccaacctcta caaggtgtac gtgcgcgcgt tcagcgactg ggagaaggac  360
ccgaccaacc cggccctccg cgaggaaatg cgtatccagt tcaacgatat gaactcggcc  420
ctcatcaccg ccatcccgct cttccgcgtg cagaactacg aggtggccct cctgtccgtg  480
tacgttcaag ccgccaacct ccacctctcc atcctccgcg acgtgagcgt gttcggcgag  540
cgctggggct acgacaccgc caccatcaac aaccgctact ccgacctcac ctccctcatc  600
cacgtttaca ccaaccactg cgtggacacg tacaaccagg gcctccgccg cctggagggc  660
cgcttcctct ccgactggat cgtgtacaac cgcttccgcc gccagctcac catctccgtc  720
ctggacatcg tcgccttctt tcccaactac gacatccgca cctaccctat ccagaccgcc  780
acccagctca cccgcgaggt ctacctcgac ctcccgttca tcaacgagaa cctcagcccg  840
gccgccagct acccgacctt ctccgccgct gagtccgcca tcattcgcag cccgcacctc  900
gtggacttcc tcaactcctt caccatctac accgactccc tcgcccgcag cgcctactgg  960
ggcggtcacc tcgtgaactc cttccgcacc ggcaccacta ccaacctcat ccgcagcccg  1020
ctctacggcc gcgagggcaa caccgagcgc ccggtgacca tcaccgccag cccgagcgtg  1080
cccatcttcc gcaccctcag ctacatcacc ggcctggaca acagcaaccc tgtggcgggc  1140
atcgagggcg tggagttcca gaacaccatc tccaggagca tctaccgcaa gagcggccct  1200
atcgacagct tcagcgagct gcctcctcag gacgccagcg tgagccctgc catcggctac  1260
agccacaggc tgtgccacgc caccttcctg gagcgcatca gcggccctcg catcgcgggc  1320
accgtgttct cgtggaccca ccgcagcgcc tctcctacga acgaggtgtc tcctagtcgc  1380
atcacccaga tcccttgggt caaggcccac accctggcta gtggcgctag tgtcatcaag  1440
ggccctggct tcaccggtgg tgacatcctg accaggaact ctatgggcga gctgggcact  1500
ctgagggtca ctttcactgg ccgcctgcct cagtcttact acatccgctt ccgctacgct  1560
agtgtcgcta accgctctgg tactttccgc tactctcagc ctccgtctta cggtatctct  1620
ttccctaaga ctatggacgc tggtgagcct ctgaccagta ggagcttcgc tcacactact  1680
ctgttcactc ctatcacttt ctctagggct caggaggagt tcgacctgta catccagtct  1740
ggtgtgtaca tcgacaggat cgagttcatc cccgtgaccg ccacgttcga ggccgagtac  1800
gaccttgagc gcgcccagaa ggtggtgaac gccctcttca ctagcactaa ccagctaggc  1860
ctgaagactg acgtgaccga ctaccacatc gaccaagtga gcaacctagt ggcctgcctc  1920
tccgacgagt tctgcctcga cgagaagcgc gagctgtccg agaaggtgaa gcacgccaag  1980
cgcctctccg acgagcgcaa cctgctccag gaccccaact tcaggggcat caacaggcag  2040
cccgaccgcg gctggcgcgg ctccaccgac atcaccatcc agggcggtga cgacgtattc  2100
aaggagaact acgttaccct ccccggcacc ttcgacgagt gttaccccac ctacctctac  2160
cagaagatcg acgagtccaa gctgaaggcc tacacccgct accagctccg cggctacatc  2220
gaggactccc aggacctgga aatctacctc atccgctaca acgccaagca cgagatcgtg  2280
aacgtgcctg gcaccggcag cctctggcct ctcagcgtgg agaaccagat cggcccttgc  2340
ggcgagccta accgctgcgc ccctcacctc gagtggaacc ctgacctcca ctgctcgtgc  2400
agggacggcg agaagtgcgc ccaccatagc caccacttct ctctggacat cgacgtgggc  2460
tgcaccgacc tgaacgagga cctgggcgtg tgggttatct tcaagatcaa gacccaggac  2520
ggtcacgcca ggctgggtaa cctggagttc cttgaggaaa agcctctgct gggtgaggcc  2580
ctggccaggg tcaagagggc tgagaagaaa tggagggata agagggagac cctgcagctg  2640
gagaccacta tcgtctacaa ggaggctaag gagtctgtcg atgctctgtt cgtcaactct  2700
cagtacgata gactgcaagc tgataccaac atcgctatga tccacgctgc ggataagcgg  2760
gtccaccgga tccgggaggc ttaccttccg gagctttctg tcatcccggg tgtcaacgct  2820
gcgatcttcg aggaacttga ggaacggatc ttcactgcgt ttagtcttta cgatgcgcgg  2880
aacatcatca agaacgggga cttcaacaat ggtctgctgt gctggaacgt caagggtcat  2940
gtcgaggtcg aggaacaaaa caatcatcgt agtgtccttg tcattcctga gtgggaggcg  3000
gaggtctctc aagaggtccg tgtttgcccg gggcgtgggt acattcttcg tgttactgcg  3060
tacaaggagg ggtacgggga ggggtgcgtt actattcatg agattgagaa caatactgat  3120
gagcttaagt tcaacaattg tgttgaggag gaggtttacc cgaacaatac tgttacgtgc  3180
atcaactaca cggcaacgca agaggaatac gagggggacgt acacctcgcg taatagaggg  3240
tatgatgagg cgtacggaaa caacccgtcg gttccagcag attatgcctc ggtttatgag  3300
```

```
gagaagtcgt acacggatag acgacgcgag aatccatgtg agtcaaatcg aggatacgga  3360
gattacacac cattaccagc aggatacgtt acaaaggagt tggaatactt cccggaaaca  3420
gataaagttt ggattgaaat cggagaaaca gaaggaacat tcatcgtcga ctcagtagaa  3480
ttgttgttga tggaagaatg a                                            3501
```

| SEQ ID NO: 32 | moltype = AA  length = 1166 |
|---|---|
| FEATURE | Location/Qualifiers |
| REGION | 1..1166 |
| | note = Amino acid sequence of the engineered insecticidal proteinCry1Da1_3 encoded by a synthetic DNA sequence wherein anadditional Alanine residue has been inserted at position 2. |
| source | 1..1166 |
| | mol_type = protein |
| | organism = synthetic construct |

```
SEQUENCE: 32
MAEINNQNQC VPYNCLSNPK EIILGEERLE TGNTVADISL GLINFLYSNF VPGGGFIVGL   60
LELIWGFIGP SQWDIFLAQI EQLISQRIEE FARNQAISRL EGLSNLYKVY VRAFSDWEKD  120
PTNPALREEM RIQFNDMNSA LITAIPLFRV QNYEVALLSV YVQAANLHLS ILRDVSVFGE  180
RWGYDTATIN NRYSDLTSLI HVYTNHCVDT YNQGLRRLEG RFLSDWIVYN RFRRQLTISV  240
LDIVAFFPNY DIRTYPIQTA TQLTREVYLD LPFINENLSP AASYPTFSAA ESAIIRSPHL  300
VDFLNSFTIY TDSLARSAYW GGHLVNSFRT GTTTNLIRSP LYGREGNTER PVTITASPSV  360
PIFRTLSYIT GLDNSNPVAG IEGVEFQNTI SRSIYRKSGP IDSFSELPPQ DASVSPAIGY  420
SHRLCHATFL ERISGPRIAG TVFSWTHRSA SPTNEVSPSR ITQIPWVKAH TLASGASVIK  480
GPGFTGGDIL TRNSMGELGT LRVTFTGRLP QSYYIRFRYA SVANRSGTFR YSQPPSYGIS  540
FPKTMDAGEP LTSRSFAHTT LFTPITFSRA QEEFDLYIQS GVYIDRIEFI PVTATFEAEY  600
DLERAQKVVN ALFTSTNQLG LKTDVTDYHI DQVSNLVACL SDEFCLDEKR ELSEKVKHAK  660
RLSDERNLLQ DPNFRGINRQ PDRGWRGSTD ITIQGGDDVF KENYVTLPGT FDECYPTYLY  720
QKIDESKLKA YTRYQLRGYI EDSQDLEIYL IRYNAKHEIV NVPGTGSLWP LSVENQIGPC  780
GEPNRCAPHL EWNPDLHCSC RDGEKCAHHS HHFSLDIDVG CTDLNEDLGV WVIFKIKTQD  840
GHARLGNLEF LEEKPLLGEA LARVKRAEKK WRDKRETLQL ETTIVYKEAK ESVDALFVNS  900
QYDRLQADTN IAMIHAADKR VHRIREAYLP ELSVIPGVNA AIFEELEERI FTAFSLYDAR  960
NIIKNGDFNN GLLCWNVKGH VEVEEQNNHR SVLVIPEWEA EVSQEVRVCP GRGYILRVTA 1020
YKEGYGEGCV TIHEIENNTD ELKFNNCVEE EVYPNNTVTC INYTATQEEY EGTYTSRNRG 1080
YDEAYGNNPS VPADYASVYE EKSYTDRRRE NPCESNRGYG DYTPLPAGYV TKELEYFPET 1140
DKVWIEIGET EGTFIVDSVE LLLMEE                                     1166
```

| SEQ ID NO: 33 | moltype = DNA  length = 3501 |
|---|---|
| FEATURE | Location/Qualifiers |
| misc_feature | 1..3501 |
| | note = Synthetic DNA sequence designed for plant expression encodingCry1Da1_4 with an additional Alanine residue inserted at position2. |
| source | 1..3501 |
| | mol_type = other DNA |
| | organism = synthetic construct |

```
SEQUENCE: 33
atggctgaga tcaacaacca gaaccagtgc gtcccgtaca actgcctgag caaccctaag   60
gagatcatcc tgggtgagga acgcctggag accggcaaca ccgtagccga cattagcctg  120
ggcctcatca acttcctcta cagcaacttc gtgccgggcg gtggcttcat cgtgggcctc  180
ctggagctta tctgggggcttt catcggcccg tccagtggga acatcttcct cgcccagatc  240
gagcaactga tcagccagcg gatcgaggag ttcgctagga accaggccat ctcccgcctg  300
gagggactct ccaacctcta caaggtgtac gtgcgcgcgt tcagcgactg ggagaaggac  360
ccgaccaacc cggccctccg cgaggaaatg cgtatccagt tcaacgatat gaactcggcc  420
ctcatcaccg ccatcccgct cttccgcgtg cagaactacg aggtggccct cctgtccgtg  480
tacgttcaag ccgccaacct ccacctctcc atcctccgcg acgtgagcgt gttcggcgag  540
cgctggggct acgacaccgc caccatcaac aaccgctact ccgacctcac ctccctcatc  600
cacgtttaca ccaaccactg cgtggacacg tacaaccagg gcctccgccg cctggagggc  660
cgcttcctct ccgactggat cgtgtacaac cgcttccgcc gccagctcac catctccgtc  720
ctggacatcg tcgccttctt tcccaactac gacatccgca cctaccctat ccagaccgcc  780
acccagctca cccgcgaggt ctacctcgac ctcccgttca tcaacgagaa cctcagcccg  840
gccgccagct cccgaccttt ctccgccgct gagtccgcca tcattcgcag cccgcacctc  900
gtggacttcc tcaactcctt caccatctac accgactccc tcgcccgcta cgcctactgg  960
ggcggtcacc tcgtgaactc cttccgcacc ggcaccacta ccaacctcat ccgcagcccg 1020
ctctacggcc gcgagggcaa caccgagcgc ccggtgacca tcaccgccag cccgagcgtg 1080
cccatcttcc gcaccctcag ctacatcacc ggcctggaca caggaaaccc tgtggcgggc 1140
atcgagggcg tggagttcca gaacaccatc tccaggagca tctaccgcaa gagcggcccc 1200
atcgacagct tcagcgagct gcctcctccg gacgccagcg tgagccctgc catcggctac 1260
agccacaggc tgtgccacgc caccttcctg gagcgcatca gcggccctcg catcgcgggc 1320
accgtgttct cgtggaccca ccgcagcgcc tctcctacga cgaggtgtcc cctagtcgc  1380
atcacccaga tcccttgggt caaggcccac accctggcta gtggcgctag tgtcatcaag 1440
ggccctggct tcaccggtgg tgacatcctg accaggaact ctatgggcga gctgggcact 1500
ctgagggtca ctttcactgg ccgcctgcct cagtcttact acatccgctt ccgctacgct 1560
agtgtcgcta accgctctgg tactttccgc tactctcagc ctccgtcttc cggtatctct 1620
ttccctaaga ctatggacgc tggtgagcct ctgaccagta ggagcttcgc tcacactact 1680
ctgttcactc ctatcacttt ctctagggct caggaggagt tcgacctgta catccagtct 1740
ggtgtgtaca tcgacaggat cgagttcatc ccggtgaccg ccacgttcga ggccgagtac 1800
gaccttgagc gcgcccagaa ggtggtgaac gcccctctca ctagcactaa ccagctaggc 1860
ctgaagactg acgtgaccga ctaccacatc gaccaagtga gcaacctagt ggcctgcctc 1920
```

-continued

```
tccgacgagt tctgcctcga cgagaagcgc gagctgtccg agaaggtgaa gcacgccaag 1980
cgcctctccg acgagcgcaa cctgctccag gaccccaact tcaggggcat caacaggcag 2040
cccgaccgcg gctggcgcgg ctccaccgac atcaccatcc agggcggtga cgacgtattc 2100
aaggagaact acgttaccct ccccggcacc ttcgacgagt gttacccac ctacctctac 2160
cagaagatcg acgagtccaa gctgaaggcc tacacccgct accagctccg cggctacatc 2220
gaggactccc aggacctgga aatctacctc atccgctaca acgccaagca cgagatcgtg 2280
aacgtgcctg gcaccggcag cctctggcct ctcagcgtgg agaaccagat cggcccttgc 2340
ggcgagccta accgctgcgc ccctcacctc gagtggaacc ctgacctcca ctgctcgtgc 2400
agggacggcg agaagtgcgc ccaccatagc caccacttct ctctggacat cgacgtgggc 2460
tgcaccgacc tgaacgagga cctgggcgtg tgggttatct tcaagatcaa gacccaggac 2520
ggtcacgcca ggctgggtaa cctggagttc cttgaggaaa agcctctgct gggtgaggcc 2580
ctggccaggt caagagggc tgagaagaaa tggagggata gagggagac cctgcagctg 2640
gagaccacta tcgtctacaa ggaggctaag gagtctgtcg atgctctgtt cgtcaactct 2700
cagtacgata gactgcaagc tgataccaac atcgctatga tccacgctgc ggataagcag 2760
gtccaccgga tccgggaggc ttaccttccg gagctttctg tcatccccgg tgtcaacgct 2820
gcgatcttcg aggaacttga ggaacgcatc ttcactgcgt ttagtctta cgatgcgcgg 2880
aacatcatca agaacgggga cttcaacaat ggtctgctgt gctggaacgt caagggtcat 2940
gtcgaggtcg aggaacaaaa caatcatcgt agtgtccttg tcattcctga gtgggaggcg 3000
gaggtctctc aagaggtccg tgtttgcccg gggcgtgggt acattcttcg tgttactgcg 3060
tacaaggagg gtacgggga ggggtgcgtt actattcatg agattgagaa caatactgat 3120
gagcttaagt tcaacaattg tgttgaggag gaggtttacc cgaacaatac tgttacgtgc 3180
atcaactaca cggcaacgca agaggaatac gaggggacgt acacctcgcg taatagagg 3240
tatgatgagg cgtacggaaa caacccgtcg gttccagcag attatgcctc ggtttatgag 3300
gagaagtcgt acacggatag acgacgcgag aatccatgtg agtcaaatcg aggatacgga 3360
gattacacac cattaccagc aggatacgtt acaaaggagt ggaatactt cccggaaaca 3420
gataaagttt ggattgaaat cggagaaaca gaaggaacat tcatcgtcga ctcagtagaa 3480
ttgttgttga tggaagaatg a                                       3501
```

SEQ ID NO: 34   moltype = AA length = 1166
FEATURE    Location/Qualifiers
REGION     1..1166
        note = Amino acid sequence of the engineered insecticidal
        proteinCry1Da1_4 encoded by a synthetic DNA sequence
        wherein anadditional Alanine residue has been inserted at
        position 2.
source     1..1166
        mol_type = protein
        organism = synthetic construct
SEQUENCE: 34

```
MAEINNQNQC VPYNCLSNPK EIILGEERLE TGNTVADISL GLINFLYSNF VPGGGFIVGL  60
LELIWGFIGP SQWDIFLAQI EQLISQRIEE FARNQAISRL EGLSNLYKVY VRAFSDWEKD 120
PTNPALREEM RIQFNDMNSA LITAIPLFRV QNYEVALLSV YVQAANLHLS ILRDVSVFGE 180
RWGYDTATIN NRYSDLTSLI HVYTNHCVDT YNQGLRRLEG RFLSDWIVYN RFRRQLTISV 240
LDIVAFFPNY DIRTYPIQTA TQLTREVYLD LPFINENLSP AASYPTFSAA ESAIIRSPHL 300
VDFLNSFTIY TDSLARYAYW GGHLVNSFRT GTTTNLIRSP LYGREGNTER PVTITASPSV 360
PIFRTLSYIT GLDNRNPVAG IEGVEFQNTI SRSIYRKSGP IDSFSELPPQ DASVSPAIGY 420
SHRLCHATFL ERISGPRIAG TVFSWTHRSA SPTNEVSPSR ITQIPWVKAH TLASGASVIK 480
GPGFTGGDIL TRNSMGELGT LRVTFTGRLP QSYYIRFRYA SVANRSGTFR YSQPPSYGIS 540
FPKTMDAGEP LTSRSFAHTT LFTPITFSRA QEEFDLYIQS GVYIDRIEFI PVTATFEAEY 600
DLERAQKVVN ALFTSTNQLG LKTDVTDYHI DQVSNLVACL SDEFCLDEKR ELSEKVKHAK 660
RLSDERNLLQ DPNFRGINRQ PDRGWRGSTD ITIQGGDVF KENYVTLPGT FDECYPTYLY 720
QKIDESKLKA YTRYQLRGYI EDSQDLEIYL IRYNAKHEIV NVPGTGSLWP LSVENQIGPC 780
GEPNRCAPHL EWNPDLHCSC RDGEKCAHHS HHFSLDIDVG CTDLNEDLGV WVIFKIKTQD 840
GHARLGNLEF LEEKPLLGEA LARVKRAEKK WRDKRETLQL ETTIVYKEAK ESVDALFVNS 900
QYDRLQADTN IAMIHAADKR VHRIREAYLP ELSVIPGVNA AIFEELEERI FTAFSLYDAR 960
NIIKNGDFNN GLLCWNVKGH VEVEEQNNHR SVLVIPEWEA EVSQEVRVCP GRGYILRVTA 1020
YKEGYGEGCV TIHEIENNTD ELKFNNCVEE EVYPNNTVTC INYTATQEEY EGTYTSRNRG 1080
YDEAYGNNPS VPADYASVYE EKSYTDRRRE NPCESNRGYG DYTPLPAGYV TKELEYFPET 1140
DKVWIEIGET EGTFIVDSVE LLLMEE                                   1166
```

SEQ ID NO: 35   moltype = DNA length = 3501
FEATURE    Location/Qualifiers
misc_feature  1..3501
        note = Synthetic DNA sequence designed for plant expression
        encodingCry1Da1_5 with an additional Alanine residue
        inserted at position2.
source     1..3501
        mol_type = other DNA
        organism = synthetic construct
SEQUENCE: 35

```
atggctgaga tcaacaacca gaaccagtgc gtcccgtaca actgcctgag caaccctaag  60
gagatcatcc tgggtgagga acgcctggag accggcaaca ccgtagccga cattagcctg 120
ggcctcatca acttcctcta cagcaacttc gtcccggcgt gtggcttcat cgtgggcctc 180
ctggagctta tctgggggctt catcggcccg tcccagtgga acatcttcct cgcccagatc 240
gagcaactga tcagccagcg gatcgaggag ttcgctagga accaggccat ctcccgcctg 300
gagggactct ccaacctcta caaggtgtac gtgcgcgcgt tcagcgactg ggagaaggac 360
ccgaccaacc cggccctccg cgaggaaatg cgtatccagt tcaacgatat gaactcggcc 420
ctcatcaccg ccatcccgct cttccgcgtg cagaactacg aggtggccct cctgtccgtg 480
tacgttcaag ccgccaacct ccacctctcc atcctccgcg acgtgagcgt gttcggcgag 540
```

```
cgctgggct  acgacaccgc  caccatcaac  aaccgctact  ccgacctcac  ctccctcatc   600
cacgtttaca  ccaaccactg  cgtggacacg  tacaaccagg  gcctccgccg  cctggagggc   660
cgcttcctct  ccgactggat  cgtgtacaac  cgcttccgcc  gccagctcac  catctccgtc   720
ctggacatcg  tcgccttctt  tcccaactac  gacatccgca  cctacccat   ccagaccgcc   780
acccagctca  cccgcgaggt  ctacctcgac  ctcccgttca  tcaacgagaa  cctcagcccg   840
gccgccagct  acccgacctt  ctccgccgct  gagtccgcca  tcattcgcag  cccgcacctc   900
gtggacttcc  tcaactcctt  caccatctac  accgactccc  tcgccgcag   cgcctactgg   960
ggcggtcacc  tcgtgaactc  cttccgcacc  ggcaccacta  ccaacctcat  ccgcagcccg  1020
ctctacggcc  gcgagggcaa  caccgagcgc  ccggtgacca  tcaccgccag  cccgagcgtg  1080
cccatcttcc  gcaccctcag  ctaccgcacc  ggcctggaca  acagcaaccc  tgtggcgggc  1140
atcgagggcg  tggagttcca  gaacaccatc  tccaggagca  tctaccgcaa  gagcggccct  1200
atcgacagct  cagcgagct   gcctcctcag  gacgccagcg  tgagcctgc   catcggctac  1260
agccacaggc  tgtgccacgc  cacctcctg  gagcgcatca  gcggccctcg  catcgcgggc  1320
accgtgttct  cgtggaccca  ccgcagcgcc  tctcctacga  acgaggtgtc  tcctagtcgc  1380
atcacccaga  tccctggggt  caaggcccac  accctggcta  gtgcgctag   tgtcatcaag  1440
ggccctggct  tcaccggtgg  tgacatcctg  accaggaact  ctatgggcga  gctgggcact  1500
ctgagggtca  ctttcactgg  ccgcctgcct  cagtcttact  acatccgctt  ccgctacgct  1560
agtgtcgcta  accgctctgg  tactttccgc  tactctcagc  ctccgtctta  cggtatctct  1620
ttccctaaga  ctatgacgc   tggtgagcct  ctgaccagta  ggagcttcgc  tcacactact  1680
ctgttcactc  ctatcacttt  ctctagggct  caggaggagt  tcgacctgta  catccagtct  1740
ggtgtgtaca  tcgacaggat  cgagttcatc  cccgtgaccg  ccacgttcga  ggccgagtac  1800
gaccttgagc  gcgcccagaa  ggtggtgaac  gccctcttca  ctagcactaa  ccagctaggc  1860
ctgaagactg  acgtgaccga  ctaccacatc  gaccaagtga  gcaacctagt  ggcctgcctc  1920
tccgacgagt  tctgcctcga  cgagaagcgc  gagctgtccg  agaaggtgaa  gcacgccaag  1980
cgcctctccg  acgagcgcaa  cctgctccag  gaccccaact  tcaggggcat  caacaggcag  2040
cccgacgcg   gctggcgcgg  ttccaccgac  atcaccatcc  agggcggtga  cgacgtattc  2100
aaggagaact  acgttaccct  ccccggcacc  ttcgacgagt  gttacccac   ctacctctac  2160
cagaagatcg  acgagtccaa  gctgaaggcc  tacacccgct  accagctccg  cggctacatc  2220
gaggactccc  aggacctgga  aatctacctc  atccgctaca  acgccaagca  cgagatcgtg  2280
aacgtgcctg  gcaccggcag  cctctggcct  ctcagcgtgg  agaaccagat  cggccctgc   2340
ggcgagccta  accgctgcgc  ccctcacctc  gagtggaacc  ctgacctcca  ctgctcgtga  2400
agggacggcg  agaagtgcgc  caccatagc   caccacttct  ctctggacat  cgacgtgggc  2460
tgcaccgacc  tgaacgagga  cctgggcgtg  tgggttatct  tcaagatcaa  gacccaggac  2520
ggtcacgcca  ggctgggtaa  cctggagttc  cttgaggaaa  agcctctgct  gggtgaggcc  2580
ctggccaggg  tcaagagggc  tgagaagaaa  tggagggata  agagggagac  cctgcagctg  2640
gagaccacta  tcgtctacaa  ggaggctaag  gagtctgtcg  atgctctgtt  cgtcaactct  2700
cagtacgata  gactgcaagc  tgataccaac  atcgctatga  tccacgctgc  ggataagcgg  2760
gtccaccgga  tccgggaggc  ttaccttccg  gagctttctg  tcatcccggg  tgtcaacgct  2820
gcgatcttcg  aggaacttga  ggaacggatc  ttcactgcgt  tagtctttta  cgatgcgcgg  2880
aacatcatca  agaacgggga  cttcaacaat  ggtctgctgt  gctgaacgt   caagggtcat  2940
gtcgaggtcg  aggaacaaaa  caatcatcgt  agtgtccttg  tcattcctga  gtgggaggcc  3000
gaggtctctc  aagaggtccg  tgtttgcccg  ggcgtgggt   acattcttcg  tgttactgcg  3060
tacaaggagg  ggtacgttg   actattcatg  agattgagaa  caatactgat  3120
gagcttaagt  tcaacaattg  tgttgaggag  gaggtttacc  cgaacaatac  tgttacgtgc  3180
atcaactaca  cggcaacgca  agaggaatac  gaggggacgt  acacctcgcg  taatagaggg  3240
tatgatgagg  cgtacggaaa  caacccgtcg  gttccagcag  attatgcctc  ggtttatgag  3300
gagaagtcgt  acacggatag  acgacgcgag  aatccatgtg  agtcaaatcg  aggatacgga  3360
gattacacac  cattaccagc  aggatacgtt  acaaaggagt  tggaatactt  cccggaaaca  3420
gataaagttt  ggattgaaat  cggagaaaca  gaaggaacat  tcatcgtcga  ctcagtagaa  3480
ttgttgttga  tggaagaatg  a                                              3501
```

SEQ ID NO: 36    moltype = AA length = 1166
FEATURE      Location/Qualifiers
REGION       1..1166
          note = Amino acid sequence of the engineered insecticidal
          proteinCry1Da1_5 encoded by a synthetic DNA sequence
          wherein anadditional Alanine residue has been inserted at
          position 2.
source       1..1166
          mol_type = protein
          organism = synthetic construct

SEQUENCE: 36

```
MAEINNQNQC  VPYNCLSNPK  EIILGEERLE  TGNTVADISL  GLINFLYSNF  VPGGGFIVGL    60
LELIWGFIGP  SQWDIFLAQI  EQLISQRIEE  FARNQAISRL  EGLSNLYKVY  VRAFSDWEKD   120
PTNPALREEM  RIQFNDMNSA  LITAIPLFRV  QNYEVALLSV  YVQAANLHLS  ILRDVSVFGE   180
RWGYDTATIN  NRYSDLTSLI  HVYTNHCVDT  YNQGLRRLEG  RFLSDWIVYN  RFRRQLTISV   240
LDIVAFFPNY  DIRTYPIQTA  TQLTREVYLD  LPFINENLSP  AASYPTFSAA  ESAIIRSPHL   300
VDFLNSFTIY  TDSLARSAYW  GGHLVNSFRT  GTTTNLIRSP  LYGREGNTER  PVTITASPSV   360
PIFRTLSYRT  GLDNSNPVAG  IEGVEFQNTI  SRSIYRKSGP  IDSFSELPPQ  DASVSPAIGY   420
SHRLCHATFL  ERISGPRIAG  TVFSWTHRSA  SPTNEVSPSR  ITQIPVVKAH  TLASGASVIK   480
GPGFTGGDIL  TRNSMGELGT  LRVTFTGRLP  QSYYIRFRYA  SVANRSGTFR  YSQPPSYGIS   540
FPKTMDAGEP  LTSRSFAHTT  LFTPITFSRA  QEEFDLYIQS  GVYIDRIEFI  PVTATFEAEY   600
DLERAQKVVN  ALFTSTNQLG  LKTDVTDYHI  DQVSNLVACL  SDEFCLDEKR  ELSEKVKHAK   660
RLSDERNLLQ  DPNFRGINRQ  PDRGWRGSTD  ITIQGGDDVF  KENYVTLPGT  FDECYPTYLY   720
QKIDESKLKA  YTRYQLRGYI  EDSQDLEIYL  IRYNAKHEIV  NVPGTGSLWP  LSVENQIGPC   780
GEPNRCAPHL  EWNPDLHCSC  RDGEKCAHHS  HHFSLDIDVG  CTDLNEDLGV  WVIFKIKTQD   840
GHARLGNLEF  LEEKPLLGEA  LARVKRAEKK  WRDKRETLQL  ETTIVYKEAK  ESVDALFVNS   900
QYDRLQADTN  IAMIHAADKR  VHRIREAYLP  ELSVIPGVNA  AIFEELEERI  FTAFSLYDAR   960
NIIKNGDFNN  GLLCWNVKGH  VEVEEQNNHR  SVLVIPEWEA  EVSQEVRVCP  GRGYILRVTA  1020
```

-continued

```
YKEGYGEGCV TIHEIENNTD ELKFNNCVEE EVYPNNTVTC INYTATQEEY EGTYTSRNRG  1080
YDEAYGNNPS VPADYASVYE EKSYTDRRRE NPCESNRGYG DYTPLPAGYV TKELEYFPET  1140
DKVWIEIGET EGTFIVDSVE LLLMEE                                       1166

SEQ ID NO: 37          moltype = DNA  length = 3501
FEATURE                Location/Qualifiers
misc_feature           1..3501
                       note = Synthetic DNA sequence designed for plant expression
                        encodingCry1Da1_6 with an additional Alanine residue
                        inserted at position2.
source                 1..3501
                       mol_type = other DNA
                       organism = synthetic construct
SEQUENCE: 37
atggctgaga tcaacaacca gaaccagtgc gtcccgtaca actgcctgag caaccctaag  60
gagatcatcc tgggtgagga acgcctggag accggcaaca ccgtagccga cattagcctg  120
ggcctcatca acttcctcta cagcaacttc gtgcccggcg gtggcttcat cgtgggcctc  180
ctggagctta tctggggctt catcggcccg tcccagtggg acatcttcct cgcccagatc  240
gagcaactga tcagccagcg gatcgaggag ttcgctagga accaggccat ctcccgcctg  300
gagggactct ccaacctcta caaggtgtac gtgcgcgcgt tcagcgactg ggagaaggac  360
ccgaccaacc cggccctccg cgaggaaatg cgtatccagt tcaacgatat gaactcggcc  420
ctcatcaccg ccatcccgct cttccgcgtg cagaactacg aggtggccct cctgtccgtg  480
tacgttcaag ccgccaacct ccacctctcc atcctccgcg acgtgagcgt gttcggcgag  540
cgctggggct acgacaccgc caccatcaac aaccgctact ccgacctcac ctccctcatc  600
cacgtttaca ccaaccactg cgtggacacg tacaaccagg gcctccgccg cctggagggc  660
cgcttcctct ccgactggat cgtgtacaac cgcttccgcc gccagctcac catctccgtc  720
ctggacatcg tcgccttctt tcccaactac gacatccgca cctaccctat ccagaccgcc  780
acccagctca cccgcgaggt ctacctcgac ctcccgttca tcaacgagaa cctcagcccg  840
gccgccaagt acccgacctt ctccgccgct gagtccgcca tcattcgcag cccgcacctc  900
gtggacttcc tcaactcctt caccatctac accgactccc tcgcccgcag cgcctactgg  960
ggcggtcacc tcgtgaactc cttccgcacc ggcaccacta ccaacctcat ccgcagcccg  1020
ctctacggcc gcgagggcaa caccgagcgc ccggtgacca tcaccgccag cccgagcgtg  1080
cccatcttcc gcaccctcag ctaccccacc ggcctggaca acagcaaccc tgtggcgggc  1140
atcgagggcg tggagttcca gaacaccatc tccaggagca tctaccgcaa gagcggccct  1200
atcgacagct tcagcgagct gcctcctcag gacgccagcg tgagccctgc catcggctac  1260
agccacaggc tgtgccacgc caccttcctg gagcgcatca gcggccctcg catcgcgggc  1320
accgtgttct cgtggaccca ccgcagcgcc tctcctacga acgaggtgtc tcctagtcgc  1380
atcacccaga tcccttgggt caaggcccac accctggcta gtggcgctag tgtcatcaag  1440
ggccctggct tcaccggtgg tgacatcctg accaggaact ctatgggcga gctgggcact  1500
ctgagggtca ctttcactgg ccgcctgcct cagtcttact acatccgctt ccgctacgct  1560
agtgtcgcta accgctctgg tactttccgc tactctcagc ctccgtctta cggtatctct  1620
ttccctaaga ctatggacgc tggtgagcct ctgaccagta ggagcttcgc tcacactact  1680
ctgttcactc ctatcacttt ctctagggct caggaggagt tcgacctgta catccagtct  1740
ggtgtgtaca tcgacaggat cgagttcatc cccgtgaccg ccacgttcga ggccgagtac  1800
gaccttgagc gcgcccagaa ggtggtgaac gccctcttca ctagcactaa ccagctaggc  1860
ctgaagactg acgtgaccga ctaccacatc gaccaagtga gcaacctagt ggcctgcctc  1920
tccgacgagt tctgcctcga cgagaagcgc gagctgtccg agaaggtgaa gcacgccaag  1980
cgcctctccg acgagcgcaa cctgctccag gaccccaact tcaggggcat caacaggcag  2040
cccgaccgcg gctggcgcgg ctccaccgac atcaccatcc agggcggtga cgacgtattc  2100
aaggagaact acgttaccct ccccggcacc ttcgacgagt gttaccccac ctacctctac  2160
cagaagatcg acgagtccaa gctgaaggcc tacacccgct accagctccg cggctacatc  2220
gaggactccc aggacctgga aatctacctc atccgctaca acgccaagca cgagatcgtg  2280
aacgtgcctg gcaccggcag cctctggcct ctcagcgtgg agaaccagat cggccccttgc  2340
ggcgagccta accgctgcgc ccctcacctc gagtggaacc ctgacctcca ctgctcgtgc  2400
agggacggcg agaagtgcgc ccaccatagc caccacttct ctctggacat cgacgtgggc  2460
tgcaccgacc tgaacgagga cctgggcgtg tgggttatct tcaagatcaa gacccaggac  2520
ggtcacgcca ggctgggtaa cctggagttc cttgaggaaa agcctctgct gggtgaggcc  2580
ctggccaggg tcaagagggc tgagaagaaa tggagggata agagggagac cctgcagctg  2640
gagaccacta tcgtctacaa ggaggctaag gagtctgtcg atgctctgtt cgtcaactct  2700
cagtacgata gactgcaagc tgataccaac atcgctatga tccacgctgc ggataagcgg  2760
gtccaccgga tccgggaggc ttaccttccg gagctttctg tcatcccggg tgtcaacgct  2820
gcgatcttcg aggaacttga ggaacggatc ttcactgcgt ttagtcttta cgatgcgcgg  2880
aacatcatca agaacgggga cttcaacaat ggtctgctgt gctggaacgt caagggtcat  2940
gtcgaggtcg aggaacaaaa caatcatcgt agtgtccttg tcattcctga gtgggaggcg  3000
gaggtctctc aagaggtccg tgtttgcccg gggcgtgggt acattcttcg tgttactgcg  3060
tacaaggagg ggtacgggga ggggtgcgtt actattcatg agattgagaa caatactgat  3120
gagcttaagt tcaacaattg tgttgaggag gaggtttacc cgaacaatac tgttacgtgc  3180
atcaactaca cggcaacgca agaggaatac gaggggacgt acacctcgcg taatagaggg  3240
tatgatgagg cgtacggaaa caacccgtcg gttccagcag attatgcctc ggtttatgag  3300
gagaagtcgt acacggatag acgacgcgag aatccatgtg agtcaaatcg aggatacgga  3360
gattacacac cattaccagc aggatacgtt acaaaggagt tggaatactt cccggaaaca  3420
gataaagttt ggattgaaat cggagaaaca gaaggaacat tcatcgtcga ctcagtagaa  3480
ttgttgttga tggaagaatg a                                            3501

SEQ ID NO: 38          moltype = AA  length = 1166
FEATURE                Location/Qualifiers
REGION                 1..1166
                       note = Amino acid sequence of the engineered insecticidal
                        proteinCry1Da1_6 encoded by a synthetic DNA sequence
```

```
                            wherein anadditional Alanine residue has been inserted at
                            position 2.
source                      1..1166
                            mol_type = protein
                            organism = synthetic construct
SEQUENCE: 38
MAEINNQNQC VPYNCLSNPK EIILGEERLE TGNTVADISL GLINFLYSNF VPGGGFIVGL    60
LELIWGFIGP SQWDIFLAQI EQLISQRIEE FARNQAISRL EGLSNLYKVY VRAFSDWEKD   120
PTNPALREEM RIQFNDMNSA LITAIPLFRV QNYEVALLSV YVQAANLHLS ILRDVSVFGE   180
RWGYDTATIN NRYSDLTSLI HVYTNHCVDT YNQGLRRLEG RFLSDWIVYN RFRRQLTISV   240
LDIVAFFPNY DIRTYPIQTA TQLTREVYLD LPFINENLSP AAKYPTFSAA ESAIIRSPHL   300
VDFLNSFTIY TDSLARSAYW GGHLVNSFRT GTTTNLIRSP LYGREGNTER PVTITASPSV   360
PIFRTLSYPT GLDNSNPVAG IEGVEFQNTI SRSIYRKSGP IDSFSELPPQ DASVSPAIGY   420
SHRLCHATFL ERISGPRIAG TVFSWTHRSA SPTNEVSPSR ITQIPWVKAH TLASGASVIK   480
GPGFTGGDIL TRNSMGELGT LRVTFTGRLP QSYYIRFRYA SVANRSGTFR YSQPPSYGIS   540
FPKTMDAGEP LTSRSFAHTT LFTPITFSRA QEEFDLYIQS GVYIDRIEFI PVTATFEAEY   600
DLERAQKVVN ALFTSTNQLG LKTDVTDYHI DQVSNLVACL SDEFCLDEKR ELSEKVKHAK   660
RLSDERNLLQ DPNFRGINRQ PDRGWRGSTD ITIQGGDDVF KENYVTLPGT FDECYPTYLY   720
QKIDESKLKA YTRYQLRGYI EDSQDLEIYL IRYNAKHEIV NVPGTGSLWP LSVENQIGPC   780
GEPNRCAPHL EWNPDLHCSC RDGEKCAHHS HHFSLDIDVG CTDLNEDLGV WVIFKIKTQD   840
GHARLGNLEF LEEKPLLGEA LARVKRAEKK WRDKRETLQL ETTIVYKEAK ESVDALFVNS   900
QYDRLQADTN IAMIHAADKR VHRIREAYLP ELSVIPGVNA AIFEELEERI FTAFSLYDAR   960
NIIKNGDFNN GLLCWNVKGH VEVEEQNNHR SVLVIPEWEA EVSQEVRVCP GRGYILRVTA  1020
YKEGYGEGCV TIHEIENNTD ELKFNNCVEE EVYPNNTVTC INYTATQEEY EGTYTSRNRG  1080
YDEAYGNNPS VPADYASVYE EKSYTDRRRE NPCESNRGYG DYTPLPAGYV TKELEYFPET  1140
DKVWIEIGET EGTFIVDSVE LLLMEE                                      1166

SEQ ID NO: 39           moltype = DNA   length = 3501
FEATURE                 Location/Qualifiers
misc_feature            1..3501
                        note = Synthetic DNA sequence designed for plant expression
                         encodingCry1Da1_7 with an additional Alanine residue
                         inserted at position2.
source                  1..3501
                        mol_type = other DNA
                        organism = synthetic construct
SEQUENCE: 39
atggctgaga tcaacaacca gaaccagtgc gtcccgtaca actgcctgag caaccctaag    60
gagatcatcc tgggtgagga acgcctggag accggcaaca ccgtagccga cattagcctg   120
ggcctcatca acttcctcta cagcaacttc gtgcccggcg gtggcttcat cgtgggcctc   180
ctggagctta tctggggctt catcggcccg tccagtggga acatcttcct cgcccagatc   240
gagcaactga tcagccagcg gatcgaggag ttcgctagga accaggccat ctcccgcctg   300
gagggactct ccaacctcta caaggtgtac gtgcgcgcgt tcagcgactg ggagaaggac   360
ccgaccaacc cggccctccg cgaggaaatg cgtatccagt tcaacgatat gaactcggcc   420
ctcatcaccg ccatcccgct cttccgcgtg cagaactacg aggtggccct cctgtccgtg   480
tacgttcaag ccgccaacct ccacctctcc atcctccgcg acgtgagcgt gttcggcgag   540
cgctggggct acgacaccgc caccatcaac aaccgctact ccgacctcac ctccctcatc   600
cacgtttaca ccaaccactg cgtggacacg tacaaccagg gcctccgccg cctggagggc   660
cgcttcctct ccgactggat cgtgtacaac cgcttccgcc gccagctcac catctccgtc   720
ctggacatcg tcgccttctt tcccaactac gacatccgca cctaccctat ccagaccgcc   780
acccagctca cccgcgaggt ctacctcgac ctccgttca tcaacgagaa cctcagccgg   840
gccgccgtct acccgacctt ctccgccgct gagtccgcca tcattcgcag cccgcacctc   900
gtggacttcc tcaactcctt caccatctac accgactccc tcgcccgcag cgcctactgg   960
ggcggtcacc tcgtgaactc cttccgcacc ggcaccacta ccaacctcat ccgcagcccg  1020
ctctacggcc gcgagggcaa caccgagcgc ccggtgacca tcaccgcgag cccgagcgtg  1080
cccatcttcc gcaccctcag ctaccccacc ggcctggaca acagcaaccc tgtggcgggc  1140
atcgagggcg tggagttcca gaacaccatc tccaggagca tctaccgcaa gagcggccct  1200
atcgacagct cagcgagct gcctcctcag gacgccagcg tgagccctgc catcggctac  1260
agccacaggc tgtgccacgc caccttcctg gagcgcatca gcggcccccg catgcgcggc  1320
accgtgttct cgtggaccca ccgcagcgcc tctcctacga acgaggtgtc tcctagtccg  1380
atcacccaga tccccttgggt caaggcccac accctggcta gtgcgctag tgtcatcaag  1440
ggccctggct tcaccggtgg tgacatcctg accaggaact ctatgggcga gctgggcact  1500
ctgagggtca ctttcactgg ccgctgcct cagtcttact acatccgctt ccgctacgct  1560
agtgtcgcta accgctctgg tactttccgc tactctcagc ctccgtctta cggtatctc   1620
ttccctaaga ctatgacgc tggtgagcct ctgaccagta ggagcttcgc tcacactact  1680
ctgttcactc ctatcacttt ctctagggct caggaggagt tcgacctgta catccagtct  1740
ggtgtgtaca tcgacaggat cgagttcatc ccgtgaccg ccacgttcga ggccgagtac  1800
gaccttgagc gcgcccagaa ggtggtgaac gccctcttca ctagcactaa ccagctaggc  1860
ctgaagactg acgtgaccga ctaccacatc gaccaagtga ctccgtctta ggcctgcctc  1920
tccgacgagt tctgcctcga cgagaagcgc gagctgtccg agaaggtgaa gcacgccaag  1980
cgcctctccg acgagcgcaa cctgctccag gaccccaact caggggcat caacaggcag  2040
cccgaccgcg gctggcgcgg ctccaccgac atcaccatcc agggcggtga cgacgtattc  2100
aaggagaact acgttaccct cccgggcacc ttcgacgagt gttaccccac ctacctctac  2160
cagaagatcg acgagtccaa gctgaaggcc tacacccgct acacgcagct ccgcggctac  2220
gaggactccc aggacctgga aatctacctc atccgctaca acgccaagca cgagatcgtg  2280
aacgtgcctg gcaccggcag cctctggcct ctcagcgtgg agaaccagat cggcccttgc  2340
ggcgagccta accgctgcgc ccctcacctc gagtggaacc ctgacctcca ctgctcgtgc  2400
agggacggcg agaagtgcgc ccaccatagc caccacttct ctctggacat cgacgtgggc  2460
tgcaccgacc tgaacgagga cctgggcgtg tgggttatct tcaagatcaa gacccaggac  2520
```

-continued

```
ggtcacgcca ggctgggtaa cctggagttc cttgaggaaa agcctctgct gggtgaggcc   2580
ctggccaggg tcaagagggc tgagaagaaa tggagggata agaggagac cctgcagctg    2640
gagaccacta tcgtctacaa ggaggctaag gagtctgtcg atgctctgtt cgtcaactct   2700
cagtacgata gactgcaagc tgataccaac atcgctatga tccacgctgc ggataagcgg   2760
gtccaccgga tccgggaggc ttaccttccg gagctttctg tcatcccggg tgtcaacgct   2820
gcgatcttcg aggaacttga ggaacggatc ttcactgcgt ttagtcttta cgatgcgcgg   2880
aacatcatca gaacgggga cttcaacaat ggtctgctgt gctggaacgt caagggtcat    2940
gtcgaggtcg aggaacaaaa caatcatcgt agtgtccttg tcattcctga gtggggaggcc  3000
gaggtctctc aagaggtccg tgtttgcccg gggcgtgggt acattcttcg tgttactgcg   3060
tacaaggagg ggtacgggga ggggtgcgtt actattcatg agattgagaa caatactgat   3120
gagcttaagt tcaacaattg tgttgaggag gaggtttacc cgaacaatac tgttacgtgc   3180
atcaactaca cggcaacgca agaggaatac gaggggacgt cacctcgcg taatagaggg    3240
tatgatgagg cgtacggaaa caacccgtcg gttccagcag attatgcctc ggtttatgag   3300
gagaagtcgt acacggatag acgacgcgag aatccatgtc agtcaaatcg aggatacgga   3360
gattacacac cattaccagc aggatacgtt acaaaggagt tggaatactt cccgaaaaca   3420
gataaagttt ggattgaaat cggagaaaca gaaggaacat tcatcgtcga ctcagtagaa   3480
ttgttgttga tggaagaatg a                                             3501
```

```
SEQ ID NO: 40          moltype = AA  length = 1166
FEATURE                Location/Qualifiers
REGION                 1..1166
                       note = Amino acid sequence of the engineered insecticidal
                       proteinCry1Da1_7 encoded by a synthetic DNA sequence
                       wherein anadditional Alanine residue has been inserted at
                       position 2.
source                 1..1166
                       mol_type = protein
                       organism = synthetic construct
SEQUENCE: 40
MAEINNQNQC VPYNCLSNPK EIILGEERLE TGNTVADISL GLINFLYSNF VPGGGFIVGL    60
LELIWGFIGP SQWDIFLAQI EQLISQRIEE FARNQAISRL EGLSNLYKVY VRAFSDWEKD   120
PTNPALREEM RIQFNDMNSA LITAIPLFRV QNYEVALLSV YVQAANLHLS ILRDVSVFGE   180
RWGYDTATIN NRYSDLTSLI HVYTNHCVDT YNQGLRRLEG RFLSDWIVYN RFRRQLTISV   240
LDIVAFFPNY DIRTYPIQTA TQLTREVYLD LPFINENLSP AAVYPTFSAA ESAIIRSPHL   300
VDFLNSFTIY TDSLARSAYW GGHLVNSFRT GTTTNLIRSP LYGREGNTER PVTITASPSV   360
PIFRTLSYPT GLDNSNPVAG IEGVEFQNTI SRSIYRKSGP IDSFSELPPQ DASVSPAIGY   420
SHRLCHATFL ERISGPRIAG TVFSWTHRSA SPTNEVSPSR ITQIPWVKAH TLASGASVIK   480
GPGPFTGDIL TRNSMGELGT LRVTFTGRLP QSYYIRFRYA SVANRSGTFR YSQPPSYGIS   540
FPKTMDAGEP LTSRSFAHTT LFTPITFSRA QEEFDLYIQS GVYIDRIEFI PVTATFEAEY   600
DLERAQKVVN ALFTSTNQLG LKTDVTDYHI DQVSNLVACL SDEFCLDEKR ELSEKVKHAK   660
RLSDERNLLQ DPNFRGINRQ PDRGWRGSTD ITIQGGDDVF KENYVTLPGT FDECYPTYLY   720
QKIDESKLKA YTRYQLRGYI EDSQDLEIYL IRYNAKHEIV NVPGTGSLWP LSVENQIGPC   780
GEPNRCAPHL EWNPDLHCSC RDGEKCAHHS HHFSLDIDVG CTDLNEDLGV WVIFKIKTQD   840
GHARLGNLEF LEEKPLLGEA LARVKRAEKK WRDKRETLQL ETTIVYKEAK ESVDALFVNS   900
QYDRLQADTN IAMIHAADKR VHRIREAYLP ELSVIPGVNA AIFEELEERI FTAFSLYDAR   960
NIIKNGDFNN GLLCWNVKGH VEVEEQNNHR SVLVIPEWEA EVSQEVRVCP GRGYILRVTA  1020
YKEGYGEGCV TIHEIENNTD ELKFNNCVEE EVYPNNTVTC INYTATQEEY EGTYTSRNRG  1080
YDEAYGNNPS VPADYASVYE EKSYTDRRRE NPCESNRGYG DYTPLPAGYV TKELEYFPET  1140
DKVWIEIGET EGTFIVDSVE LLLMEE                                      1166
```

```
SEQ ID NO: 41          moltype = DNA  length = 3423
FEATURE                Location/Qualifiers
misc_feature           1..3423
                       note = Synthetic DNA sequence designed for plant expression
                       encodingTIC844 with an additional Alanine residue inserted
                       at position 2.
source                 1..3423
                       mol_type = other DNA
                       organism = synthetic construct
SEQUENCE: 41
atggctgaga tcaacaacca gaaccagtgc gtcccgtaca actgcctgag caaccctaag     60
gagatcatcc tgggtgagga acgcctggag accggcaaca ccgtagccga cattagcctg    120
ggcctcatca acttcctcta cagcaacttc gtgcccggcg gtggcttcat cgtgggcctc    180
ctggagctta tctgggcgct tcatcgagccg tcccagtgga acatcttcct cgcccagatc   240
gagcaactga tcagccagcg gatcgaggag ttcgctagga accaggccat ctcccgcctg    300
gagggactct ccaacctcta caaggtgtac gtgcgcgcgt tcagcgactg ggagaaggac    360
ccgaccaacc cggccctccg cgaggaaatg cgtatccagt tcaacgatat gaactcggcc    420
ctcatcaccg ccatcccgct cttccgcgtg cagaactacg aggtggccct cctgtccgtg    480
tacgttcaag ccgccaacct ccacctctcc atcctccgac gtgagcgt gttcggcgag     540
cgctggggct acgacaccgc caccatcaac aaccgctact ccgacctcac ctcccctcatc  600
cacgtttaca ccaaccactg cgtggacacg tacaaccagg gcctccgccg cctggagggc   660
cgcttcctct ccgactggat cgtgtacaac cgcttccgcc gccagctcac catctccgtc   720
ctggacatcg tcgccttctt tcccaactac gacatccgca cctaccctat ccagaccgcc   780
acccagctca cccgcgaggt ctacctcgac ctcccgttca tcaacgagaa cctcagccg    840
gccgccagct acccgacctt ctccgccgct gagtccgcca tcattcgcag ccgcactc    900
gtggacttcc tcaactcctt caccatctac accgactccc tcgcccgcta cgcctactgg   960
ggcggtcacc tcgtgaactc cttccgcacc ggcaccacta ccaacctcat ccgcagcccg  1020
ctctacggcc gcgagggcaa caccgagcgc ccggtgacca tcaccgccag ccgagcgtg   1080
cccatcttcc gcacccctcag ctacatcacc ggcctggaca cagcaaccc tgtggcgggc  1140
```

```
atcgagggcg tggagttcca gaacaccatc tccaggagca tctaccgcaa gagcggccct    1200
atcgacagct tcagcgagct gcctcctcag gacgccagcg tgagccctgc catcggctac   1260
agccacaggc tgtgccacgc caccttcctg gagcgcatca gcggcccctcg catcgcgggc   1320
accgtgttct cgtggaccca ccgcagcgcc tctcctacga acgaggtgtc tcctagtcgc   1380
atcacccaga tcccttgggt caaggcccac acctcggcta tgtcatcaag              1440
ggccctggct tcaccggtgg tgacatcctg accaggaact ctatgggcga gctgggcact   1500
ctgagggtca ctttcactgg ccgcctgcct cagtcttact acatccgctt ccgctacgct   1560
agtgtcgcta accgctctgg tactttccgc tactctcagc ctccgtctta cggtatctct   1620
ttccctaaga ctatgacgc tggtgagcgt ctgaccagta ggagcttcgc tcacactact    1680
ctgttcactc ctatccacttt ctctagggct caggaggagt tcgacctgta catccagtct   1740
ggtgtgtaca tcgacaggat cgagttcatc cccgtgaccg ccacgttcga ggccgagtac   1800
gaccttgagc gcgcccagaa ggctgtcaat gagctcttca cgtccagcaa tcagatcggc   1860
ctgaagaccg acgtcactga ctaccacatc gaccaagtct ccaacctcgt gggagtgcctc  1920
tccgatgagt tctgcctcga cgagaagaag gagctgtccg agaaggtgaa gcatgccaag   1980
cgtctcagcg acgagaggaa tctcctccag gaccccaatt tccgcggcat caacaggcag   2040
ctcgaccgcg gctggcgcgg cagcaccgac atcacgatcc agggcggcga cgatgtgttc   2100
aaggagaact acgtgactct cctgggcact ttcgacgagt gctacccccac ctacttgtac   2160
cagaagatcg atgagtccaa gctcaaggct tacactcgct accagctccg tggctactcc   2220
gaagacagcc aagacctcga gatttacctg atccgctaca acgccaagca cgagaccgtc   2280
aacgtgcccg gtactggttc cctcggccg ctgagcgccc cagcccgat cggcaagtgt    2340
gcccaccaca gccaccactt ctccttggac atcgatgtgg gctgcaccga cctgaacgag   2400
gacctcggag tctgggtcat cttcaagatc aagaccaacg cccacgc cgcgcctgggc    2460
aacctggagt tcctcgagga aagcccctg tcggtgagg ctctggccag ggtcaagagg    2520
gctgagaaga agtgagggga caagcgcgag aagctcgagt gggagaccaa catcgtttac   2580
aaggaggcca aggaggcgt cgacgccctg ttcgtgaact cccagtacga ccgcctgcag   2640
gccgacacca acatcgccat gatccacgct gccgacaaga gggtgcacag cattcgcgag   2700
gcctacctgc ctgagctgtc cgtgatccct ggtgtgaacg ctgccatctt tgaggagctg   2760
gagggccgca tctttaccgc attctccctg tacgacgccc gcaacgtgat caagaacggt   2820
gacttcaaca atggcctcag ctgctggaac gtcaagggcc acgtggacgt cgaggaacag   2880
aacaaccacc gctccgtcct ggtcgtccca gagtgggagg ctgaggtctc ccaagaggtc   2940
gcgtctgcc caggccgcgg ctacattctc agggtcaccg cttacaagga gggctacggt   3000
gagggctgtg tgaccatcca cgagatcgag aacaacaccg acgagcttaa gttctccaac   3060
tgcgtggagg aggaggtgta cccaaacaac accgttactt gcaacgacta caccgccacc   3120
caggaggagt acgagggcac ctacacttcc aggaacaggg gctacgatgg tgcctacgag   3180
agcaacagca cgcgttcctgc tgactacgct tccgcctacg aggagaaggc ctacacggat   3240
ggccgcaggg acaaccccttg cgagagcaac cgcggctacg gcgactacac tcccctgccc   3300
gccggctacg ttaccaagga gctggagtac ttccgggaga ctgacaaggt gtggatcgag   3360
atcggcgaga ccgagggcac cttcatcgtg gacagcgtgg agctgctcct gatggaggag   3420
tag                                                                 3423

SEQ ID NO: 42         moltype = AA   length = 1140
FEATURE               Location/Qualifiers
REGION                1..1140
                      note = Amino acid sequence of the chimeric protein TIC844
                       encoded by asynthetic DNA sequence wherein an additional
                       Alanine residue hasbeen inserted at position 2.
source                1..1140
                      mol_type = protein
                      organism = synthetic construct
SEQUENCE: 42
MAEINNQNQC VPYNCLSNPK EIILGEERLE TGNTVADISL GLINFLYSNF VPGGGFIVGL     60
LELIWGFIGP SQWDIFLAQI EQLISQRIEE FARNQAISRL EGLSNLYKVY VRAFSDWEKD    120
PTNPALREEM RIQFNDMNSA LITAIPLFRV QNYEVALLSV YVQAANLHLS ILRDVSVFGE    180
RWGYDTATIN NRYSDLTSLI HVYTNHCVDT YNQGLRRLEG RFLSDWIVYN RFRRQLTISV    240
LDIVAFFPNY DIRTYPIQTA TQLTREVYLD LPFINENLSP AASYPTFSAA ESAIIRSPHL    300
VDFLNSFTIY TDSLARYAYW GGHLVNSFRT GTTTNLIRSP LYGREGNTER PVTITASPSV    360
PIFRTLSYIT GLDNSNPVAG IEGVEFQNTI SRSIYRKSGP IDSFSELPPQ DASVSPAIGY    420
SHRLCHATFL ERISGPRIAG TVFSWTHRSA SPTNEVSPSR ITQIPWVKAH TLASGASVIK    480
GPGFTGGDIL TRNSMGELGT LRVTFTGRLP QSYYIRFRYA SVANRSGTFR YSQPPSYGIS    540
FPKTMDAGEP LTSRSFAHTT LFTPITFSRA QEEFDLYIQS GVYIDRIEFI PVTATFEAEY    600
DLERAQKAVN ELFTSSNQIG LKTDVTDYHI DQVSNLVECL SDEFCLDEKK ELSEKVKHAK    660
RLSDERNLLQ DPNFRGINRQ LDRGWRGSTD ITIQGGDDVF KENYVTLLGT FDECYPTYLY    720
QKIDESKLKA YTRYQLRGYI EDSQDLEIYL IRYNAKHETV NVPGTGSLWP LSAPSPIGKC    780
AHHSHHFSLD IDVGCTDLNE DLGVWVIFKI KTQDGHARLG NLEFLEEKPL VGEALARVKR    840
AEKKWRDKRE KLEWETNIVY KEAKESVDAL FVNSQYDRLQ ADTNIAMIHA ADKRVHSIRE    900
AYLPELSVIP GVNAAIFEEL EGRIFTAFSL YDARNVIKNG DFNNGLSCWN VKGHVDVEEQ    960
NNHRSVLVVP EWEAEVSQEV RVCPGRGYIL RVTAYKEGYG EGCVTIHEIE NNTDELKFSN   1020
CVEEEVYPNN TVTCNDYTAT QEEYEGTYTS RNRGYDGAYE SNSSVPADYA SAYEEKAYTD   1080
GRRDNPCESN RGYGDYTPLP AGYVTKELEY FPETDKVWIE IGETEGTFIV DSVELLLMEE   1140

SEQ ID NO: 43         moltype = DNA   length = 3423
FEATURE               Location/Qualifiers
misc_feature          1..3423
                      note = Synthetic DNA sequence designed for plant expression
                       encodingTIC844_8 with an additional Alanine residue
                       inserted at position2.
source                1..3423
                      mol_type = other DNA
                      organism = synthetic construct
```

```
SEQUENCE: 43
atggctgaga tcaacaacca gaaccagtgc gtcccgtaca actgcctgag caaccctaag    60
gagatcatcc tgggtgagga acgcctggag accggcaaca ccgtagccga cattagcctg   120
ggcctcatca acttcctcta cagcaacttc gtgcccggcg gtggcttcat cgtgggcctc   180
ctggagctta tctggggctt catcggcccg tcccagtgga acatcttcct cgcccagatc   240
gagcaactga tcagccagcg gatcgaggag ttcgctagga accaggccat ctcccgcctg   300
gagggactct ccaacctcta caaggtgtac gtgcgcgcgt tcagcgactg ggagaaggac   360
ccgaccaacc cggccctccg cgaggaaatg cgtatccagt tcaacgatat gaactcggcc   420
ctcatcaccg ccatcccgct cttccgcgtg cagaactacg aggtggcct cctgtccgtg    480
tacgttcaag ccgccaacct ccacctctcc atcctccgcg acgtgagcgt gttcggcgag   540
cgctggggct acgacaccgc caccatcaac aaccgctact ccgacctcac ctccctcatc   600
cacgtttaca ccaaccactg cgtggacacg tacaaccagg gcctccgccg cctggagggc   660
cgcttcctct ccgactggat cgtgtacaac cgcttccgcc gccagctcac catctccgtc   720
ctggacatcg tcgccttctt tcccaactac gacatccgca cctaccctat ccagaccgcc   780
acccagctca cccgcgaggt ctacctcgac ctcccgttca tcaacgagaa cctcagcccg   840
gccgccgtct acccgacctt ctccgccgct gagtccgcca tcattcgcag cccgcacctc   900
gtggacttcc tcaactcctt caccatctac accgactccc tcgcccgcag cgcctactgg   960
ggcggtcacc tcgtgaactc cttccgcacc ggcaccacta acctcatccg cagcccgtac  1020
ctctacggcc gcgagggcaa caccgagcgc ccggtgacca tcaccgccag cccgagcgtg  1080
cccatcttcc gcaccctcag ctaccccacc ggcctggaca cagcaaccc tgtggcgggc   1140
atcgaggcg tggagttcca gaacaccatc tccaggagca tctaccgcaa gagcggccct   1200
atcgacagct tcagcgagct gcctcctcag gacgccaagc tgagcctgc catcgcgtac    1260
agccacaggc tgtgccacgc caccttcctg gagcgcatca gcggccctcg catcgcgggc  1320
accgtgttct cgtggaccca ccgcagcgcc tctcctacga cgaggtgtc tcctagtcgc   1380
atcacccaga tcccttgggt caaggccac accctggcta gtgcgctag tgtcatcaag    1440
ggccctggct tcaccggtgg tgacatcctg accaggaact ctatgggcga gctgggcact  1500
ctgagggtca ctttcactgg ccgcctgcct cagtcttact acatccgctt ccgctacgct  1560
agtgtcgcta accgctctgg tacttccgc tactctcagc ctccgtctta cggtatctct    1620
ttccctaaga ctatgacgc tggtgagcct ctgaccagta ggagcttcgc tcacactact    1680
ctgttcactc ctatcacttt ctctagggct caggaggagt tcgacctgta tcatccagtc  1740
ggtgtgtaca tcgacaggat cgagttcatc cccgtgaccg ccacgttcga ggccgagtac  1800
gaccttgagc gcgcccagaa ggctgtcaat gagctcttca cgtccagcaa tcagatcggc  1860
ctgaagaccg acgtcactga ctaccacatc gaccaagtct ccaacctcgt ggagtgcctc  1920
tccgatgagt tctgcctcga cgagaagaag gagctcgacg agaaggtgaa gcatgccaag  1980
cgtctcagcg acgagaggaa tctcctccag gaccccaatt tccgcggcat caacaggcag  2040
ctcgaccgcg gctggcgcgg cagcaccgac atcacgatcc agggcggcga cgatgtgttc  2100
aaggagaact acgtgactct cctgggcact tcgacgagt gctacctac ctacttgtac    2160
cagaagatcg atgagtccaa gctcaaggct tacactcgct accagctccg cggctacatc  2220
gaagcagcc aagacctcga gatttacctg atccgctaca acgccaagca cgagaccgtc   2280
aacgtgcccg gtactggttc cctctggccg ctgagcgccc ccagcccgat cggcaagtgt  2340
gcccaccaca gccaccactt ctccttggac atcgatgtgg gctgcaccga cctgaacgag  2400
gacctcgag tctgggtcat cttcaagatc aagacccagg acggcacgc gcgcctgggc    2460
aacctggagt tcctccgagga aagcccctg gtcggtgagg ctctggccag ggtcaaggag   2520
gctgagaaga agtggaggga caagcgcgag aagctcgagt gggagaccaa catcgtttac  2580
aaggaggcca aggagagcgt cgacgccctg ttcgtgaact cccagtacga ccgcctgcag  2640
gccgacacca acatcgccat gatccacgct gccgacaaga gggtgcacag cattcgcgag  2700
gcctacctgc ctgagctgtc cgtgatccct ggtgtgaacg ctgccatctt tgaggagctg  2760
gagggccgca tctttaccgc attctcccctg tacgacgccc gcaacgtgat caagaacggt  2820
gacttcaaca atgcctcag ctgctggaac gtcaagggcc acgtggacgt cgaggaacag    2880
aacaaccacc gctccgtcct ggtcgtccca gagtgggagg ctgaggtctc caagaggtc   2940
cgcgtctgcc caggccgcgg ctacattctc agggtcaccg cttacaagga gggctacggt  3000
gagggctgtg tgaccatcca cgagatcgag aacaacaccg acgagcttaa gttctccaac  3060
tgcgtggagg aggaggtgta cccaaacaac accgttactt gcaacgacta caccgccacc  3120
caggaggagt acgagggcac ctacacttcc aggaacaggg gctacgatgg tgcctacgag  3180
agcaacagca gcgttcctgc tgactacgct ccgcctacg aggagaaggc ctacacggat   3240
ggccgcaggg acaaccttg cgagagcaac cgcggctacg gcgactacac tcccctgccc   3300
gccggctacg ttaccaagga gctggagtac ttcccggaga ctgacaaggt gtggatcgag  3360
atcggcgaga ccgagggcac cttcatcgtg gacagcgtgg agctgctcct gatggaggag  3420
tag                                                                3423

SEQ ID NO: 44        moltype = AA  length = 1140
FEATURE              Location/Qualifiers
REGION               1..1140
                     note = Amino acid sequence of the engineered insecticidal
                       chimericprotein TIC844_8 encoded by a synthetic DNA
                       sequence wherein anadditional Alanine residue has been
                       inserted at position 2.
source               1..1140
                     mol_type = protein
                     organism = synthetic construct SEQUENCE: 44
MAEINNQNQC VPYNCLSNPK EIILGEERLE TGNTVADISL GLINFLYSNF VPGGGFIVGL   60
LELIWGFIGP SQWDIFLAQI EQLISQRIEE FARNQAISRL EGLSNLYKVY VRAFSDWEKD  120
PTNPALREEM RIQFNDMNSA LITAIPLFRV QNYEVALLSV YVQAANLHLS ILRDVSVFGE  180
RWGYDTATIN NRYSDLTSLI HVYTNHCVDT YNQGLRRLEG RFLSDWIVYN RFRRQLTISV  240
LDIVAFFPNY DIRTYPIQTA TQLTREVYLD LPFINENLSP AAVYPTFSAA ESAIIRSPHL  300
VDFLNSFTIY TDSLARSAYW GGHLVNSFRT GTTTNLIRSP LYGREGNTER PVTITASPSV  360
PIFRTLSYPT GLDNSNPVAG IEGVEFQNTI SRSIYRKSGP IDSFSELPPQ DASVSPAIGY  420
SHRLCHATFL ERISGPRIAG TVFSWTHRSA SPTNEVSPSR ITQIPWVKAH TLASGASVIK  480
```

-continued

```
GPGFTGGDIL TRNSMGELGT LRVTFTGRLP QSYYIRFRYA SVANRSGTFR YSQPPSYGIS  540
FPKTMDAGEP LTSRSFAHTT LFTPITFSRA QEEFDLYIQS GVYIDRIEFI PVTATFEAEY  600
DLERAQKAVN ELFTSSNQIG LKTDVTDYHI DQVSNLVECL SDEFCLDEKK ELSEKVKHAK  660
RLSDERNLLQ DPNFRGINRQ LDRGWRGSTD ITIQGGDDVF KENYVTLLGT FDECYPTYLY  720
QKIDESKLKA YTRYQLRGYI EDSQDLEIYL IRYNAKHETV NVPGTGSLWP LSAPSPIGKC  780
AHHSHHFSLD IDVGCTDLNE DLGVWVIFKI KTQDGHARLG NLEFLEEKPL VGEALARVKR  840
AEKKWRDKRE KLEWETNIVY KEAKESVDAL FVNSQYDRLQ ADTNIAMIHA ADKRVHSIRE  900
AYLPELSVIP GVNAAIFEEL EGRIFTAFSL YDARNVIKNG DFNNGLSCWN VKGHVDVEEQ  960
NNHRSVLVVP EWEAEVSQEV RVCPGRGYIL RVTAYKEGYG EGCVTIHEIE NNTDELKFSN  1020
CVEEEVYPNN TVTCNDYTAT QEEYEGTYTS RNRGYDGAYE SNSSVPADYA SAYEEKAYTD  1080
GRRDNPCESN RGYGDYTPLP AGYVTKELEY FPETDKVWIE IGETEGTFIV DSVELLLMEE  1140
```